United States Patent
Shin et al.

(10) Patent No.: US 12,167,680 B2
(45) Date of Patent: Dec. 10, 2024

(54) ORGANIC ELECTRIC ELEMENT, DISPLAY PANEL COMPRISING THE SAME AND DISPLAY DEVICE COMPRISING THE SAME

(71) Applicants: LG DISPLAY CO., LTD., Seoul (KR); LG CHEM, LTD., Seoul (KR)

(72) Inventors: Jicheol Shin, Gyeonggi-do (KR); Seonkeun Yoo, Gyeonggi-do (KR); Jeongdae Seo, Gyeonggi-do (KR); Shinhan Kim, Gyeonggi-do (KR); JooYong Yoon, Gyeonggi-do (KR); Jun Yun, Gyeonggi-do (KR); DongHeon Kim, Gyeonggi-do (KR); YongHan Lee, Gyeonggi-do (KR); SungJae Lee, Gyeonggi-do (KR)

(73) Assignees: LG DISPLAY CO., LTD., Seoul (KR); LG CHEM, LTD., Seoul (KR)

(*) Notice: Subject to any disclaimer, the term of this patent is extended or adjusted under 35 U.S.C. 154(b) by 737 days.

(21) Appl. No.: 17/137,802

(22) Filed: Dec. 30, 2020

(65) Prior Publication Data
US 2021/0202859 A1    Jul. 1, 2021

(30) Foreign Application Priority Data
Dec. 31, 2019    (KR) .................. 10-2019-0179992

(51) Int. Cl.
| | | |
|---|---|---|
| H01L 51/00 | (2006.01) | |
| C07C 211/61 | (2006.01) | |
| C07C 255/47 | (2006.01) | |
| C07D 221/20 | (2006.01) | |
| C07D 471/04 | (2006.01) | |
| C09K 11/06 | (2006.01) | |
| H10K 85/60 | (2023.01) | |
| H10K 50/17 | (2023.01) | |
| H10K 50/19 | (2023.01) | |
| H10K 101/30 | (2023.01) | |

(52) U.S. Cl.
CPC .......... *H10K 85/615* (2023.02); *C07C 211/61* (2013.01); *C07C 255/47* (2013.01); *C07D 221/20* (2013.01); *C07D 471/04* (2013.01); *C09K 11/06* (2013.01); *H10K 85/626* (2023.02); *H10K 85/633* (2023.02);
(Continued)

(58) Field of Classification Search
None
See application file for complete search history.

(56) References Cited

U.S. PATENT DOCUMENTS

| | | |
|---|---|---|
| 10,043,985 B2 | 8/2018 | Kim et al. |
| 11,877,464 B2 | 1/2024 | Kim et al. |

(Continued)

FOREIGN PATENT DOCUMENTS

| | | |
|---|---|---|
| EP | 3 176 844 A1 | 6/2017 |
| EP | 252 052 A1 | 12/2017 |

(Continued)

OTHER PUBLICATIONS

Machine English translation of Kim et al. (WO 2018/221871 A1). Jul. 8, 2023.*

(Continued)

*Primary Examiner* — Jay Yang
(74) *Attorney, Agent, or Firm* — Morgan, Lewis & Bockius LLP

(57) ABSTRACT

Provided are an organic electric element, a display panel and a display device including the organic electric element which include a charge generating layer including a first layer comprising a first compound and a second compound and a second layer comprising a third compound so that they may have excellent efficiency or lifespan.

13 Claims, 3 Drawing Sheets

(52) U.S. Cl.
CPC ......... *H10K 85/636* (2023.02); *H10K 85/654* (2023.02); *H10K 85/6572* (2023.02); *C07C 2603/10* (2017.05); *C07C 2603/18* (2017.05); *C07C 2603/97* (2017.05); *C09K 2211/1007* (2013.01); *C09K 2211/1011* (2013.01); *C09K 2211/1018* (2013.01); *H10K 50/17* (2023.02); *H10K 50/19* (2023.02); *H10K 85/624* (2023.02); *H10K 2101/30* (2023.02)

(56) References Cited

U.S. PATENT DOCUMENTS

| | | | | |
|---|---|---|---|---|
| 2016/0043327 | A1* | 2/2016 | Yoo | H10K 85/6576 257/40 |
| 2017/0054084 | A1* | 2/2017 | Kim | H10K 85/626 |
| 2019/0207123 | A1 | 7/2019 | Yoon et al. | |
| 2020/0144552 | A1 | 5/2020 | Kim et al. | |

FOREIGN PATENT DOCUMENTS

| | | |
|---|---|---|
| EP | 333 921 A1 | 6/2018 |
| KR | 10-2017-0023328 A | 3/2017 |
| KR | 10-2018-0131100 A | 12/2018 |
| WO | 2018/221871 A1 | 12/2018 |

OTHER PUBLICATIONS

Extended European Search Report dated Jun. 4, 2021, issued in corresponding European Patent Application No. 20217607.9.

Office Action issued in Korean Patent Application No. 10-2019-0179992 dated Jul. 22, 2024.

* cited by examiner

ORGANIC ELECTRIC ELEMENT, DISPLAY PANEL COMPRISING THE SAME AND DISPLAY DEVICE COMPRISING THE SAME

CROSS REFERENCE TO RELATED APPLICATION

This application claims priority from Korean Patent Application No. 10-2019-0179992, filed on Dec. 31, 2019, which is hereby incorporated by reference for all purposes as if fully set fourth herein.

BACKGROUND

Technical Field

Embodiments of the disclosure relate to an organic electric element, a display panel, and a display device including the organic electric element.

Discussion of the Related Art

In general, an organic light emitting phenomenon refers to the phenomenon of converting electrical energy into light energy by means of an organic material. An organic electric element refers to an electric element using the organic light emitting phenomenon.

An organic electric element using the organic light emitting phenomenon may be applied to a display device. Since the portable display device is driven by a battery, which is a limited power source, an organic electric element used in the portable display device requires excellent light emission efficiency. In addition, since the image should be displayed normally during use of the electronic device, a long life of the organic electric element may be also required.

In order to improve efficiency, lifespan and driving voltage in the organic electric element, research has been conducted on the organic material included in the organic electric element.

SUMMARY

Accordingly, embodiments of the present disclosure are directed to an organic electric element, a display panel, and a display device including the organic electric element that substantially obviate one or more of the problems due to limitations and disadvantages of the related art.

Embodiments may provide an organic electric element having high efficiency or long life.

Embodiments may provide a display panel having high efficiency or long life by including the above-described organic electric element.

Further, embodiments may provide a display device having high efficiency or long life by including the above-described display panel.

Additional features and aspects will be set forth in the description that follows, and in part will be apparent from the description, or may be learned by practice of the inventive concepts provided herein. Other features and aspects of the inventive concepts may be realized and attained by the structure particularly pointed out in the written description, or derivable therefrom, and the claims hereof as well as the appended drawings.

To achieve these and other aspects of the inventive concepts, as embodied and broadly described, an organic electric element comprises a first electrode, a second electrode and an organic layer.

The organic layer is positioned between the first electrode and the second electrode.

The organic layer comprises a first stack comprising a first emitting layer, a second stack comprising a second emitting layer, and a charge generating layer positioned between the first stack and the second stack.

The charge generating layer comprises a first layer and a second layer.

The first layer comprises a first compound and a second compound.

The first compound is represented by one or more of the following chemical formula 1 and chemical formula 2.

[chemical formula 1]

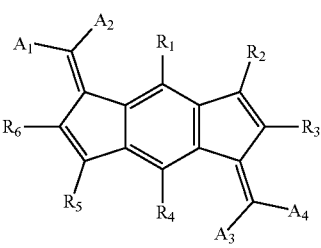

[chemical formula 2]

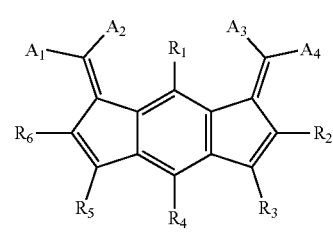

The second compound is represented by the following chemical formula 3.

[chemical formula 3]

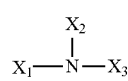

The second layer comprises a third compound represented by the following chemical formula 4.

[chemical formula 4]

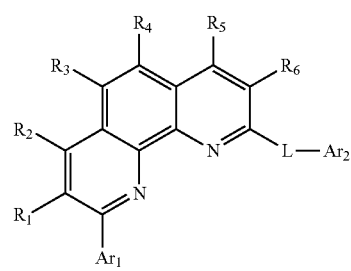

In another aspect, embodiments may provide a display panel comprising a subpixel comprising the organic electric element.

In another aspect, embodiments may provide a display device comprising the display panel and a driving circuit for driving the display panel.

According to embodiments, it is possible to provide the organic electric device having high luminous efficiency and long life.

According to embodiments, it is possible to provide a display panel including the organic electric device having a high luminous efficiency and long life and a display device comprising the same.

It is to be understood that both the foregoing general description and the following detailed description are exemplary and explanatory and are intended to provide further explanation of the inventive concepts as claimed.

DESCRIPTION OF DRAWINGS

The accompanying drawings, which are included to provide a further understanding of the disclosure and are incorporated in and constitute a part of this application, illustrate embodiments of the disclosure and together with the description serve to explain various principles. In the drawings.

DETAILED DESCRIPTION

Figure 1:
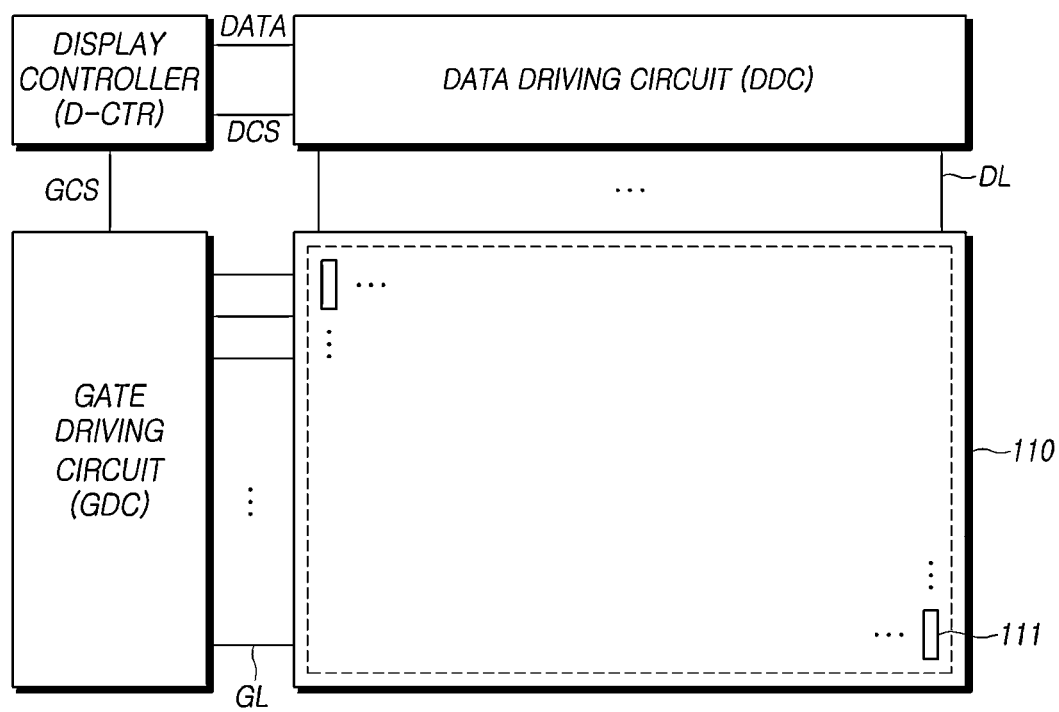
FIG. 1 is a system configuration diagram of a display device according to embodiments.

In the following description of examples or embodiments of the present invention, reference will be made to the accompanying drawings in which it is shown by way of illustration specific examples or embodiments that can be implemented, and in which the same reference numerals and signs can be used to designate the same or like components even when they are shown in different accompanying drawings from one another. Further, in the following description of examples or embodiments of the present invention, detailed descriptions of well-known functions and components incorporated herein will be omitted when it is determined that the description may make the subject matter in some embodiments of the present invention rather unclear. The terms such as "including", "having", "containing", "constituting" "make up of", and "formed of" used herein are generally intended to allow other components to be added unless the terms are used with the term "only". As used herein, singular forms are intended to include plural forms unless the context clearly indicates otherwise.

Terms, such as "first", "second", "A", "B", "(A)", or "(B)" may be used herein to describe elements of the present invention. Each of these terms is not used to define essence, order, sequence, or number of elements etc., but is used merely to distinguish the corresponding element from other elements.

When it is mentioned that a first element "is connected or coupled to", "contacts or overlaps" etc. a second element, it should be interpreted that, not only can the first element "be directly connected or coupled to" or "directly contact or overlap" the second element, but a third element can also be "interposed" between the first and second elements, or the first and second elements can "be connected or coupled to", "contact or overlap", etc. each other via a fourth element. Here, the second element may be included in at least one of two or more elements that "are connected or coupled to", "contact or overlap", etc. each other.

When time relative terms, such as "after," "subsequent to," "next," "before," and the like, are used to describe processes or operations of elements or configurations, or flows or steps in operating, processing, manufacturing methods, these terms may be used to describe non-consecutive or non-sequential processes or operations unless the term "directly" or "immediately" is used together.

In addition, when any dimensions, relative sizes etc. are mentioned, it should be considered that numerical values for an elements or features, or corresponding information (e.g., level, range, etc.) include a tolerance or error range that may be caused by various factors (e.g., process factors, internal or external impact, noise, etc.) even when a relevant description is not specified. Further, the term "may" fully encompasses all the meanings of the term "can".

The term "halo" or "halogen" as used herein refers to fluorine (F), bromine (Br), chlorine (Cl), or iodine (I) unless otherwise indicated.

As used herein, the term "alkyl" or "alkyl group" refers to a saturated aliphatic functional radical of 1 to 60 carbon atoms with a single bond therein, including a straight chain alkyl group, a branched chain alkyl group, a cycloalkyl (alicyclic) group, an alkyl-substituted cycloalkyl group, and a cycloalkyl-substituted alkyl group, unless otherwise indicated.

The term "haloalkyl group" or "halogenalkyl group", as used herein, means a halogen-substituted alkyl group unless otherwise specified.

The term "heteroalkyl group", as used herein, means that at least one of the carbon atoms constituting the alkyl group has been replaced with a heteroatom.

As used herein, the terms "alkenyl group" and "alkynyl group", refer to a straight or branched chain of 2 to 60 carbon atoms with a double and a triple bond therein, respectively, unless stated otherwise, but are not limited thereto.

Unless otherwise stated, the term "cycloalkyl" as used herein refers to an alkyl forming a ring having 3 to 60 carbon atoms, without being limited thereto.

Unless otherwise stated, the term "alkoxyl group", "alkoxy group", or "alkyloxy group" as used herein means an alkyl group of 1 to 60 carbon atoms having an oxygen radical attached thereto, but is not limited thereto.

As used herein, the term "alkenoxyl group", "alkenoxy group", "alkenyloxyl group", or "alkenyloxy group" means an alkenyl group of 2 to 60 carbon atoms having an oxygen radical attached thereto, unless otherwise stated, but is not limited thereto.

As used herein, the term "aryloxyl group" or "aryloxy group" means an aryl group of 6 to 60 carbon atoms having an oxygen radical attached thereto unless otherwise specified, but is not limited thereto.

As used herein, the terms "aryl group" and "arylene group" each refer to having 6 to 60 carbon atoms unless otherwise stated, but are not limited thereto. In the present disclosure, an aryl group or an arylene group means a single or multiple aromatic ring, including an aromatic ring which is formed as neighboring substituents participate in a bond or a reaction. For example, the aryl group may be a phenyl group, a biphenyl group, a terphenyl group, a naphthyl group, an anthracenyl group, a fluorene group, a spirofluorene group, or a spirobifluorene group.

The prefix "aryl" or "ar" means a radical substituted with an aryl group. For example, an arylalkyl group is an alkyl group substituted with an aryl group and an arylalkenyl group is an alkenyl group substituted with an aryl group. In this regard, the radical substituted with an aryl group has the number of carbon atoms described herein.

Also, when prefixes are named consecutively, it means that the substituents are listed in the order described first. By way of example, an arylalkoxy group means an alkoxy group substituted with an aryl group, an alkoxylcarbonyl group means a carbonyl group substituted with an alkoxyl group, and an arylcarbonylalkenyl group means an alkenyl group substituted with an arylcarbonyl group wherein the arylcarbonyl group is a carbonyl group substituted with an aryl group.

As used herein, the term "heteroalkyl" means an alkyl bearing one or more heteroatoms unless otherwise indicated. As used herein, the terms "heteroaryl group" and "heteroarylene group" refer respectively to an aryl group and an arylene group of 2 to 60 carbon atoms bearing one or more heteroatoms therein, unless otherwise specified, without being limited thereto. It may include at least one of a single ring and multiple rings, and may be formed by combining adjacent functional groups.

Unless otherwise indicated, the term "heterocyclic group" as used herein, refers to at least one of heteroaliphatic rings and heteroaromatic rings of 2 to 60 carbon atoms bearing one or more heteroatoms as a ring member thereof, which may be mono- or multi-cyclic and may be formed as neighboring functional groups combine with each other.

The term "heteroatom" as used herein refers to N, O, S, P, or Si unless otherwise stated.

"Heterocyclic groups" may also include rings comprising SO2, in place of carbon atoms, as a ring member. For example, a "heterocyclic group" includes the following compounds.

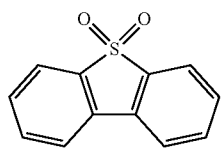 [SMILES: O=S1(=O)c2ccccc2-c2ccccc21]

Unless otherwise stated, the term "aliphatic" as used herein means an aliphatic hydrocarbon of 1 to 60 carbon atoms, and the "aliphatic ring" means an aliphatic hydrocarbon ring of 3 to 60 carbon atoms.

Unless otherwise stated, the term "ring" as used herein refers to an aliphatic ring of 3 to 60 carbon atoms, an aromatic ring of 6 to 60 carbon atoms, a hetero ring of 2 to 60 carbon atoms, or a fused ring consisting of a combination thereof whether or not it is saturated or unsaturated.

Other hetero-compounds or hetero-radicals other than the aforementioned hetero-compounds include, but are not limited to, one or more heteroatoms.

Unless otherwise stated, the term "carbonyl" as used herein is represented by —COR', wherein R' is hydrogen, an alkyl group of 1 to 20 carbon atoms, an aryl group of 6 to 30 carbon atoms, a cycloalkyl group of 3 to 30 carbon atoms, an alkenyl group of 2 to 20 carbon atoms, an alkynyl group of 2 to 20 carbon atoms, or a combination thereof.

Unless otherwise specified, the term "ether" as used herein is represented by —R—O—R', wherein R and R' are each independently hydrogen, an alkyl group of 1 to 20 carbon atoms, an aryl group of 6 to 30 carbon atoms, a cycloalkyl group of 3 to 30 carbon atoms, an alkenyl group of 2 to 20 carbon atoms, an alkynyl group of 2 to 20 carbon atoms, or a combination thereof.

Also, unless explicitly stated otherwise, the term "substituted" in the expression "substituted or unsubstituted" means having at least one substituent selected from the group consisting of, but not limited to, deuterium, halogen, an amino group, a nitrile group, a nitro group, a C1-C20 alkyl group, a C1-C20 alkoxyl group, a C1-C20 alkylamine group, a C1-C20 alkylthiophene group, a C6-C20 arylthiophene group, a C2-C20 alkenyl group, a C2-C20 alkynyl, a C3-C20 cycloalkyl group, a C6-C20 aryl group, a deuterium-substituted C6-C20 aryl group, a C8-C20 aryl alkenyl group, a silane group, a boron group, a germanium group, and a C2-C20 hetero-ring.

Also, unless otherwise stated, the chemical formulas used in the present invention are as defined for the exponent parts of the substituent in the following chemical formula:

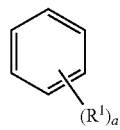

wherein,
when a is an integer of 0, the substituent R1 being null,
when a is an integer of 1, one substituent R1 is bonded to any one of the constituent carbon atoms of the benzene ring,
when a is an integer of 2 or 3, the substituents R1's, which may be the same or different, are each bonded as represented below, and
when a is an integer of 4 to 6, the substituents R1's are bonded to the constituents carbon atoms of the benzene ring in the same manner
while the hydrogens bonded to the constituent carbon atoms of the benzene ring are not indicated:

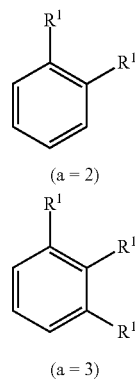

In the present specification, the formation of a ring by combining substituents with each other means that adjacent groups combine with each other to form a monocycle or single ring, a ring aggregated or a conjugated multi-cycle, and the monocycle, the ring aggregated and the formed conjugated multicycle may include the heterocycle including at least one heteroatom, and may include aromatic and non-aromatic rings.

In the present specification, the organic electric element may mean a component(s) between an anode and a cathode, or an organic light emitting diode including the anode, the cathode and the component(s) positioned therebetween.

In the present specification, the organic electric element may mean one of an organic electric device, the organic light emitting diode and the panel including the same, and an electronic device including the panel and a circuit. For example, the electronic device includes a display device, a lighting device, a solar cell, a portable or mobile terminal (eg, a smart phone, a tablet, a PDA, an electronic dictionary, a PMP, etc.), a navigation terminal, a game machine, various TVs, and various computers monitor and the like, but is not limited thereto, and may be any type of device as long as the component(s) are included.

Hereinafter, exemplary embodiments of the present disclosure will be described in detail with reference to the accompanying drawings.

FIG. 1 is a system configuration diagram of a display device according to embodiments.

Referring to FIG. 1, the display device 100 in accordance with embodiments of the present disclosure includes a display panel 110 in which a plurality of data lines DL and a plurality of gate lines GL are arranged and a plurality of sub-pixels 111 defined by the plurality of data lines DL and the plurality of gate lines GL is arranged, a data driving circuit DDC (or a data driver) for driving the plurality of data lines DL, a gate driving circuit GDC (or a gate driver) for driving the plurality of gate lines GL, a controller D-CTR controlling the data driving circuit DDC and the gate driving circuit GDC, and the like.

The controller D-CTR controls operations of the data driving circuit DDC and the gate driving circuit GDC by supplying respective control signals (DCS, GCS) to the data driving circuit DDC and the gate driving circuit GDC.

The controller D-CTR starts the scan of pixels according to timings processed in each frame, converts image data inputted from other devices or other image providing sources to be adapted to a data signal form used in the data driving circuit DDC and then outputs image data DATA resulted from the converting, and causes the data to be loaded into the pixels at a pre-configured time according to the scan.

The controller D-CTR may be implemented as a separate component from the data driving circuit DDC or may be integrated with data driving circuit DDC so the controller D-CTR can be implemented as an integrated circuit.

The data driving circuit DDC drives the plurality of data lines DL by providing data voltages corresponding to image data DATA received from the controller D-CTR to the data lines DL. Here, the data driving circuit DDC is sometimes referred to as a source driving circuit or a source driver.

The data driving circuit DDC may include at least one source driver integrated circuit SDIC to be implemented.

Each source driver integrated circuit SDIC may include a shift register, a latch circuit, a digital to analog converter DAC, an output buffer, and/or the like.

In some instances, each source driver integrated circuit SDIC may further include one or more analog to digital converters ADC.

The gate driving circuit GDC sequentially drives a plurality of gate lines GL by sequentially providing scan signals to the plurality of gate lines GL. Here, the gate driving circuit GDC is sometimes referred to as a scan driving circuit or a scan driver.

The gate driving circuit GDC may include at least one gate driver integrated circuit GDIC to be implemented.

Each gate driver integrated circuit GDIC may include a shift register, a level shifter, and/or the like.

Each gate driver integrated circuit GDIC may be connected to a bonding pad of the display panel 110 in a tape automated bonding (TAB) type or a chip on glass (COG) type, or be directly disposed on the display panel 110 as being implemented in a gate in panel (GIP) type. In some instances, the gate driver integrated circuit GDIC may be disposed to be integrated with the display panel 110. Further, each gate driver integrated circuit GDIC may be implemented in a chip on film (COF) type in which the gate driver integrated circuit GDIC is mounted on a film connected with the display panel 110.

According to the controlling of the controller D-CTR, the gate driving circuit GDC sequentially provides scan signals of an on-voltage or an off-voltage to the plurality of gate lines GL.

When a specific gate line is asserted by a scan signal from the gate driving circuit GDC, the data driving circuit DDC converts image data DATA received from the controller D-CTR into analog data voltages and provides the obtained analog data voltages to the plurality of data lines DL.

The data driving circuit DDC may be located on, but not limited to, only one side (e.g., an upper side or a lower side) of the display panel 110, or in some instances, be located on, but not limited to, two sides (e.g., the upper side and the lower side) of the display panel 110 according to driving schemes, panel design schemes, or the like.

The gate driving circuit GDC may be located on, but not limited to, only one side (e.g., a left side or a right side) of the panel 110, or in some instances, be located on, but not limited to, two sides (e.g., the left side and the right side) of the display panel 110 according to driving schemes, panel design schemes, or the like.

The display device 100 according to embodiments of the present disclosure may be one of various types of display devices, such as, a liquid crystal display device, an organic light emitting display device, a plasma display device, or the like.

In case the display device 100 according to embodiments of the present disclosure is an organic light emitting display device, each sub-pixel 111 arranged in the display panel 110 may include circuit components, such as an organic light emitting diode (OLED), which is a self-emissive element, a driving transistor for driving the organic light emitting diode OLED, and the like.

Types of circuit elements and the number of the circuit elements included in each subpixel 111 may be different depending on types of the panel (e.g., an LCD panel, an OLED panel, etc.), provided functions, design schemes/features, or the like.

Figure 2:
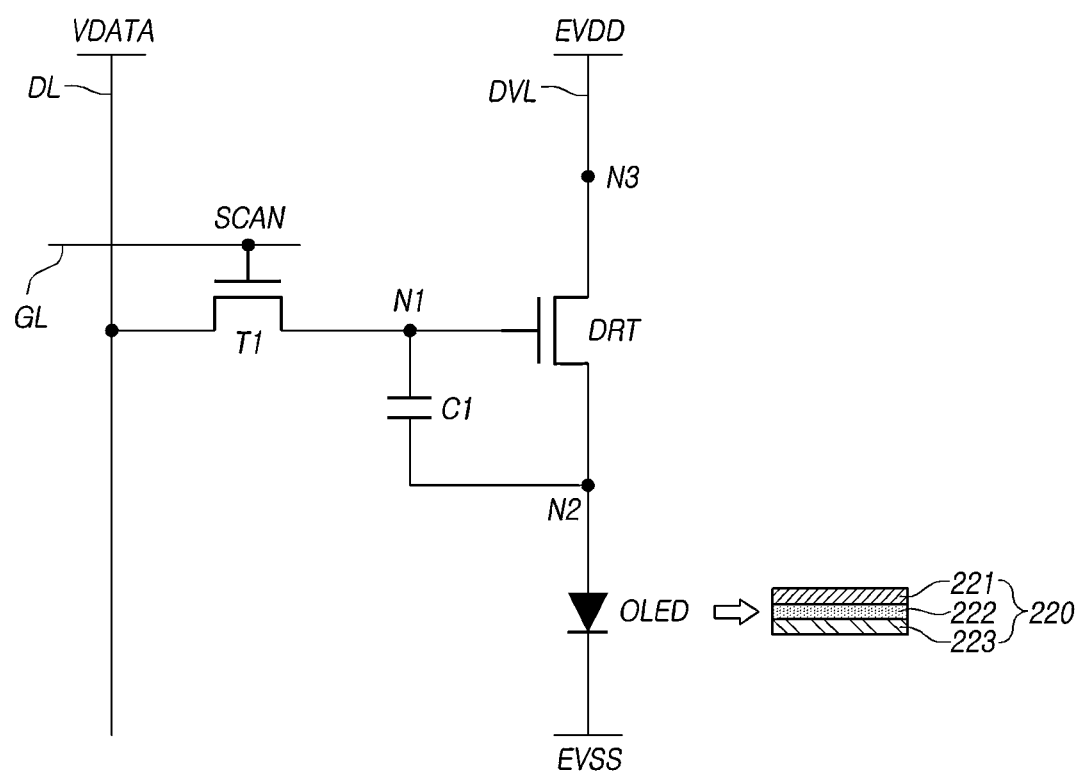
FIG. 2 is a view illustrating a subpixel circuit of a display panel according to embodiments.

FIG. 2 is a view illustrating a subpixel circuit of a display panel according to embodiments.

Referring to FIG. 2, each subpixel 111 may include an organic light emitting diode OLED and a driving transistor DRT for driving the organic light emitting diode OLED as basic circuit components.

Referring to FIG. 2, each sub-pixel 111 may further include a first transistor T1 allowing a data voltage VDATA to be applied to a first node N1 corresponding to a gate node of the driving transistor DRT, and a storage capacitor C1 for remaining a data voltage VDATA corresponding to an image signal voltage or a voltage corresponding to this during one frame time.

The organic light emitting diode OLED may include a first electrode 221 (an anode electrode or a cathode electrode), a light emitting layer 222, a second electrode 223 (the cathode electrode or the anode electrode), and the like.

In one embodiment, a low-level voltage EVSS may be applied to the second electrode 223 of the organic light emitting diode OLED.

The driving transistor DRT causes the organic light emitting diode OLED to be driven by providing a driving current to the organic light emitting diode OLED.

The driving transistor DRT includes a first node N1, a second node N2 and a third node N3.

The first node N1 of the driving transistor DRT may be a node corresponding to the gate node thereof, and may be electrically connected to a source node or a drain node of the first transistor T1.

The second node N2 of the driving transistor DRT may be electrically connected to the first electrode 221 of the organic light emitting diode OLED and may be a source node or a drain node.

The third node N3 of the driving transistor DRT may be the drain node or the source node as a node to which a driving voltage EVDD is applied, and may be electrically connected to a driving voltage line DVL used to supply a driving voltage EVDD.

The first transistor T1 may be electrically connected between a data line DL and the first node N1 of the driving transistor DRT and may be controlled by a scan signal SCAN that is provided through a gate line and applied to the gate node of the first transistor T1.

The storage capacitor C1 may be electrically connected between the first node N1 and the second node N2 of the driving transistor DRT.

The storage capacitor C1 is an external capacitor intentionally designed to be located outside of the driving transistor DRT, not an internal storage, such as a parasitic capacitor (e.g., a Cgs, a Cgd) that presents between the first node N1 and the second node N2 of the driving transistor DRT.

Figure 3:
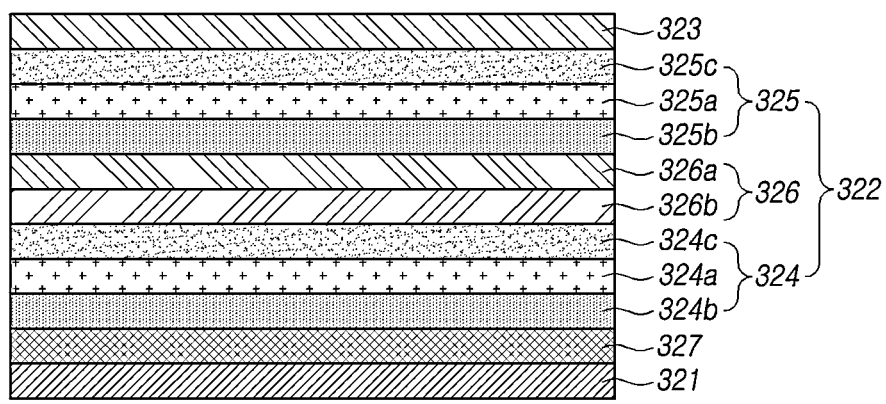
FIG. 3 is a schematic cross-sectional view of an organic electric device according to embodiments.

FIG. 3 is a cross-sectional view of a display device according to the embodiments.

Referring to FIG. 3, an organic electric element 320 according to the embodiments includes a first electrode 321 and a second electrode 323, an organic layer 322 positioned therebetween.

The first electrode 321 may be an anode and the second electrode 323 may be a cathode. In the case of an inverted type, the first electrode 321 may be a cathode and the second electrode 323 may be an anode.

For example, the first electrode 321 may be a transparent electrode, and the second electrode 323 may be a reflective electrode. In another example, the first electrode 321 may be a reflective electrode, and the second electrode 323 may be a transparent electrode.

The organic layer 322 may include a plurality of layers which is located between the first electrode 321 and the second electrode 323 and includes an organic material.

The organic layer includes a first stack 324, a second stack 325, and a charge generating layer 326 positioned between the first stack 324 and the second stack 325.

The organic electric element 320 may be a tandem organic electric element including a plurality of stacks each including a light emitting layer. The plurality of light emitting layers may be made of the same material as each other, or may be made of different materials from each other.

The first stack 324 includes a first emitting layer 324a. The first emitting layer 324a may include, for example, a host material and a dopant.

The first stack 324 may further include a first hole transport layer 324b and a first electron transport layer 324b.

The first hole transport layer 324b may be positioned between the first light emitting layer 324a and one of the first electrode 321 and the second electrode 323 as an anode electrode. The first electron transport layer 324c may be positioned between the first light emitting layer 324a and one of the first electrode 321 and the second electrode 323 as a cathode electrode. For example, when the first electrode 321 is the anode electrode and the second electrode 323 is the cathode electrode, the first hole transport layer 324b may be positioned on the first electrode 321, the first light emitting layer 324a may be positioned on the first hole transport layer 324b, and the first electron transport layer 324c may be positioned on the first light emitting layer 324a.

The second stack 325 includes a second emitting layer 325a. The second emitting layer 325a may include, for example, a host material and a dopant.

The second stack 325 may further include a second hole transport layer 325b and a second electron transport layer 324b.

The second hole transport layer 325b may be positioned between the second light emitting layer 325a and one of the first electrode 321 and the second electrode 323 as an anode electrode. The second electron transport layer 325c may be positioned between the second light emitting layer 324a and one of the first electrode 321 and the second electrode 323 as a cathode electrode. For example, when the first electrode 321 is the anode electrode and the second electrode 323 is the cathode electrode, the second hole transport layer 325b may be positioned on the second electrode 321, the second light emitting layer 325a may be positioned on the second hole transport layer 325b, and the second electron transport layer 324c may be positioned on the second light emitting layer 325a.

Since the first stack 324 and the second stack 325 are configured as described above, holes and electrons transmitted from the first electrode 321 and the second electrode 323 are recombined with each other in the first and second light emitting layers 324a and 232 so that tight may be emitted from by recombination the first and second light emitting layers 324a and 232.

The charge generating layer 326 is formed between a plurality of light emitting layers to smoothly distribute charges so that it may increase the current efficiency of the light emitting layer. Accordingly, the charge generating layer 326 is positioned between the first stack 324 including the first light emitting layer 324a and the second stack 325 including the second light emitting layer 325a.

The charge generating layer 326 may include a p-type charge generating layer and an n-type charge generating layer in order to smoothly distribute charges. For example, the first layer 326a may be a p-type charge generating layer and the second layer 326b may be an n-type charge generating layer. When the first electrode 321 is the anode electrode and the second electrode 323 is the cathode electrode, the p-type charge generating layer may be located on the cathode electrode side and the n-type charge generating layer may be located on the anode side. For example, the first layer 326a may be positioned between the second layer 326b and the second electrode 323 which is a cathode electrode.

Although FIG. 3 shows the tandem organic electric element including two stacks, the embodiment is not limited to the tandem organic electric element including two stacks, and includes tandem organic electric element including two or more stacks. When the organic electrical element 320 further includes a stack, a charge generating layer may be additionally positioned between the additionally included stack and one of the adjacent first stack 324 and the second stack 325.

The organic electric element 320 may include a hole injection layer 327. The hole injection layer 327 may be positioned between the first electrode 321 as an anode electrode and the first light emitting layer 324a. For example, the hole injection layer 327 may be positioned between the first electrode 321 as an anode electrode and the first hole transport layer 324b.

Although not illustrated in FIG. 3, the organic electric element 320 may further include an electron injection layer. For example, the electron injection layer may be positioned between the second electrode 323 as a cathode electrode, and the second electron transport layer 325c.

In another example, each of the first stack 324 and the second stack 325 may further include one or more of a hole injection layer and an electron injection layer. Within each stack, the hole injection layer may be located between the light emitting layer and the anode electrode, and an electron injection layer may be located between the light emitting layer and the cathode electrode.

The first layer 326a includes the first compound. The first hole transport layer 324b may include the first compound, and the second hole transport layer 325b may also include the first compound. Further, the hole injection layer may also include the first compound. The first compound included in each layer may be the same as each other or may be different from each other as long as the requirements for the first compound described later are met.

The first compound is represented by one or more of the following chemical formula 1 and chemical formula 2.

[chemical formula 1]

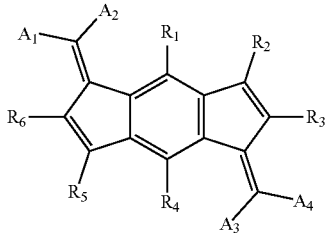

[chemical formula 2]

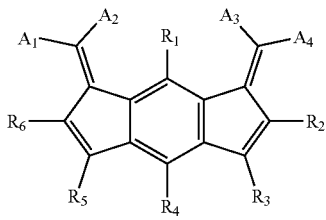

Hereinafter, chemical formula 1 and chemical formula 2 will be described.

$R_1$ to $R_6$, which are same or different, are each independently one selected from the group consisting of a hydrogen; a deuterium; a tritium; a halogen; a cyano group; a nitro group; a $C_6$-$C_{60}$ aryl group; a fluorenyl group; a $C_2$-$C_{60}$ hetero ring group containing at least one hetero atom from O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; a $C_3$-$C_{60}$ alkylsilyl group; a $C_{18}$-$C_{60}$ arylsilyl group; and a $C_8$-$C_{60}$ alkylarylsilyl group, and one or more of $R_1$ to $R_6$ is the cyano group.

When $R_1$ to $R_6$ are the aryl groups, they may be each independently a $C_6$-$C_{60}$ aryl group, a $C_6$-$C_{30}$ aryl group or a $C_6$-$C_{12}$ aryl group.

$A_1$ to $A_4$, which may be the same or different, are each independently one selected from the group consisting of a hydrogen; a deuterium; a tritium; a halogen; a cyano group; a nitro group; a $C_6$-$C_{60}$ aryl group; a fluorenyl group; a $C_2$-$C_{60}$ hetero ring group containing at least one hetero atom from O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; a $C_3$-$C_{60}$ alkylsilyl group; a $C_{18}$-$C_{60}$ arylsilyl group; and a $C_8$-$C_{60}$ alkylarylsilyl group.

In $R_1$ to $R_6$ and $A_1$ to $A_4$ of the chemical formula 1 and the chemical formula 2, the aryl group, the fluorenyl group, the hetero ring group, the fused ring group, the alkyl group, the alkenyl group, the alkynyl group, the alkoxy group, the aryloxy group, the alkylsilyl group, the arylsilyl group and the alkylarylsilyl group may each be further substituted with at least one substituent selected from the group consisting of a deuterium; a nitro group; a cyano group; a halogen; an amino group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with the deuterium; a fluorenyl group; a $C_2$-$C_{20}$ hetero ring group; a $C_3$-$C_{60}$ alkylsilyl group; a $C_{18}$-$C_{60}$ arylsilyl group; and a $C_8$-$C_{60}$ alkylarylsilyl group.

When the first compound is represented by one or more of the chemical formula 1 and the chemical formula 2, for example, the first layer includes one compound (A) represented by chemical formula 1 and one compound (B) represented by chemical formula 2, it means that all the two compounds (A, B) are included in the first compound.

The first layer 326b includes a second compound. The second compound is represented by the following chemical formula 3.

[chemical formula 3]

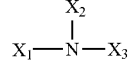

Hereinafter, chemical formula 3 will be described.

$X_1$ to $X_3$, which may be the same or different, are each independently one selected from the group consisting of a $C_6$-$C_{60}$ aryl group; a fluorenyl group; a $C_2$-$C_{60}$ hetero ring group containing at least one hetero atom from O, N, S, Si and P; a fused ring group of a $C_3$-$C_{60}$ aliphatic ring and a $C_6$-$C_{60}$ aromatic ring, or is represented by one of the following formulas 3-1 to 3-5.

In $X_1$ to $X_3$ of the chemical formula 3, the aryl group, the fluorenyl group, the hetero ring group, and the fused ring group may each be further substituted with at least one substituent selected from the group consisting of a deuterium; a nitro group; a cyano group; a halogen; an amino group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with the deuterium; a fluorenyl group; a $C_2$-$C_{20}$ hetero ring group; a $C_3$-$C_{60}$ alkylsilyl group; a $C_{18}$-$C_{60}$ arylsilyl group; and a $C_8$-$C_{60}$ alkylarylsilyl group.

[chemical formula 3-1]

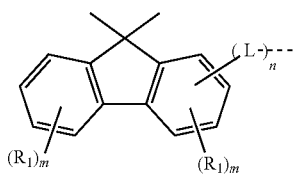

[chemical formula 3-2]

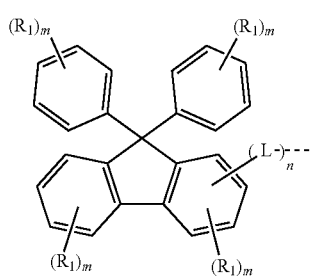

[chemical formula 3-3]

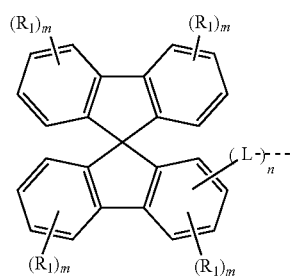

[chemical formula 3-4]

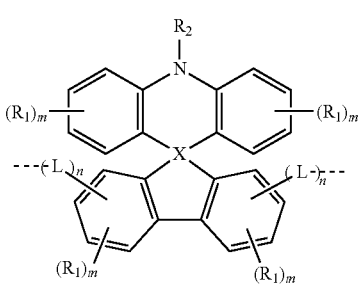

[chemical formula 3-5]

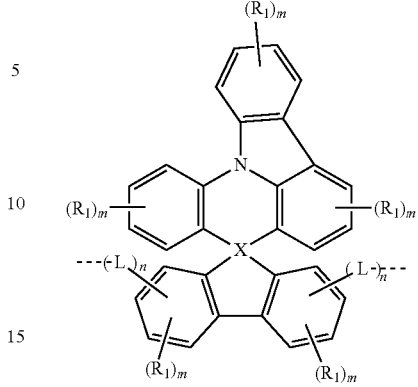

Hereinafter, the chemical formulas 3-1 to 3-5 will be described.

m and n are each independently an integer of 0 to 3.

$R_1$ is each independently one selected from the group consisting of a hydrogen; a deuterium; a tritium; a halogen; a cyano group; a nitro group; a $C_6$-$C_{60}$ aryl group; a fluorenyl group; a $C_2$-$C_{60}$ hetero ring group containing at least one hetero atom from O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; a $C_3$-$C_{60}$ alkylsilyl group; a $C_{18}$-$C_{60}$ arylsilyl group; and a $C_8$-$C_{60}$ alkylarylsilyl group.

When $R_1$ is the aryl groups, it may be each independently a $C_6$-$C_{60}$ aryl group, a $C_6$-$C_{30}$ aryl group or a $C_6$-$C_{12}$ aryl group.

When $R_1$ is the alkyl group, it may be each independently a $C_1$-$C_{30}$ alkyl group, a $C_6$-$C_{20}$ alkyl group or a $C_6$-$C_{12}$ alkyl group.

L is one selected from the group consisting of a $C_6$-$C_{60}$ arylene group; a fluorylene group; a $C_2$-$C_{60}$ divalent hetero ring group containing at least one heteroatom from O, N, S, Si and P; a divalent fused ring group of a $C_3$-$C_{60}$ aliphatic ring and a $C_6$-$C_{60}$ aromatic ring.

In the chemical formulas 3-1 to 3-5, a portion of a broken line connected to L represents a position where X1 to X3 are bonded to N in the chemical formula 3, or a position where the hydrogen is bonded. For example, in the chemical formulas 3-1 to 3-3, the portion of the broken line connected to L may be a position to be bonded to N of the chemical formula 3. In the case of the chemical formulas 3-4 and 3-5, any one of the broken lines may be bonded to N of the chemical formula 3, and the other one of the broken lines may be bonded to the hydrogen.

In $R_1$ and L of the chemical formulas 3-1 to 3-5, the aryl group, the fluorenyl group, the hetero ring group, the fused ring group, the alkyl group, the alkenyl group, the alkynyl group, the alkoxy group, the aryloxy group, the alkylsilyl group, the arylsilyl group, the alkylarylsilyl group, the arylene group, the fluorylene group, the divalent fused ring group, the divalent fused ring group may each be further substituted with at least one substituent selected from the group consisting of a deuterium; a nitro group; a cyano group; a halogen; an amino group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with the deuterium; a fluorenyl group; a $C_2$-$C_{20}$ hetero ring group; a $C_3$-$C_{60}$ alkylsilyl group; a $C_{18}$-$C_{60}$ arylsilyl group; and a $C_8$-$C_{60}$ alkylarylsilyl group.

Since the organic electric element 320 includes the first layer 326a including the first compound and the second compound, it can have high efficiency or long life.

The second layer 326b includes a third compound. The third compound may be represented by the following chemical formula 4.

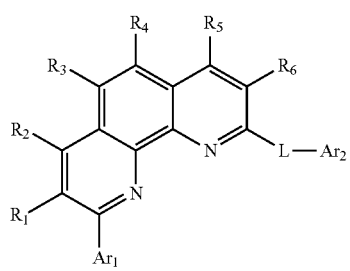

[chemical formula 4]

Hereinafter, chemical formula 4 will be described.

$R_1$ to $R_6$, which are same or different, are each independently one selected from the group consisting of a hydrogen; a deuterium; a tritium; a halogen; a cyano group; a nitro group; a $C_6$-$C_{60}$ aryl group; a fluorenyl group; a $C_2$-$C_{60}$ hetero ring group containing at least one hetero atom from O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; a $C_3$-$C_{60}$ alkylsilyl group; a $C_{18}$-$C_{60}$ arylsilyl group; and a $C_8$-$C_{60}$ alkylarylsilyl group, and one or more of $R_1$ to $R_6$ is the cyano group.

When $R_1$ to $R_6$ are the aryl groups, they may be each independently a $C_6$-$C_{60}$ aryl group, a $C_6$-$C_{30}$ aryl group or a $C_6$-$C_{12}$ aryl group.

When $R_1$ to $R_6$ are the hetero ring group containing at least one hetero atom from O, N, S, Si and P, they may be each independently the $C_6$-$C_{60}$ hetero ring group, the $C_6$-$C_{50}$ hetero ring group or the $C_6$-$C_{40}$ hetero ring group.

$Ar_1$ and $Ar_2$, which are same or different, are each independently one selected from the group consisting of a hydrogen; a deuterium; a tritium; a halogen; a cyano group; a nitro group; a $C_6$-$C_{60}$ aryl group; a fluorenyl group; a $C_2$-$C_{60}$ hetero ring group containing at least one hetero atom from O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; a $C_3$-$C_{60}$ alkylsilyl group; a $C_{18}$-$C_{60}$ arylsilyl group; and a $C_8$-$C_{60}$ alkylarylsilyl group, and one or more of $R_1$ to $R_6$ is the cyano group.

When $Ar_1$ to $Ar_6$ are the aryl groups, they may be each independently a $C_6$-$C_{60}$ aryl group, a $C_6$-$C_{50}$ aryl group or a $C_6$-$C_{40}$ aryl group.

When $Ar_1$ to $Ar_6$ are the hetero ring group containing at least one hetero atom from O, N, S, Si and P, they may be each independently the $C_6$-$C_{60}$ hetero ring group, the $C_6$-$C_{50}$ hetero ring group or the $C_6$-$C_{40}$ hetero ring group.

L is one selected from the group consisting of a $C_6$-$C_{60}$ arylene group; a fluorylene group; a $C_2$-$C_{60}$ divalent hetero ring group containing at least one heteroatom from O, N, S, Si and P; a divalent fused ring group of a $C_3$-$C_{60}$ aliphatic ring and a $C_6$-$C_{60}$ aromatic ring.

In $R_1$ to $R_6$, $Ar_1$, $Ar_2$ and L of the chemical formula 4, the aryl group, the fluorenyl group, the hetero ring group, the fused ring group, the alkyl group, the alkenyl group, the alkynyl group, the alkoxy group, the aryloxy group, the alkylsilyl group, the arylsilyl group, the alkylarylsilyl group, the arylene group, the fluorylene group, the divalent fused ring group, the divalent fused ring group may each be further substituted with at least one substituent selected from the group consisting of a deuterium; a nitro group; a cyano group; a halogen; an amino group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with the deuterium; a fluorenyl group; a $C_2$-$C_{20}$ hetero ring group; a $C_3$-$C_{60}$ alkylsilyl group; a $C_{18}$-$C_{60}$ arylsilyl group; and a $C_8$-$C_{60}$ alkylarylsilyl group.

Since the organic electric element 320 includes the first layer 326a including the first compound and the second compound and the second layer 326b including the third compound, it can have high efficiency or long life.

The first chemical compound is represented by one or more of the following chemical formula 5 and chemical formula 6.

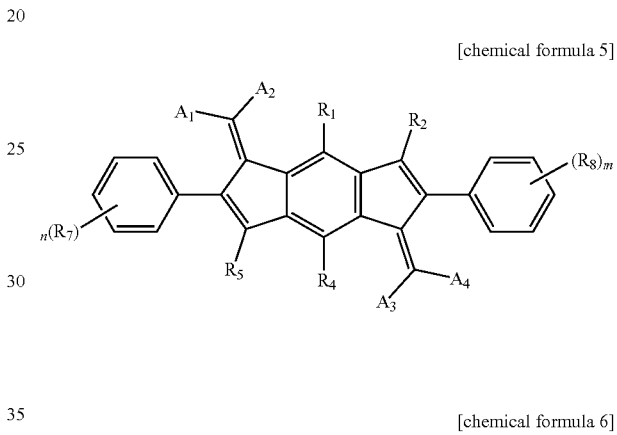

[chemical formula 5]

[chemical formula 6]

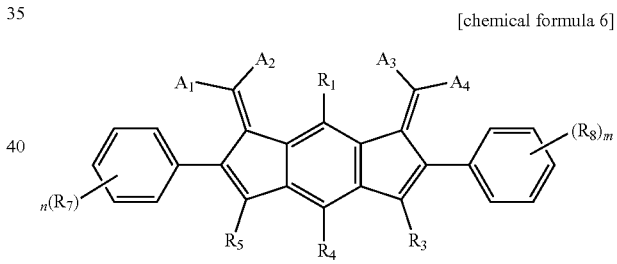

Hereafter, the chemical formula 5 and the chemical formula 6 will be described.

n and m are each independently an integer from 0 to 5.

$R_7$ to $R_8$, which may be the same or different, are each independently one selected from the group consisting of a deuterium; a tritium; a halogen; a cyano group; a $C_1$-$C_{50}$ alkyl group; and a $C_1$-$C_{30}$ alkoxy group.

When $R_7$ and $R_8$ are alkoxy groups, they may be, for example, a $C_1$-$C_{30}$ alkoxy group, a $C_1$-$C_{20}$ alkoxy group or a $C_1$-$C_{10}$ alkoxy group.

In $R_7$ and $R_8$ of the chemical formula 5 and the chemical formula 6, the alkyl group and the alkoxy group may each be further substituted with at least one substituent selected from the group consisting of a deuterium and a halogen.

When the first compound is represented by one or more of the chemical formula 5 and the chemical formula 6, for example, the first layer includes one compound (C) represented by chemical formula 5 and one compound (D) represented by chemical formula 6, it means that all the two compounds (C, D) are included in the first compound.

When the first layer 326a includes the first compound represented by one or more of the above chemical formulas 5 and 6, the organic electric element 320 may have high efficiency or long life.

The first chemical compound is represented by one or more of the following chemical formula 7 and formula 8.

[chemical formula 7]

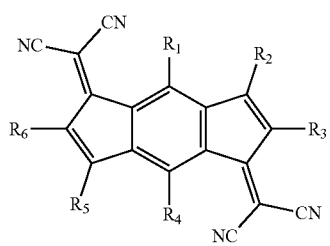

[chemical formula 8]

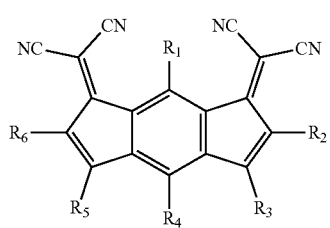

The chemical formula 7 and the chemical formula 8 will be described.

$R_1$ to $R_6$, which are same or different, are each independently one selected from the group consisting of a hydrogen; a deuterium; a tritium; a halogen; a cyano group; a nitro group; a $C_6$-$C_{60}$ aryl group; a fluorenyl group; a $C_2$-$C_{60}$ hetero ring group containing at least one hetero atom from O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; a $C_3$-$C_{60}$ alkylsilyl group; a $C_{18}$-$C_{60}$ arylsilyl group; and a $C_8$-$C_{60}$ alkylarylsilyl group, and one or more of $R_1$ to $R_6$ is the cyano group.

When $R_1$ to $R_6$ are the aryl groups, they may be each independently a $C_6$-$C_{60}$ aryl group, a $C_6$-$C_{30}$ aryl group or a $C_6$-$C_{12}$ aryl group.

In $R_1$ to $R_6$ of the chemical formula 7 and the chemical formula 8, the aryl group, the fluorenyl group, the hetero ring group, the fused ring group, the alkyl group, the alkenyl group, the alkynyl group, the alkoxy group, the aryloxy group, the alkylsilyl group, the arylsilyl group and the alkylarylsilyl group may each be further substituted with at least one substituent selected from the group consisting of a deuterium; a nitro group; a cyano group; a halogen; an amino group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with the deuterium; a fluorenyl group; a $C_2$-$C_{20}$ hetero ring group; a $C_3$-$C_{60}$ alkylsilyl group; a $C_{18}$-$C_{60}$ arylsilyl group; and a $C_8$-$C_{60}$ alkylarylsilyl group.

When the first compound is represented by one or more of the chemical formula 7 and the chemical formula 8, for example, the first layer includes one compound (E) represented by chemical formula 7 and one compound (F) represented by chemical formula 8, it means that all the two compounds (E, F) are included in the first compound.

When the first layer 326a includes the first compound represented by one or more of the above chemical formulas 7 and 8, the organic electric element 320 may have high efficiency or long life.

The first chemical compound may be one or more of the following chemical compounds.

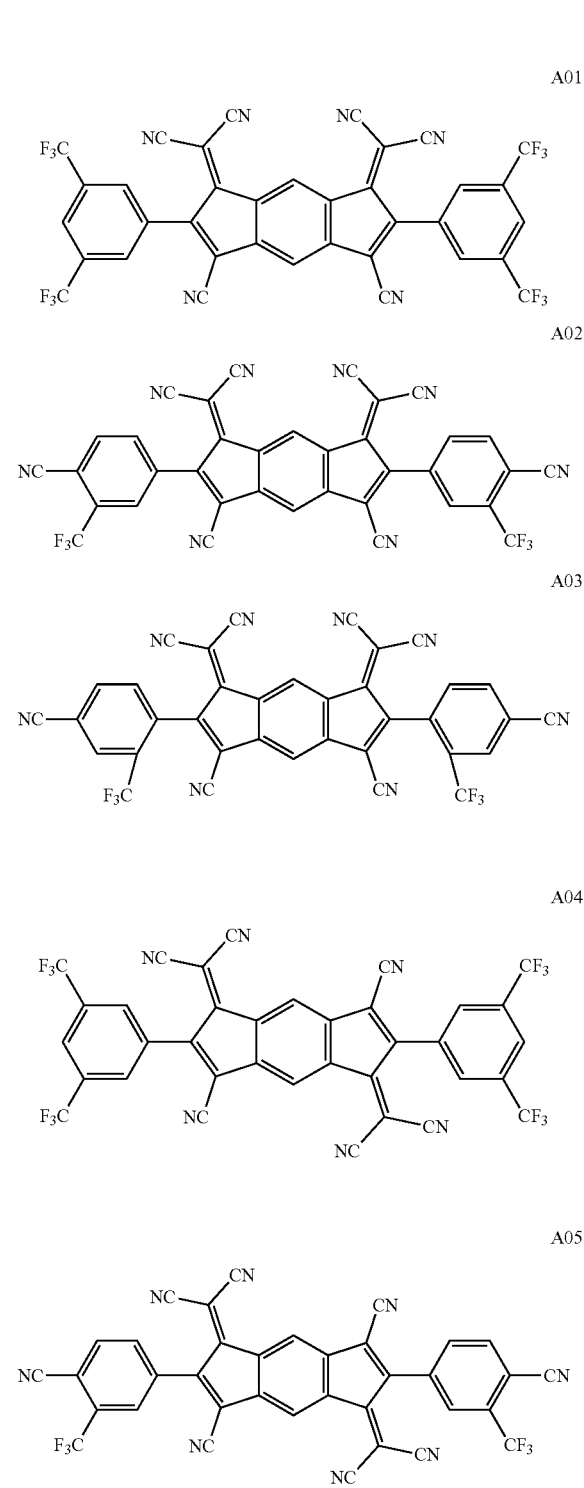

A06
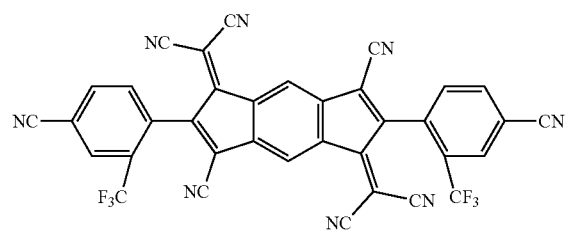
A07
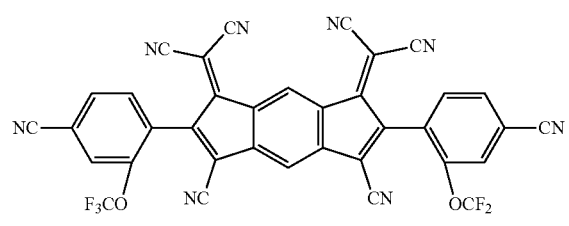
A08
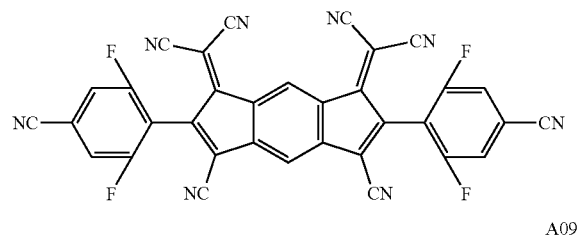
A09
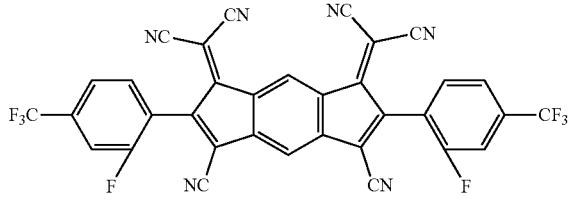
A10
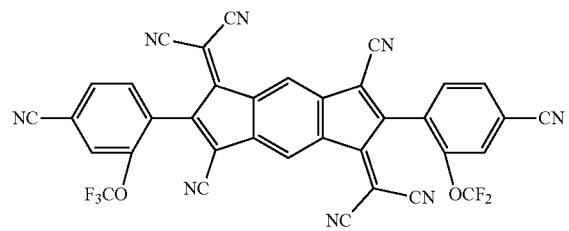
A11
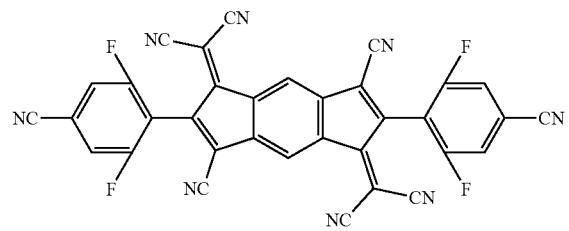
A12
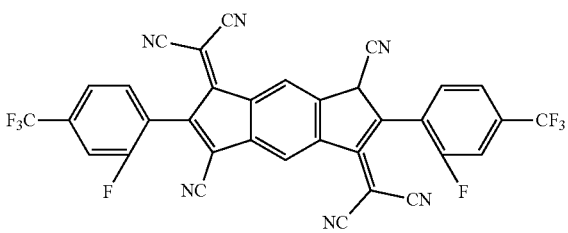
A13
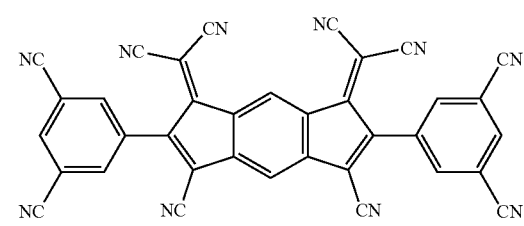
A14
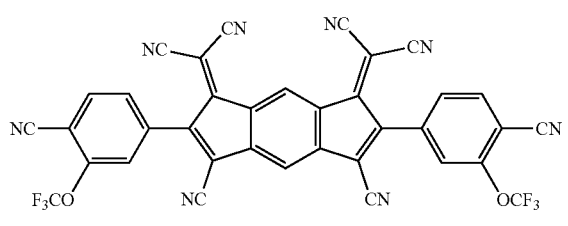
A15
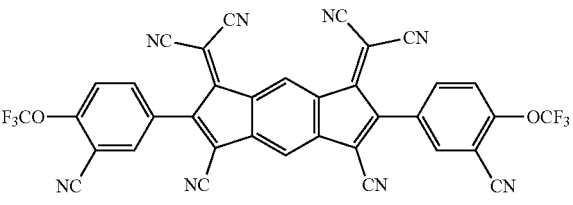
A16
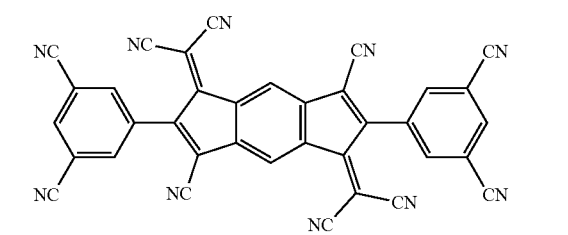
A17
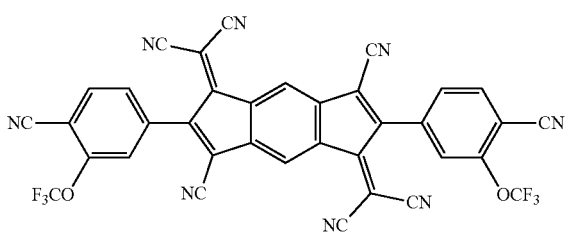

A18
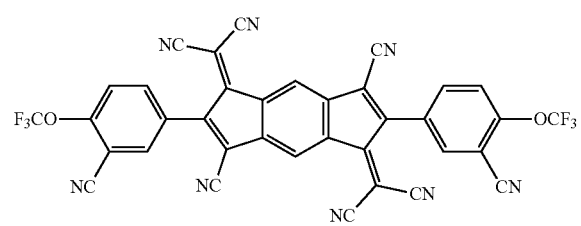
A19
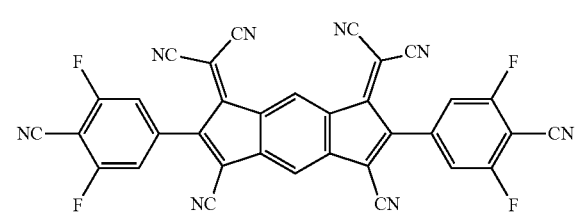
A20
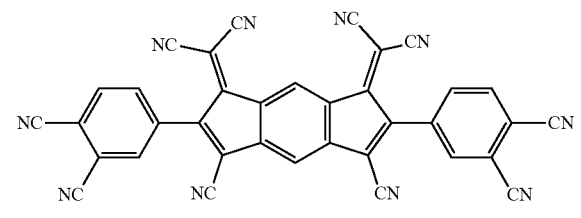
A21
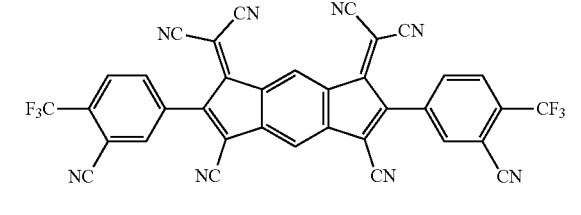
A22
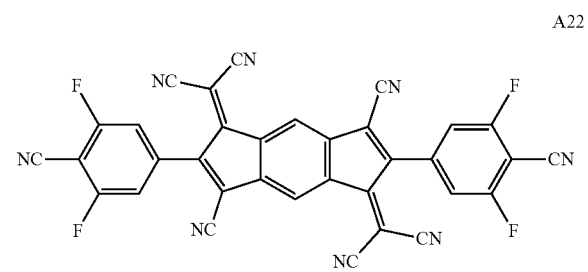
A23
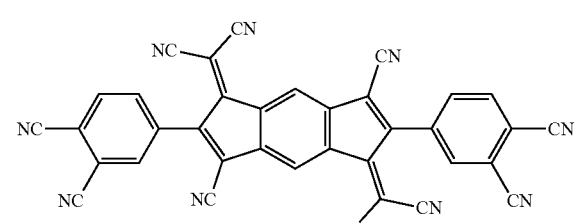
A24
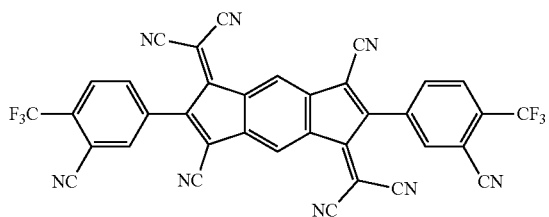
A25
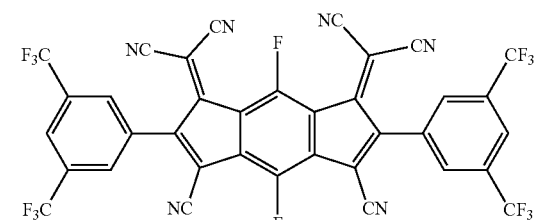
A26
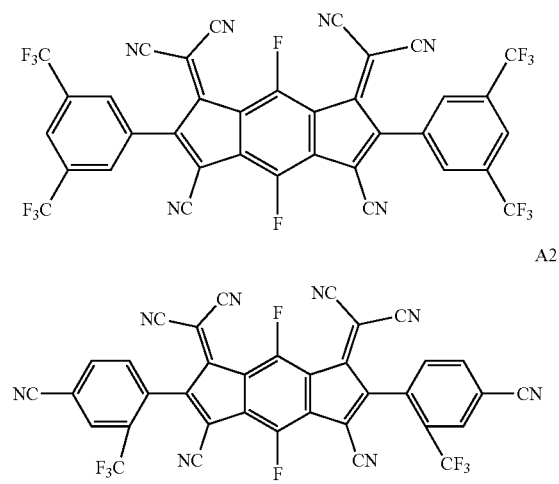
A27
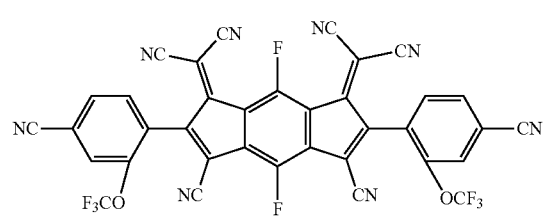
A28
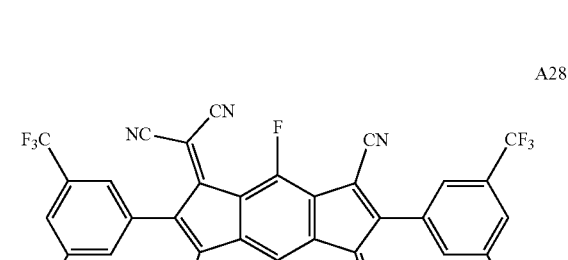
A29
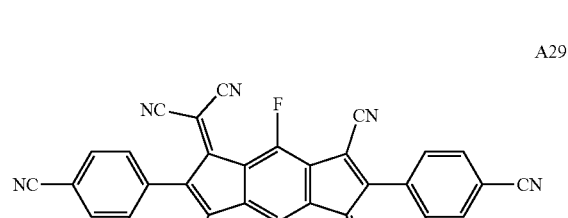
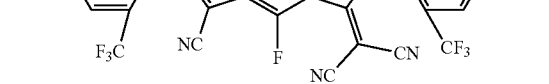

A30
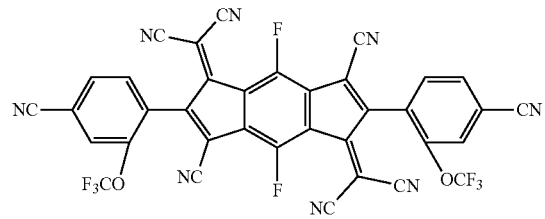
A31
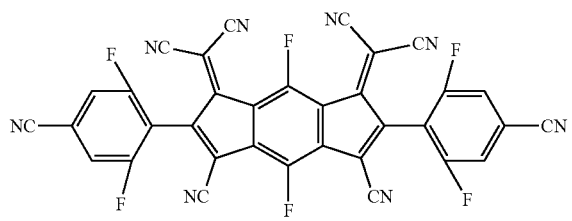
A32
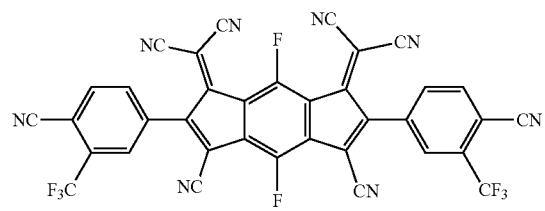
A33
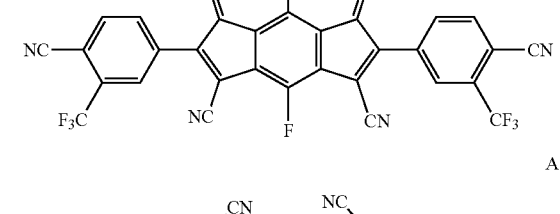
A34
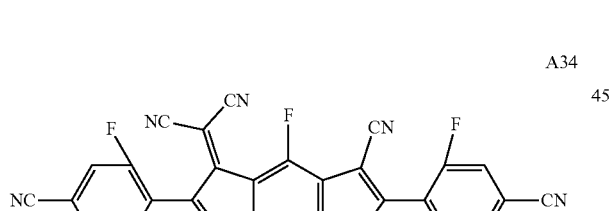
A35
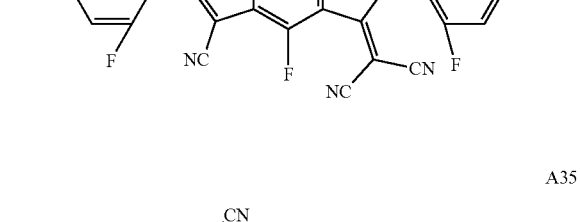
A36
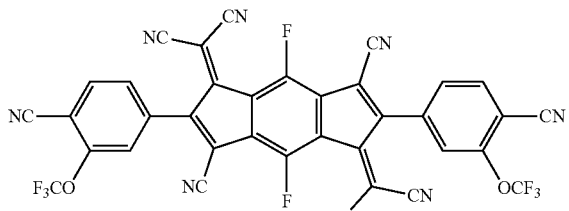
A37
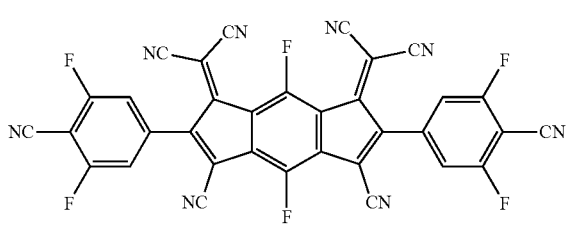
A38
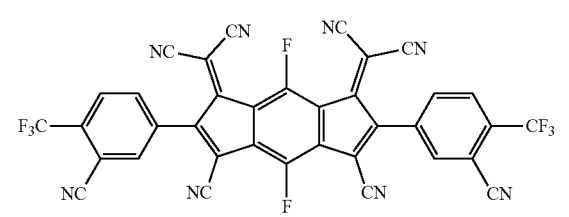
A39
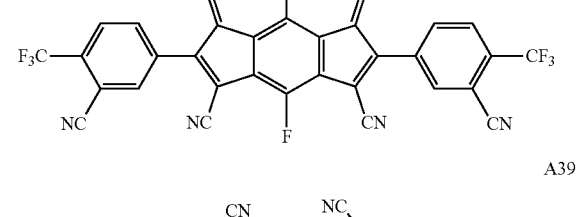
A40
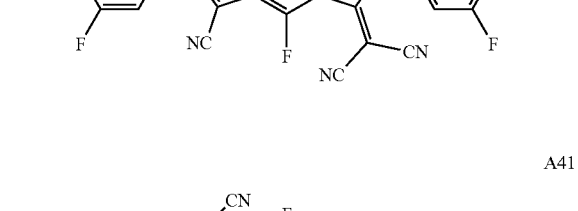
A41

A42

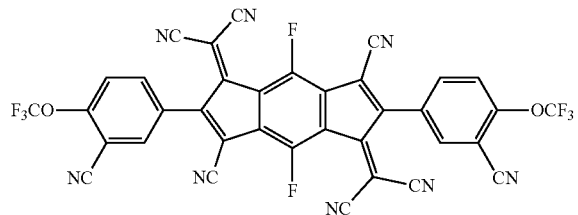

A43

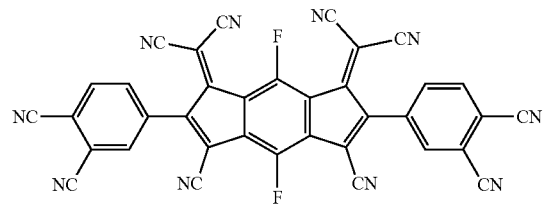

A44

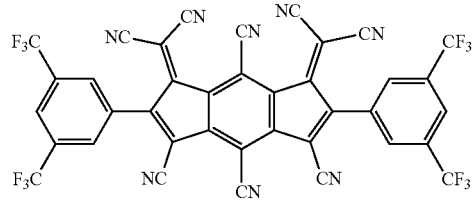

A45

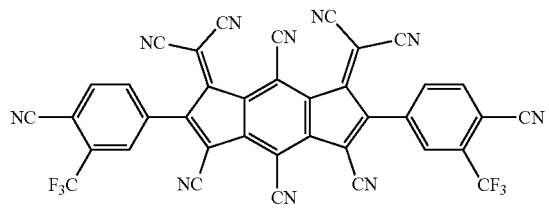

A46

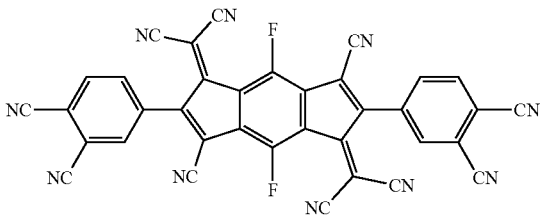

A47

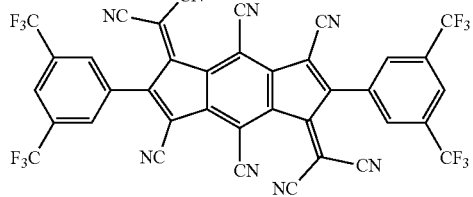

A48

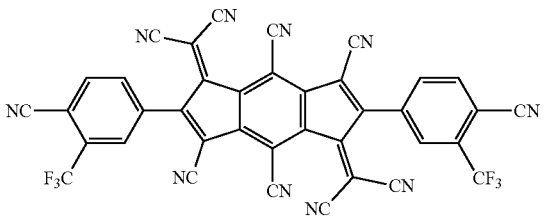

When the first layer 326a includes the first compound represented by one or more of the above chemical compound, the organic electric element 320 may have high efficiency or long life.

The second chemical compound is represented by one or more of the following chemical formula 9.

The second chemical compound may be one or more of the following chemical compounds.

D01

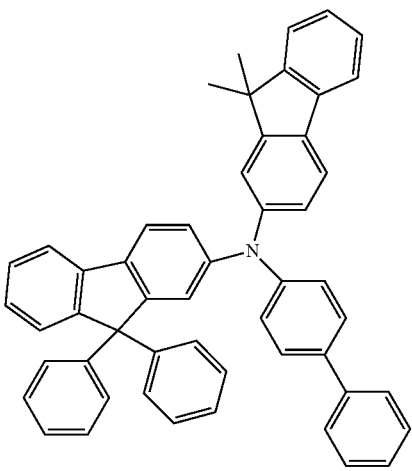

-continued
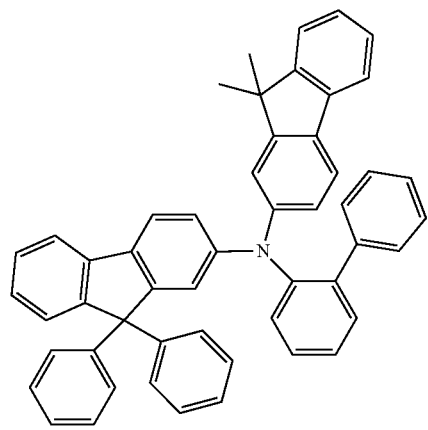
D02
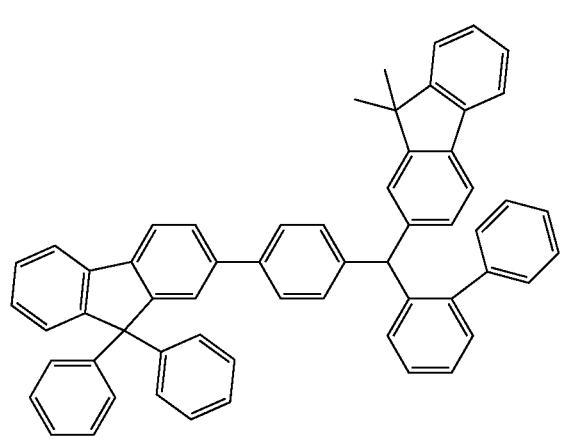
D03
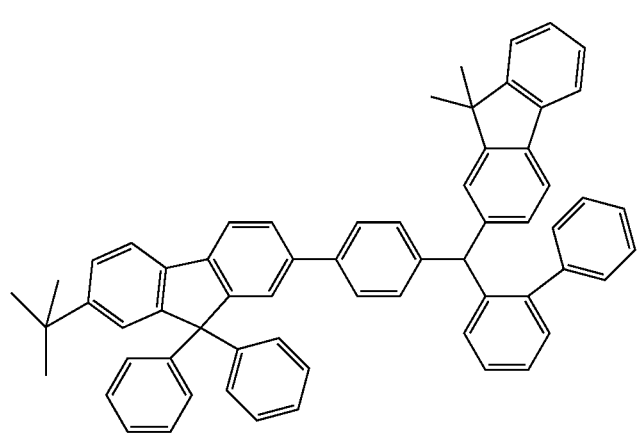
D04

-continued
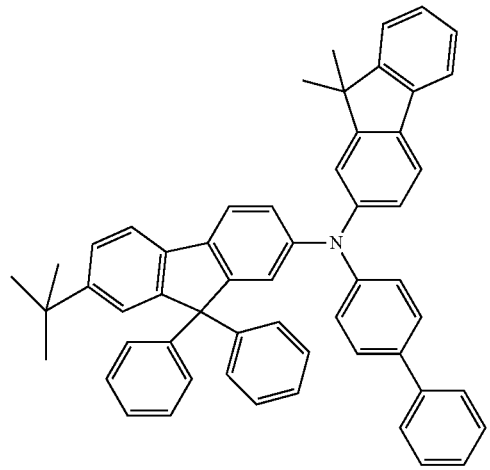
D05
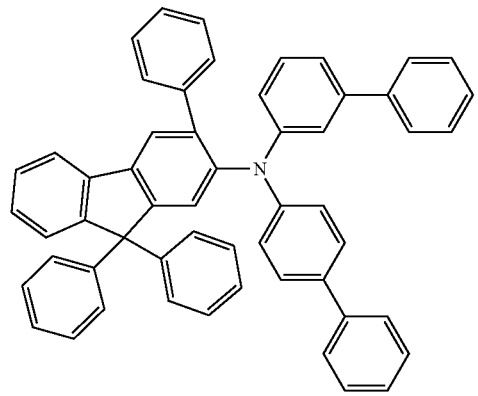
D06
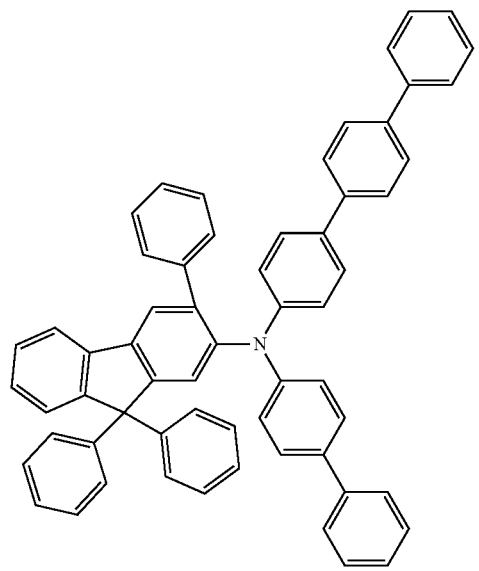
D07

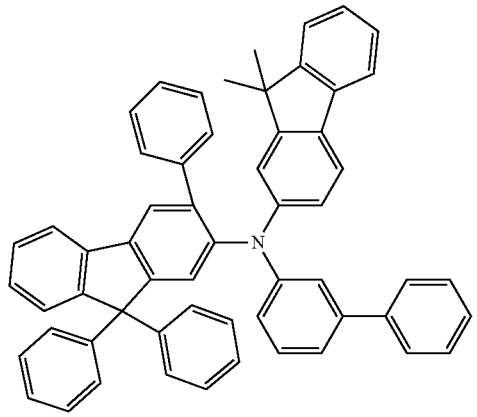
D08
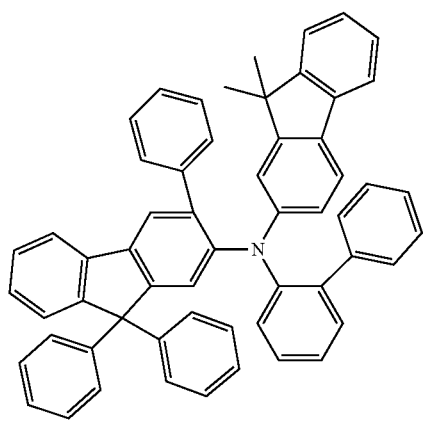
D09
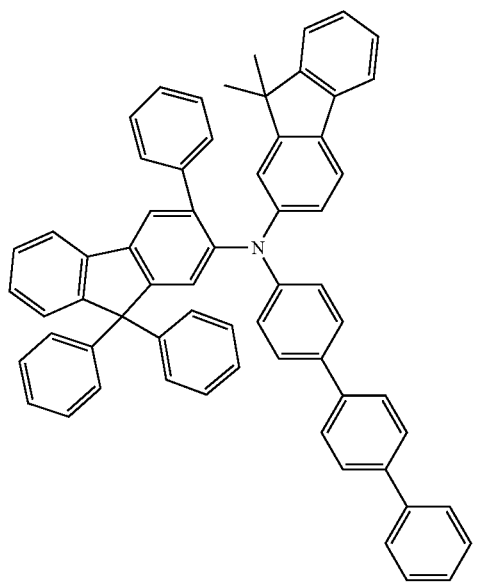
D10

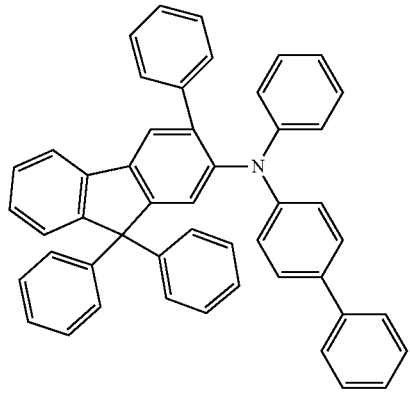
D11
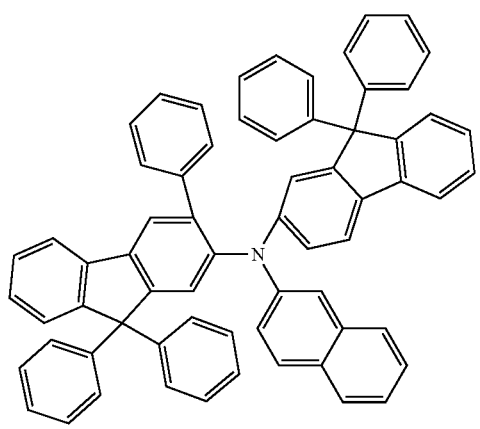
D12
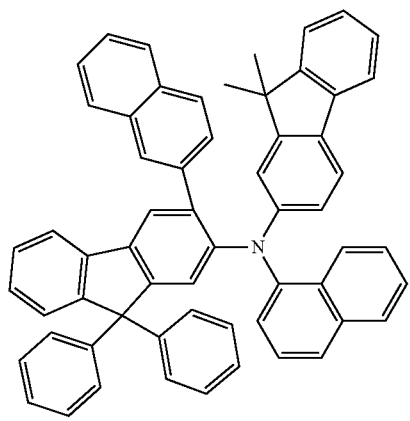
D13

-continued
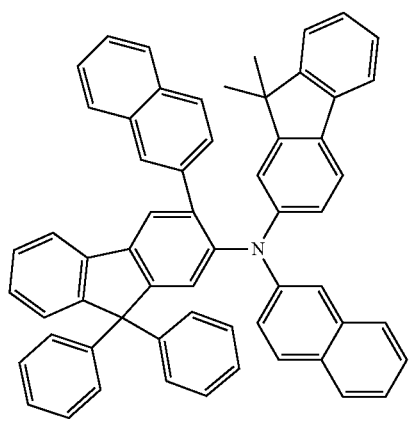
D14
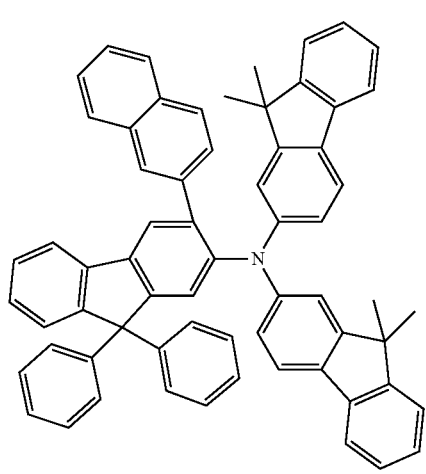
D15
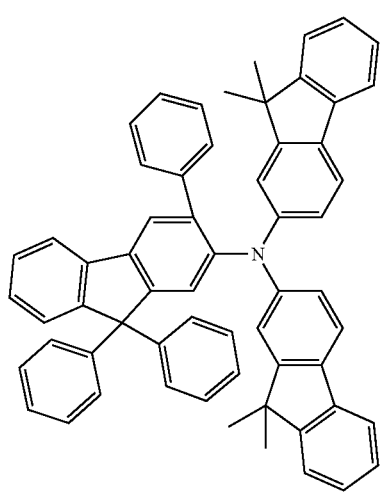
D16

D17
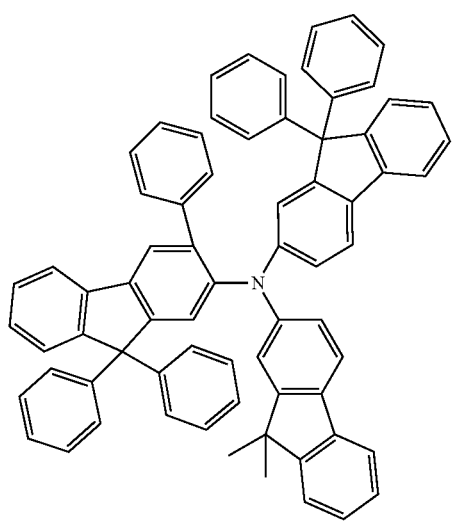
D18
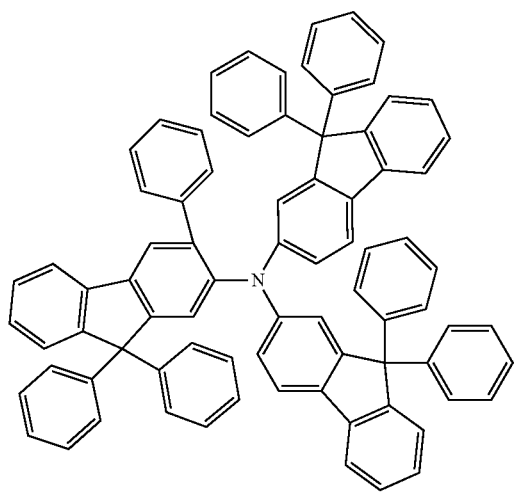
D19
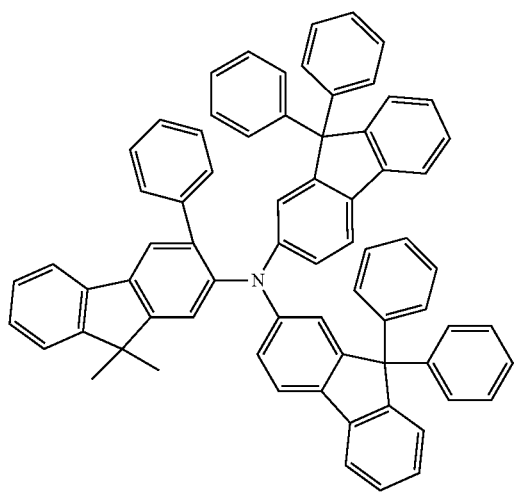

D20
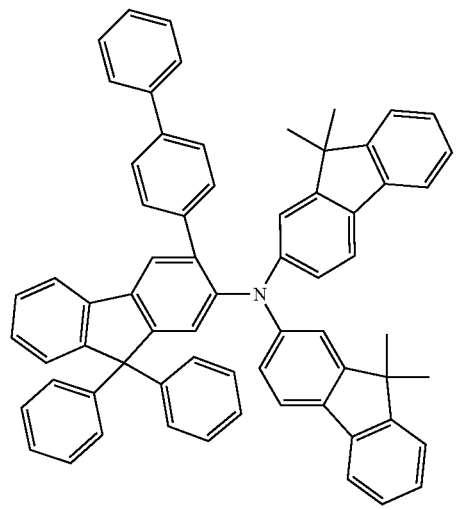
D21
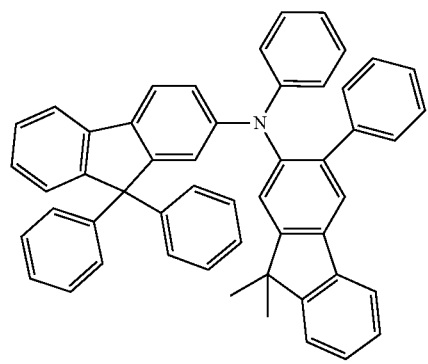
D22
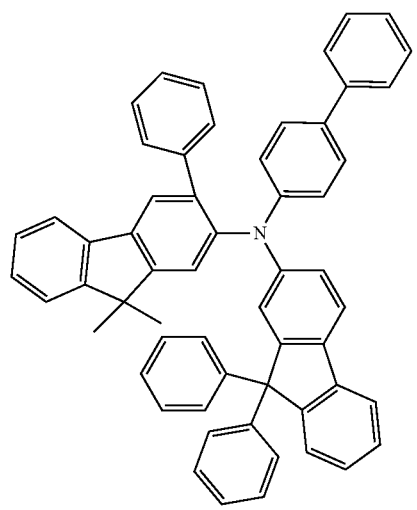

-continued
D23
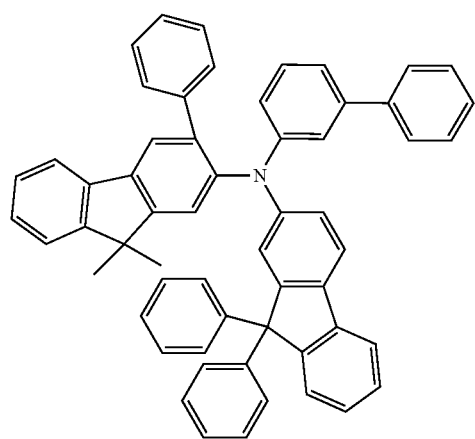
D24
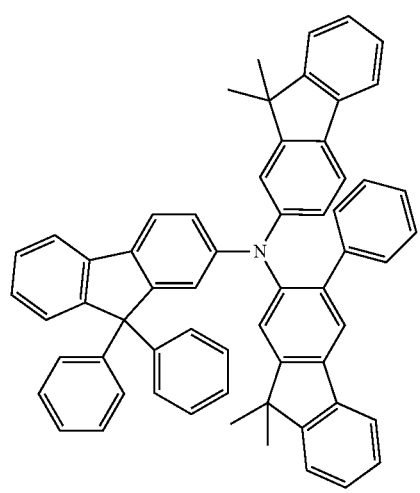
D25
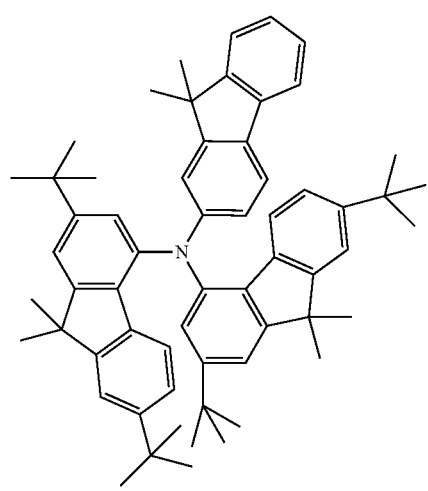

-continued
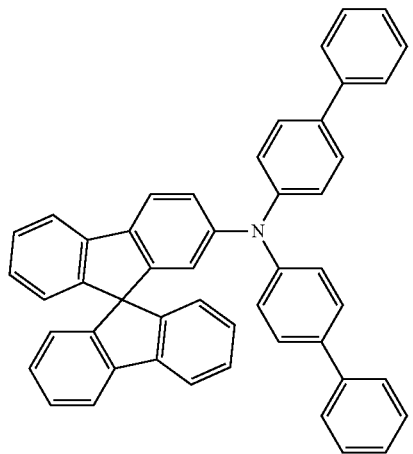
D26
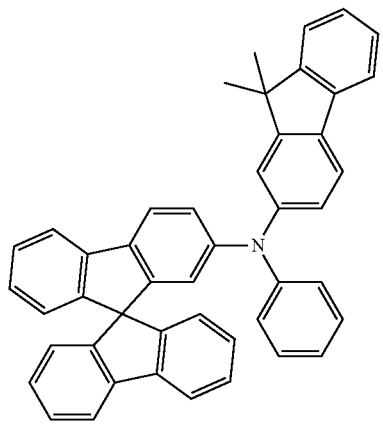
D27
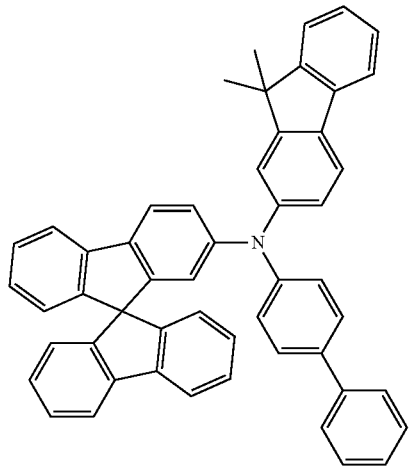
D28

-continued
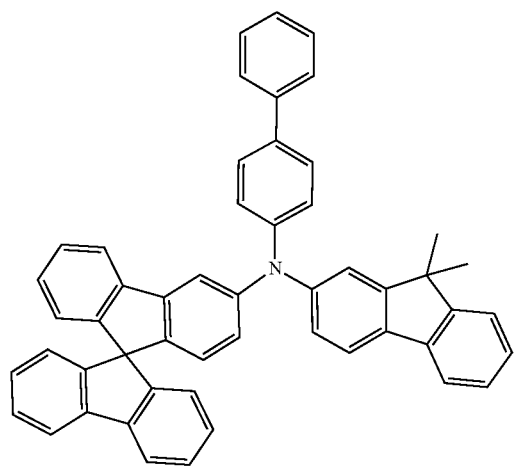
D29
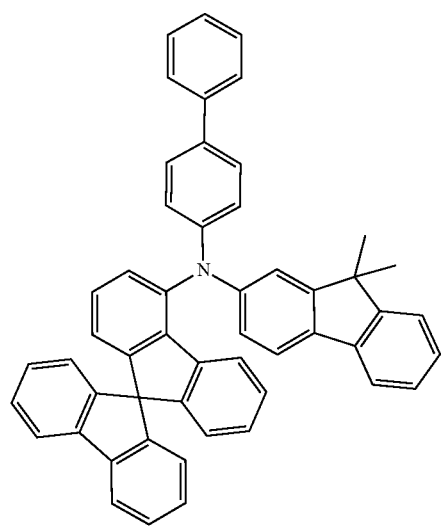
D30
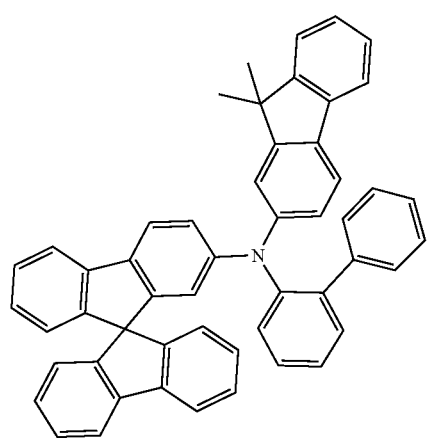
D31

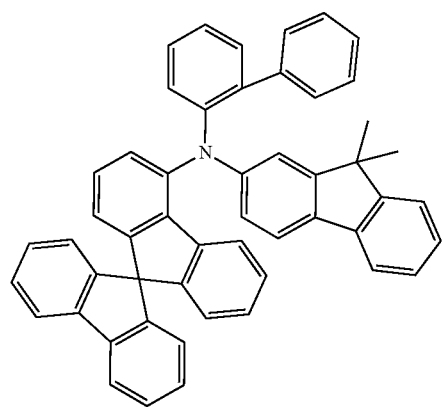
D32
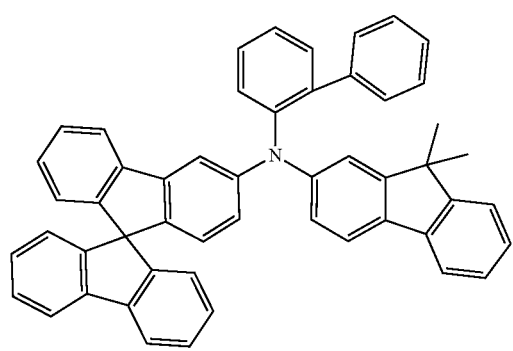
D33
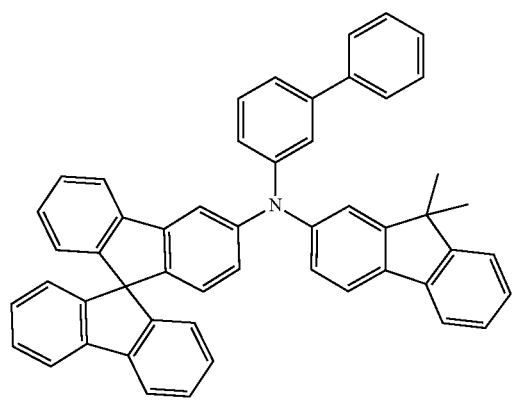
D34
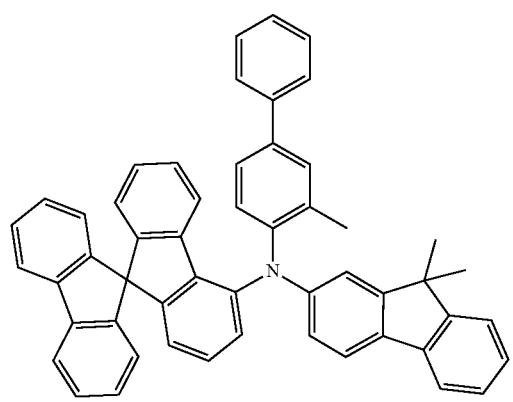
D35

-continued
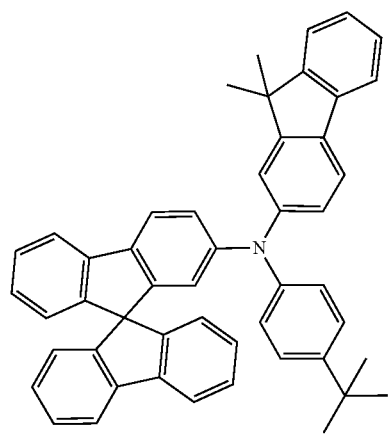
D36
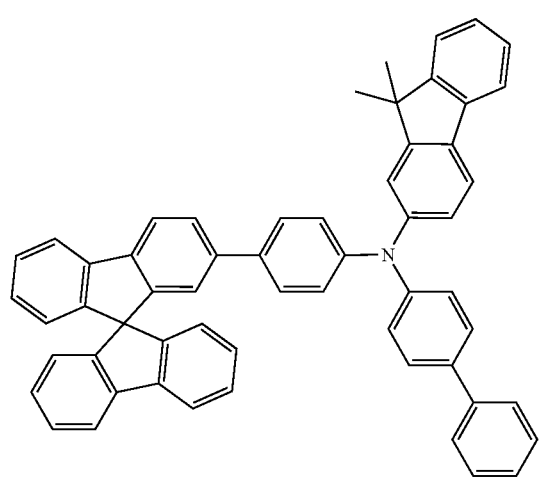
D37
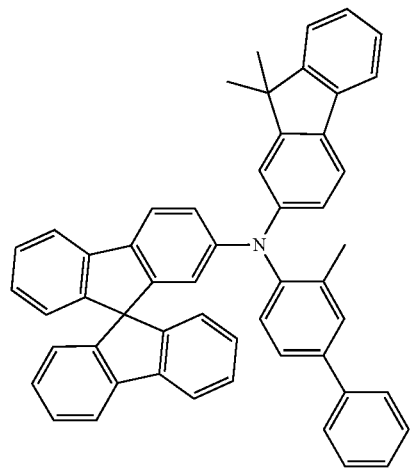
D38

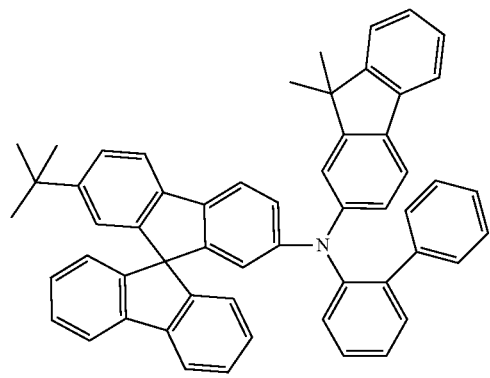
D39
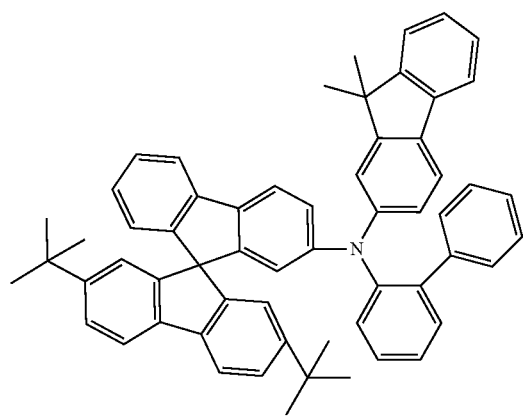
D40
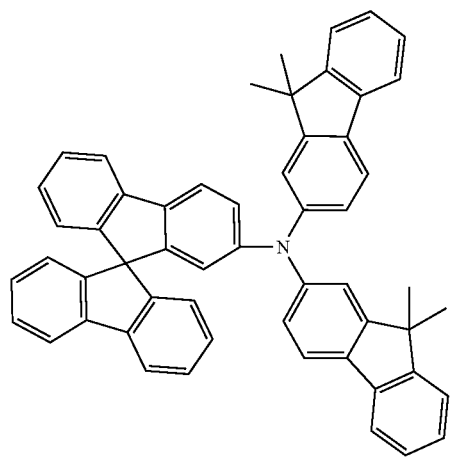
D41

-continued
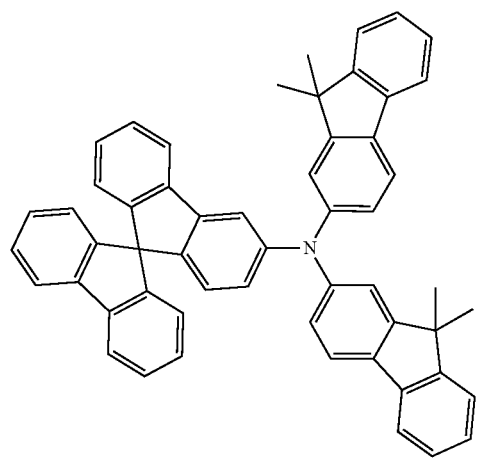
D42
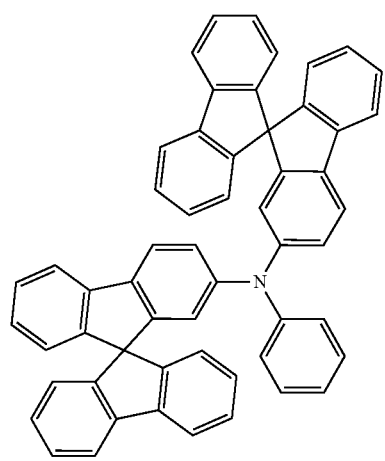
D43
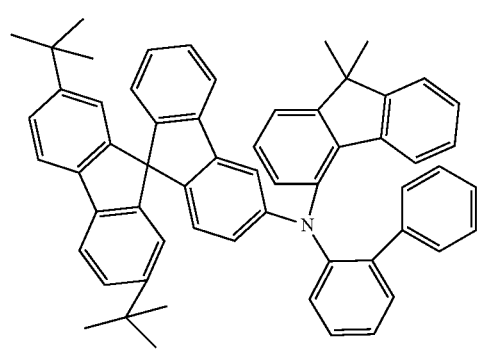
D44

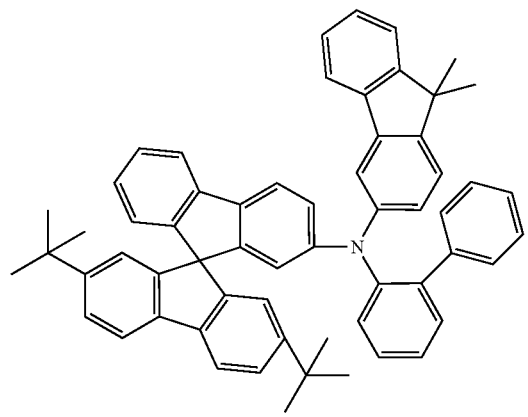
D45
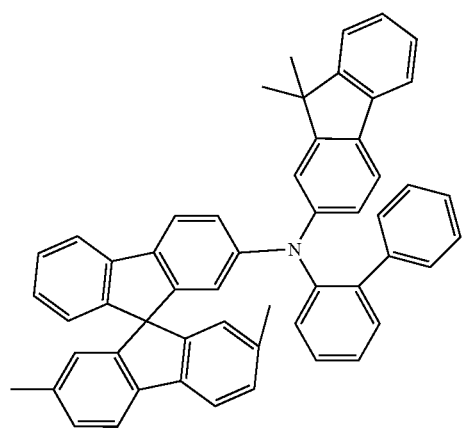
D46
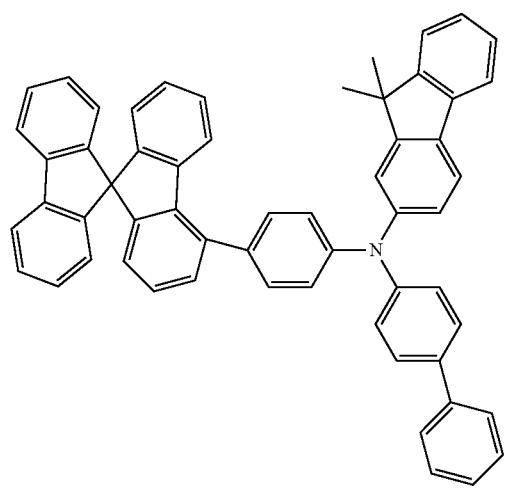
D47

D48
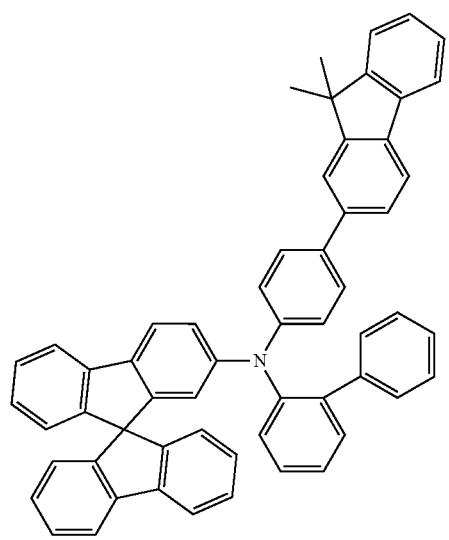
D49
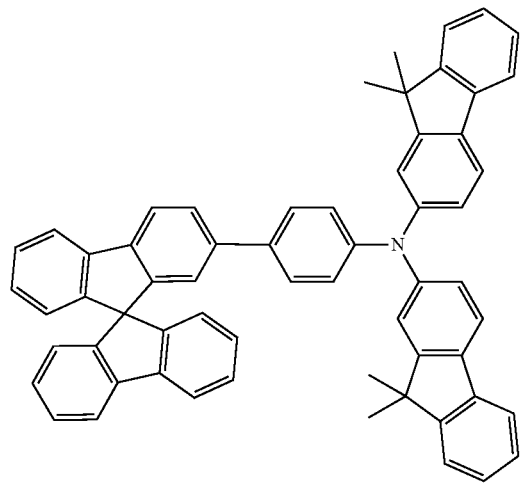
D50
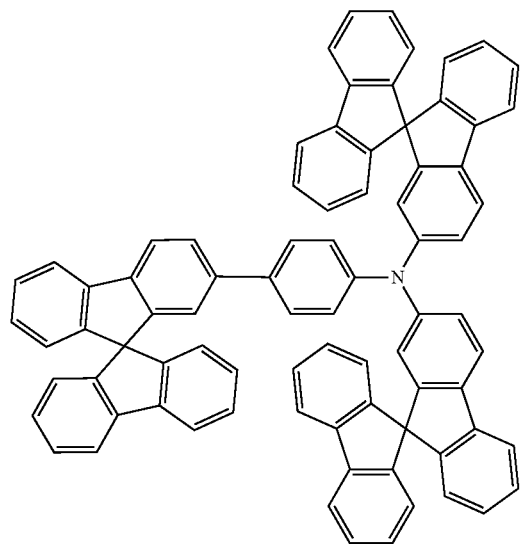

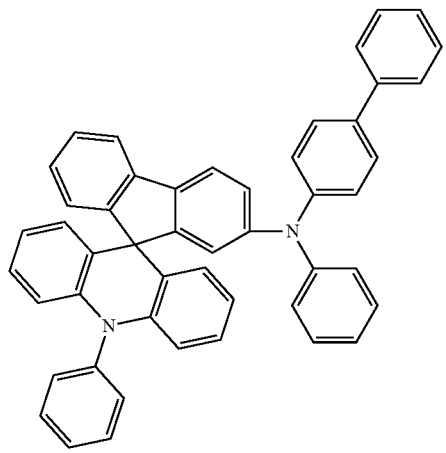
D51
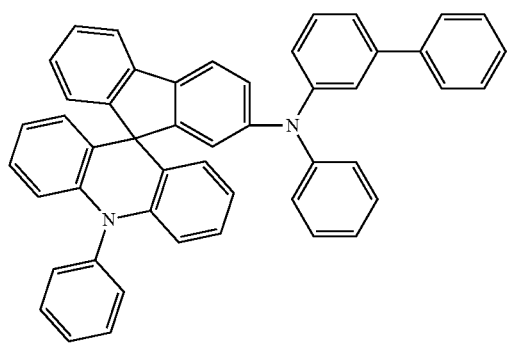
D52
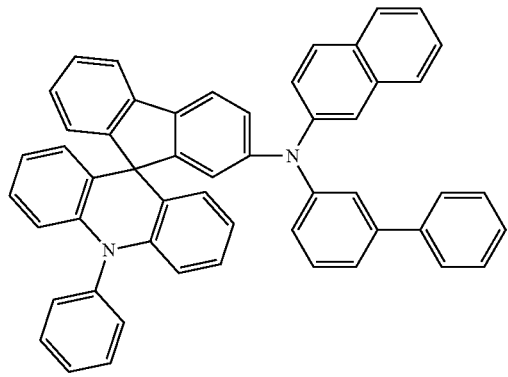
D53
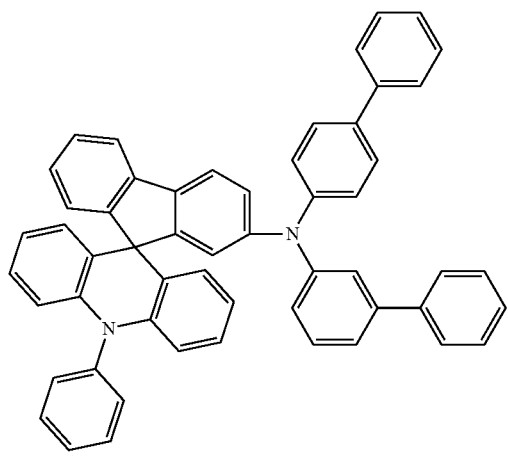
D54

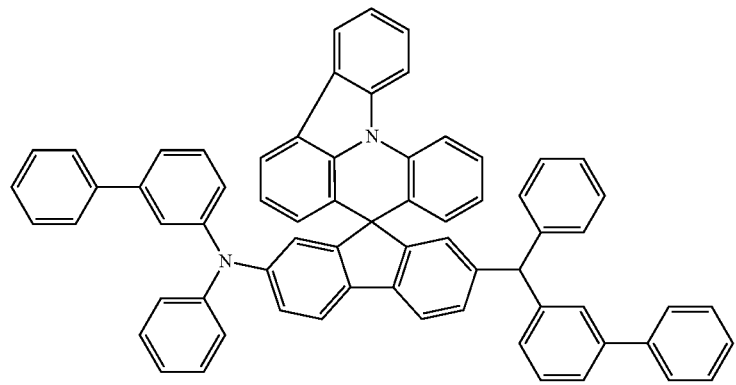
D55
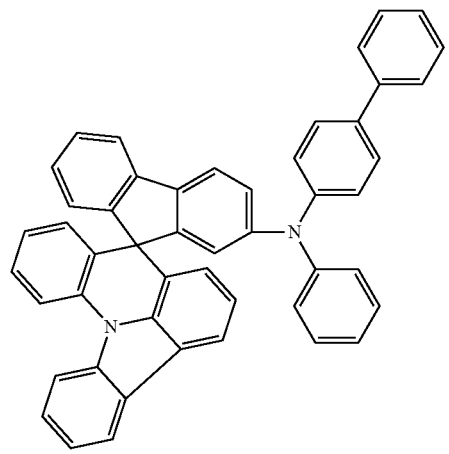
D56
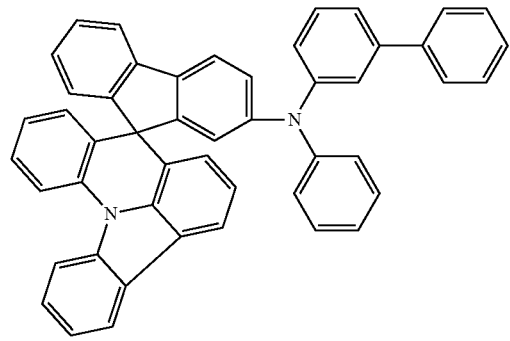
D57
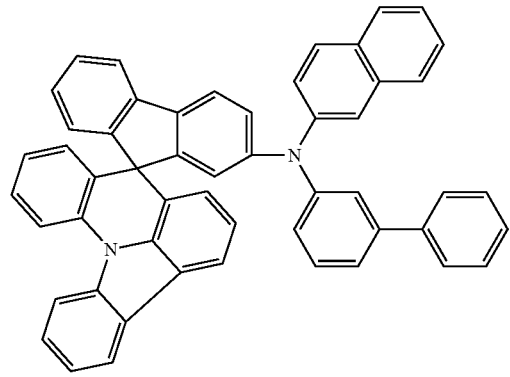
D58

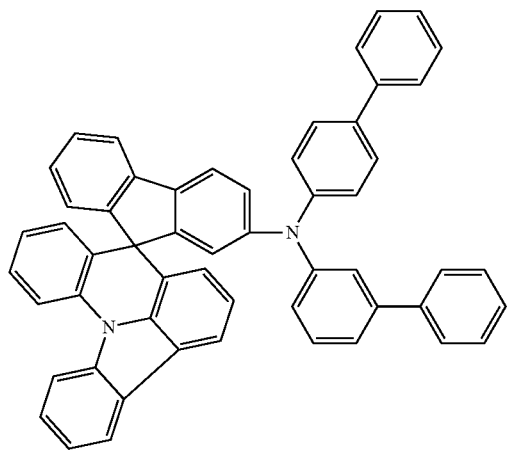
D59
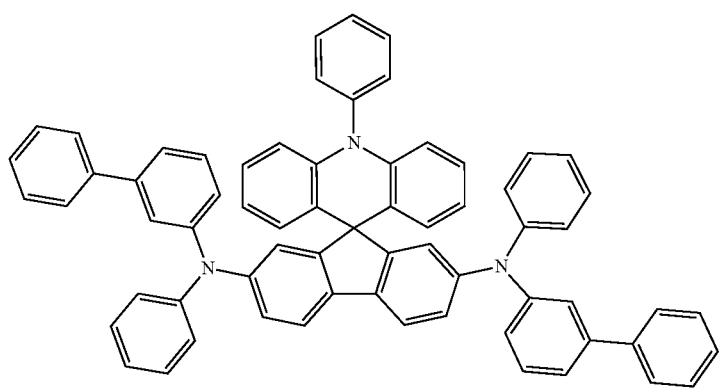
D60
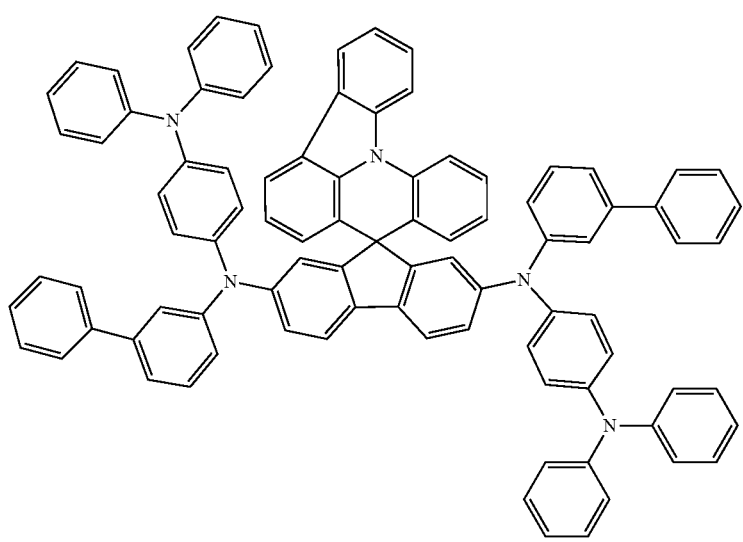
D61

D62
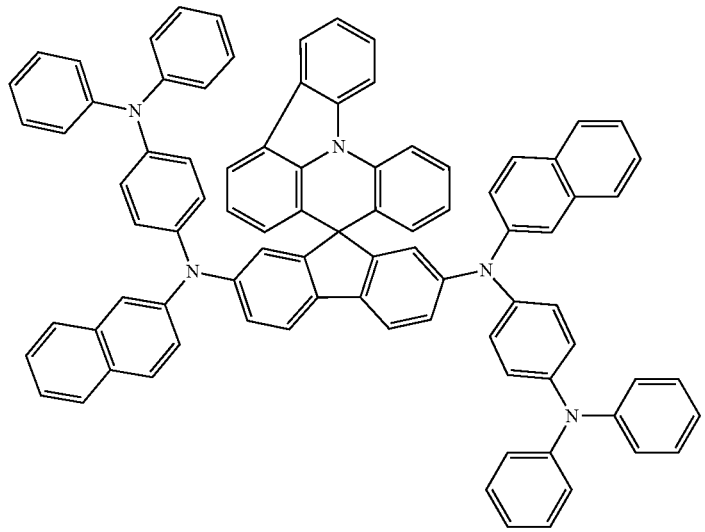
D63
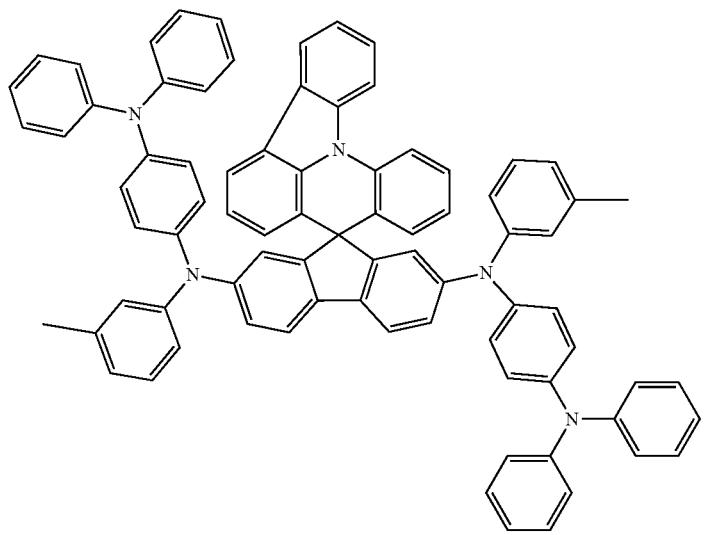
D64
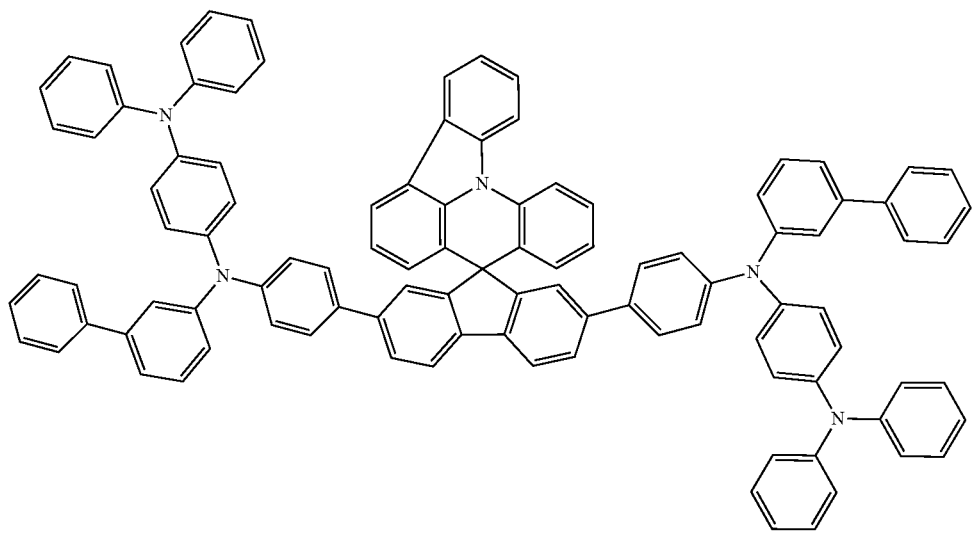

-continued
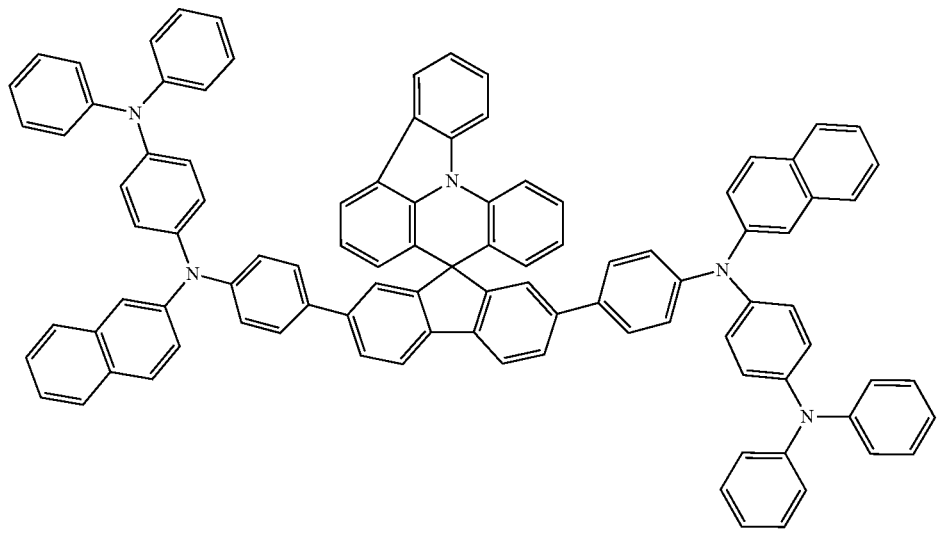
D65
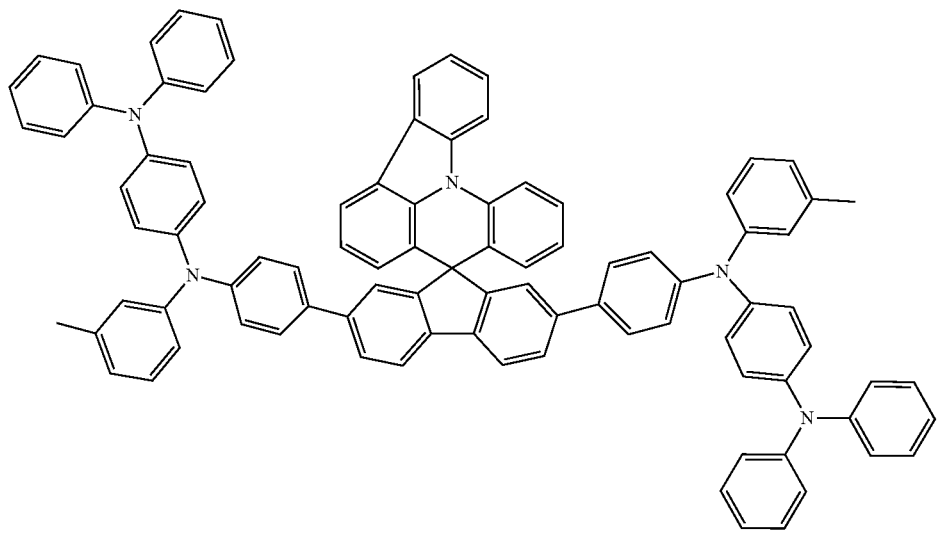
D66
When the first layer 326a includes the second compound represented by one or more of the above chemical compound, the organic electric element 320 may have high efficiency or long life.
The third chemical compound is one or more of the following chemical compounds.
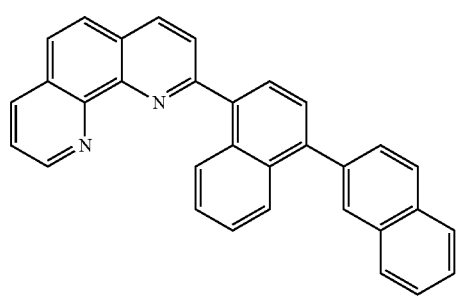
E01
-continued
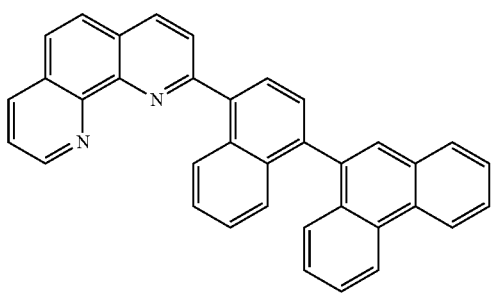
E02

E03
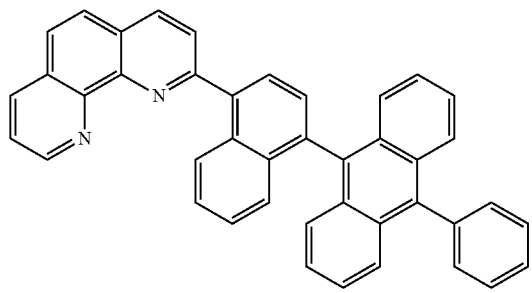
E04
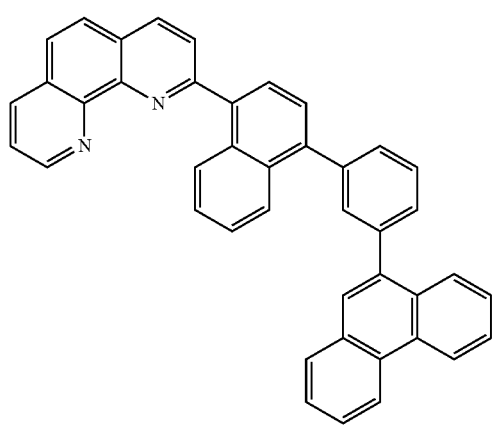
E05
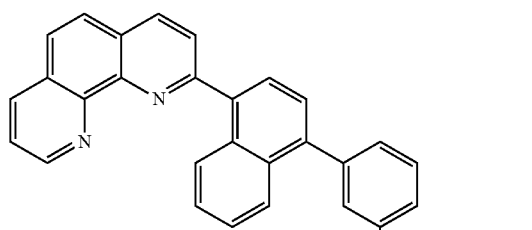
E06
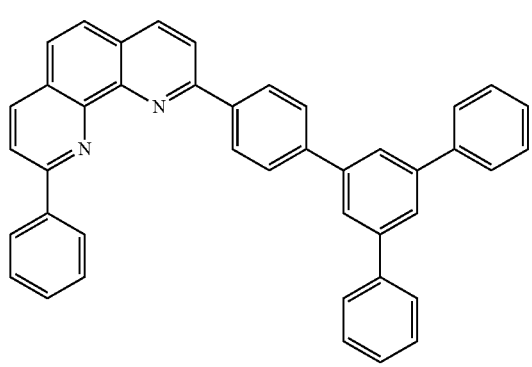
E07
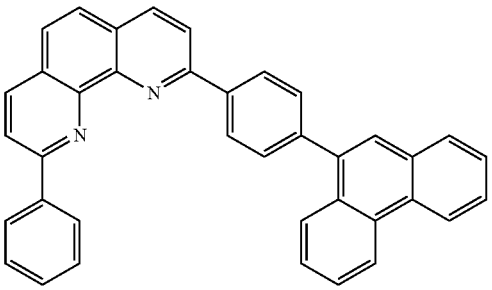
E08
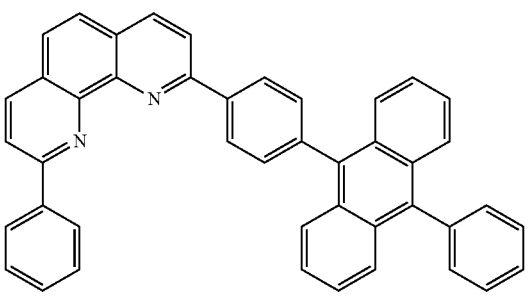
E09
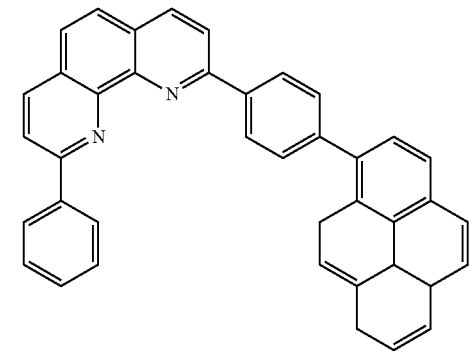
E10
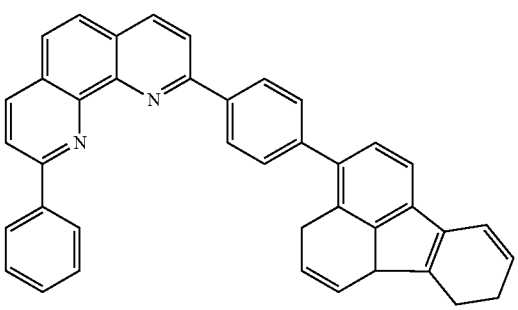
E11
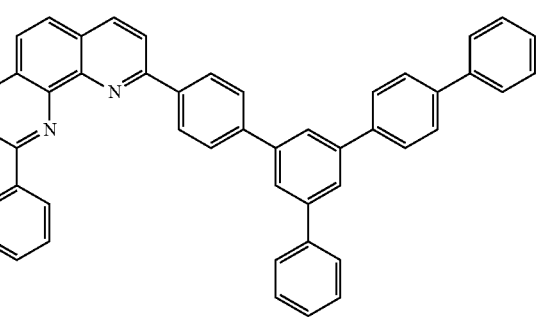

E12
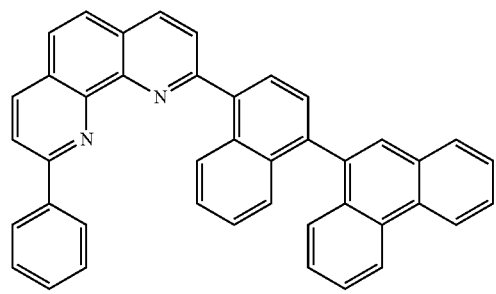
E13
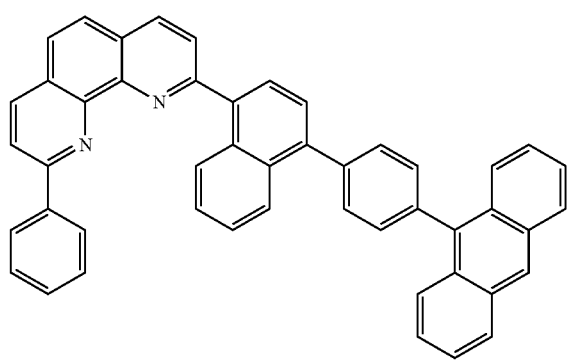
E14
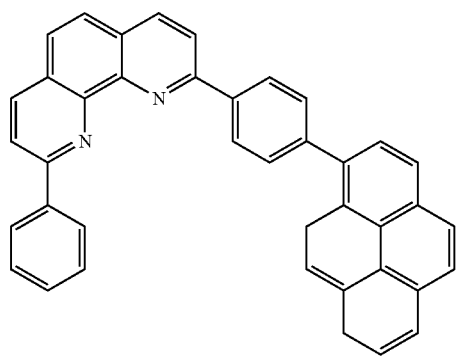
E15
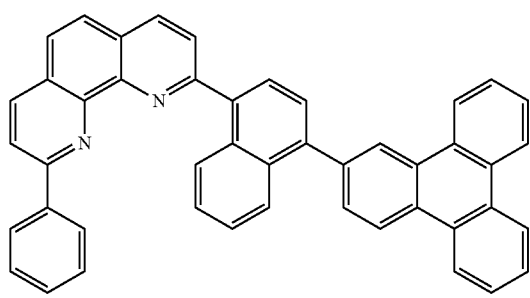
E16
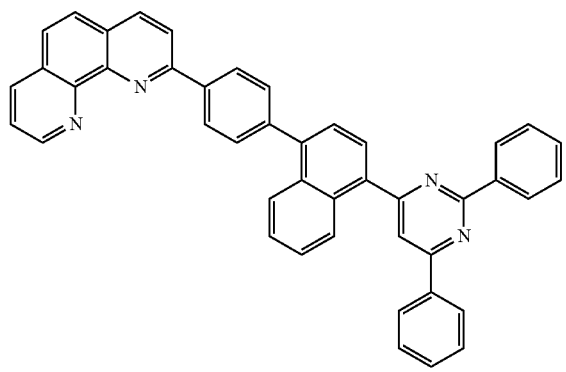
E17
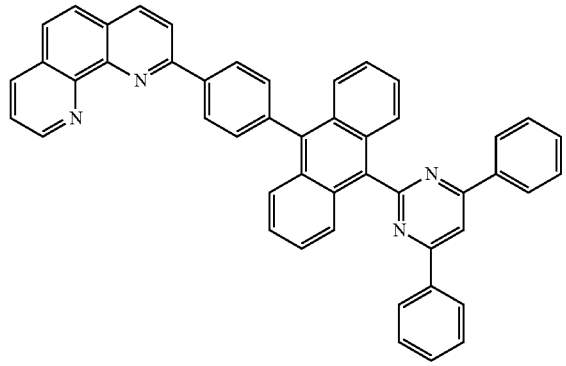
E18
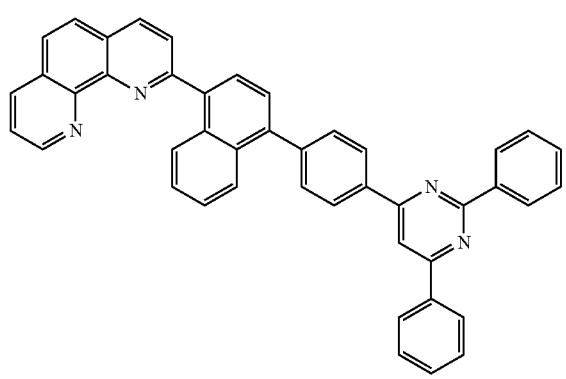
E19
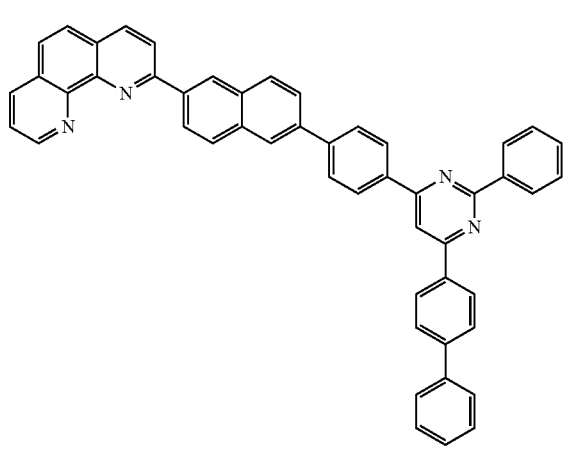

E20
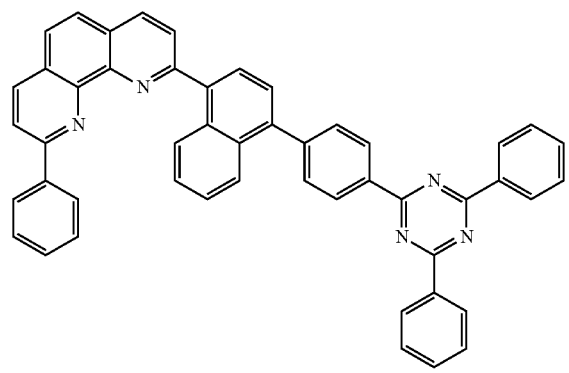
E21
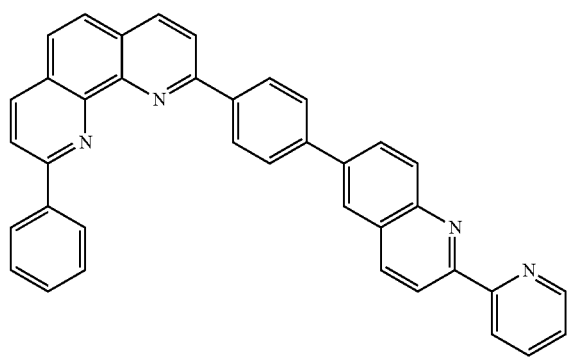
E22
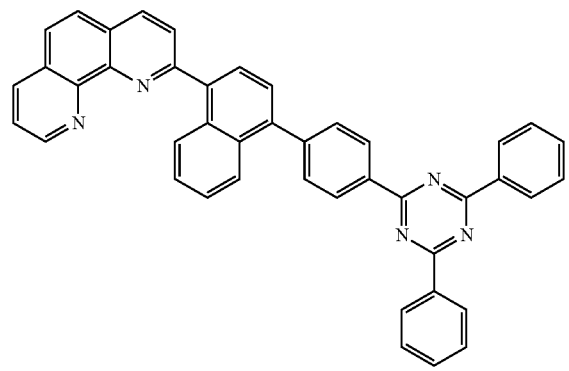
E23
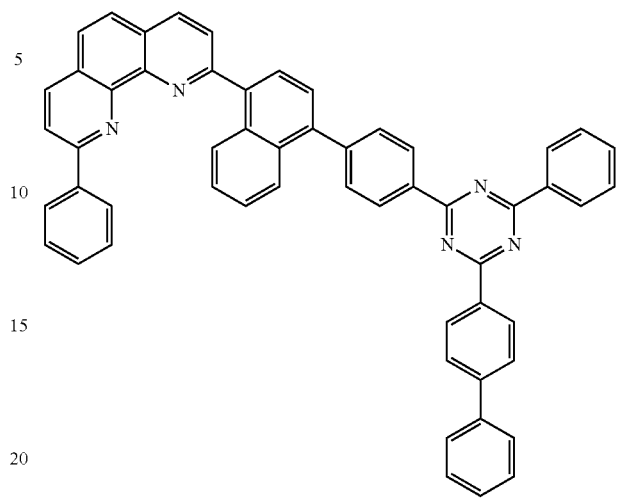
E24
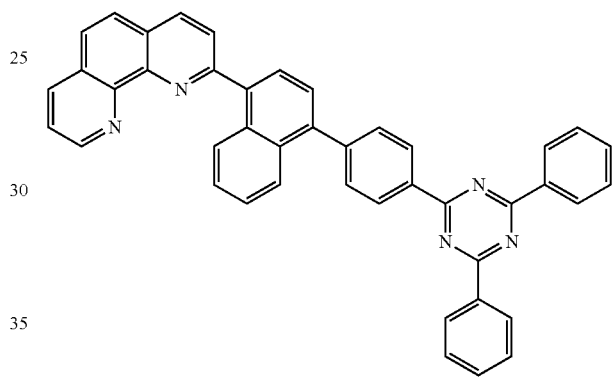
E25
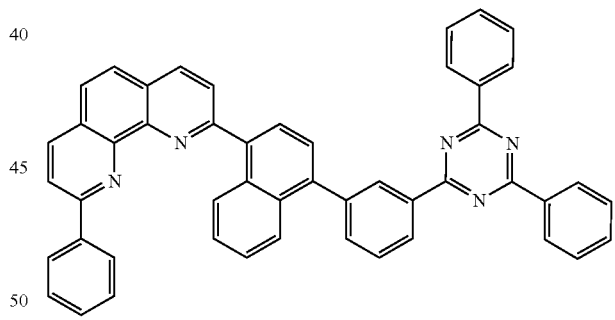
E26
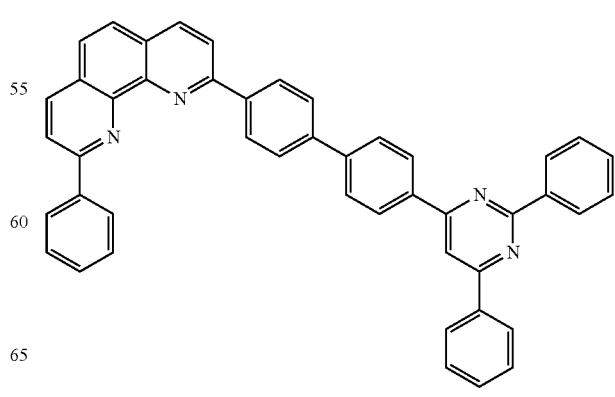

E27
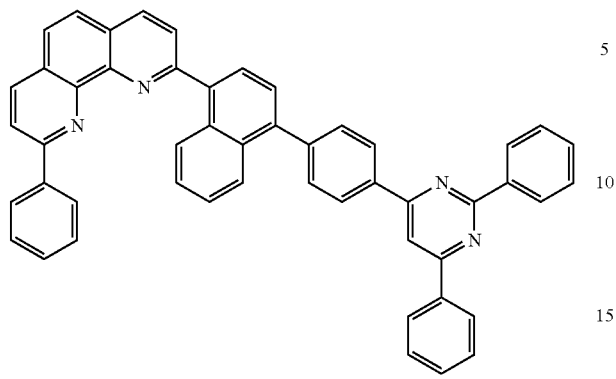
E28
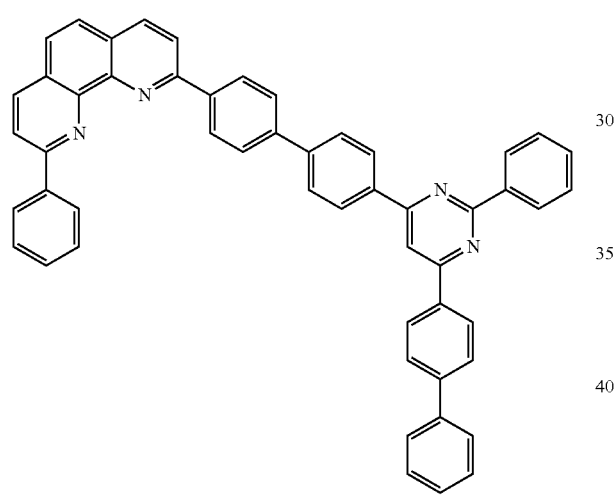
E29
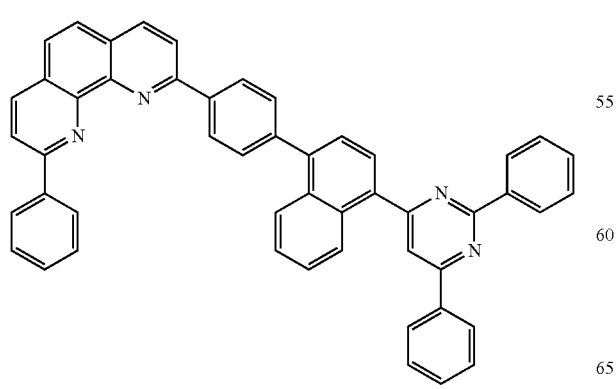
E30
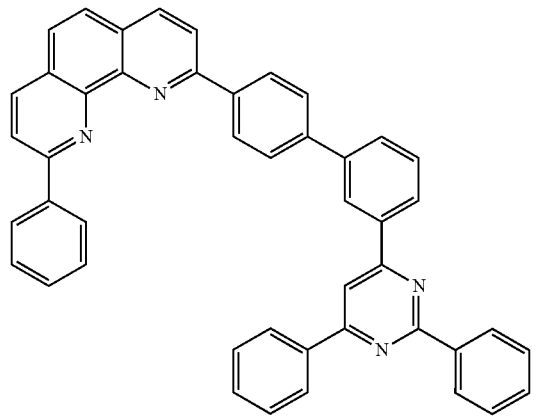
E31
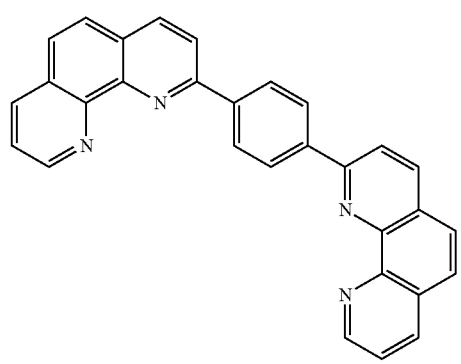
E32
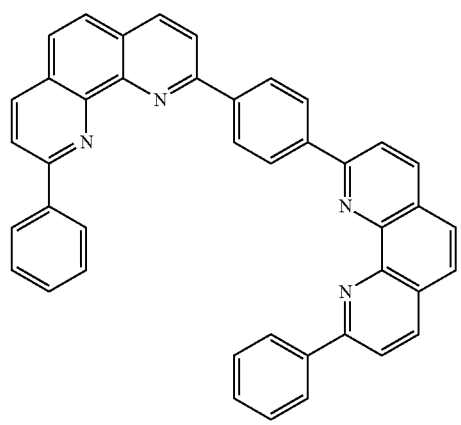
E33
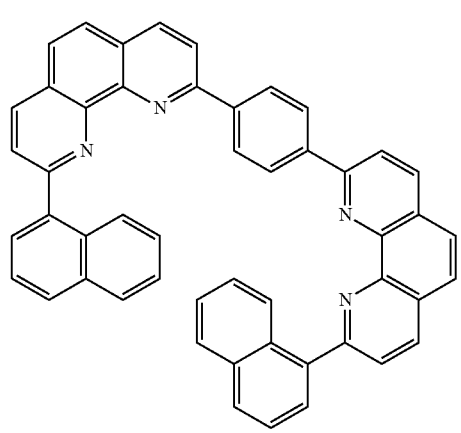

E34

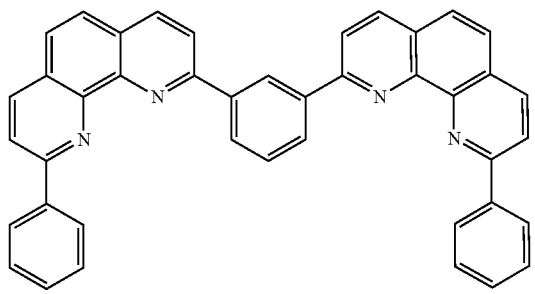

E35

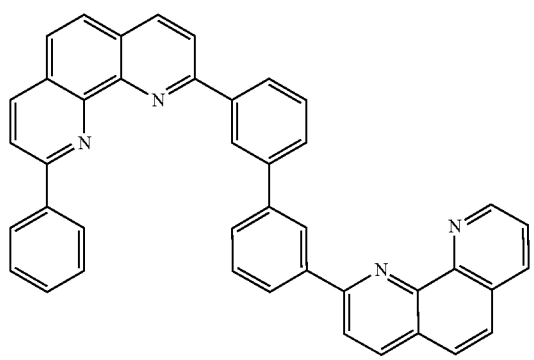

E36

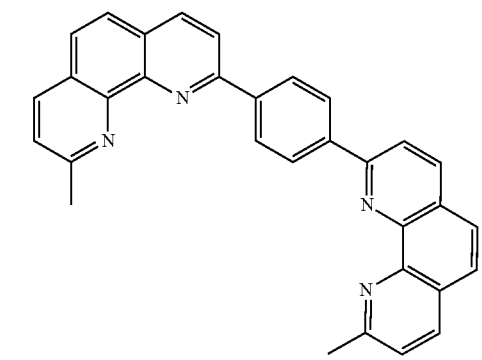

E37

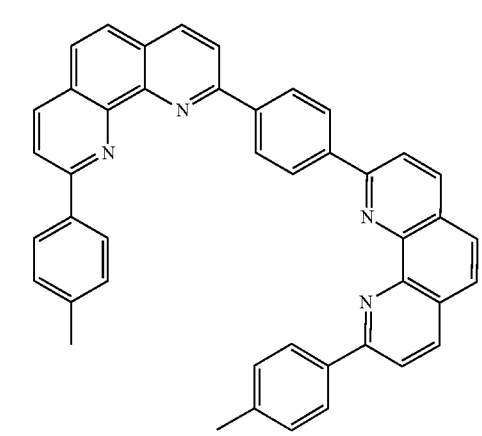

E38

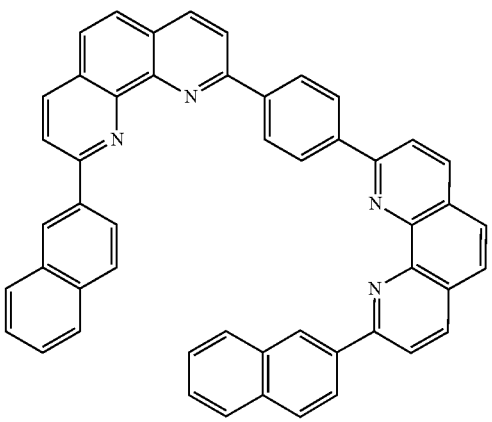

E39

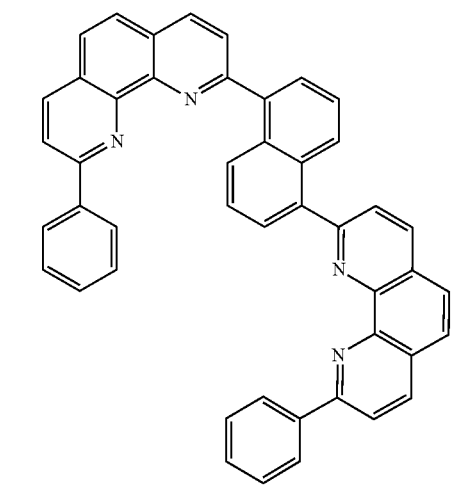

E40

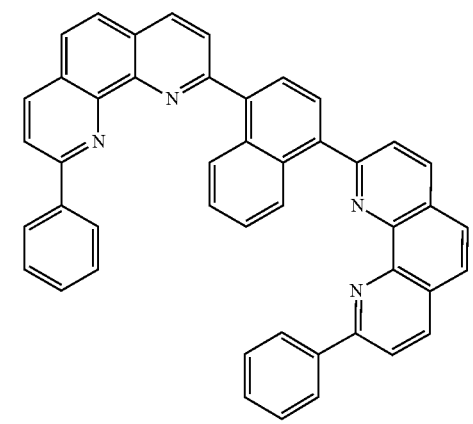

When the first layer 326a includes the third compound represented by one or more of the above chemical compound, the organic electric element 320 may have high efficiency or long life.

The organic electric element 320 satisfies the following general formula 1.

$$L_3 - L_1 \leq 2.1 \text{ eV}$$ [general formula 1]

In the general formula 1, $L_3$ is the LUMO (Lowest Unoccupied Molecular Orbital) energy level of the third compound.

$L_1$ is the LUMO energy level of the first compound.

The upper limit of $L_3-L_1$ defined in the general formula 1 may be 2.0 eV or less, or 1.8 eV or less.

The organic electric device 320 includes a first layer and a second layer including a first compound and a second compound satisfying the general formula 1 so that it may have a high efficiency or long life.

The organic electric element 320 satisfies the following general formula 2.

$$L_3-H_2 \leq 2.8 \text{ eV} \qquad \text{[general formula 2]}$$

In the general formula 2, $L_3$ is the LUMO (Lowest Unoccupied Molecular Orbital) energy level of the third compound.

$H_2$ is the HOMO (Highest Occupied Molecular Orbital) energy level of the second compound.

The upper limit of $L_3-H_2$ defined in the general formula 2 may be 2.6 eV or less, or 2.4 eV or less.

The organic electric device 320 includes the first and the second layers including the second and the third compounds satisfying the general formula 2 so that it may have a high efficiency or long life.

The organic electric element 320 satisfies the following general formula 3.

$$0.32 \text{ eV} \leq L_1-H_2 \leq 0.8 \text{ eV} \qquad \text{[general formula 3]}$$

In the general formula 3, $L_1$ is the LUMO (Lowest Unoccupied Molecular Orbital) energy level of the first compound.

$H_2$ is the HOMO (Highest Occupied Molecular Orbital) energy level of the second compound.

The lower limit of $L_1-H_2$ defined in the general formula 3 may be o.34 eV or more, or 0.38 eV or more.

The upper limit of $L_1-H_2$ defined in the general formula 3 may be o.65 eV or less, or 0.50 eV or less.

The organic electric device 320 includes a first layer including the first and the second compounds satisfying the general formula 3 so that it may have a high efficiency or long life.

The first compound included in the first layer 326a may be a dopant, and the second compound may be a host compound. Since the first layer 326a includes the above-described first compound as the dopant and the above-described second compound as the host, the first layer 326a has excellent hole transport properties so that the organic electric element may have excellent efficiency and lifespan.

The first compound may be doped at the ratio of 10% to 50% by weight into the first layer 326a. When the first compound satisfies the above ratio, the first layer has excellent hole transport properties so that the organic electric element may have excellent efficiency and lifespan.

The thickness of the first layer 326a is not particularly limited, but may be, for example, 50 Å to 500 Å.

The thickness of the second layer 326b is not particularly limited, but may be, for example, 50 Å to 500 Å.

The hole injection layer 327 may include a fourth compound and a fifth compound.

Details of the fourth compound are the same as those described for the first compound described above, unless otherwise specified. Accordingly, the fourth compound may be represented by one or more of the chemical formulas 1 and 2. In addition, the fourth compound may be represented by one or more of the chemical 5 and the chemical 6, or may be represented by one or more of the chemical formula 7 and the chemical 8. That is, what has been described for the first compound can be applied to the fourth compound as it is.

However, the specific fourth compound included in the organic electric element 320 according to the embodiments may be different from the first compound, or may be the same as each other.

Details of the fifth compound are the same as those described for the second compound described above, unless otherwise specified. Therefore, the fifth compound may be represented by the chemical formula 3 described above. That is, what has been described for the second compound may be applied to the fifth compound as it is.

However, the specific fifth compound included in the organic electric element 320 according to embodiments of the present invention may be different from the second compound, or may be the same as each other.

Since the organic electric element 320 includes a hole injection layer 327 including the fourth compound and the fifth compound, it may have high efficiency or long life.

In addition, the fourth compound included in the hole injection layer 327 may be a dopant, and the fifth compound may be a host compound. The hole injection layer 327 includes the above-described fourth compound as the dopant, and the fifth compound as the host, so that the hole injection layer 327 has excellent hole injection characteristics so that the organic electric element may have excellent efficiency and lifespan.

The fourth compound may be doped at a ratio of 10% to 50% by weight into the hole injection layer 327. When the fourth compound is doped to satisfy the above ratio, the hole injection layer 327 has excellent hole injection characteristics, so that the organic electric element may have excellent efficiency and lifespan.

The thickness of the hole injection layer 327 is not particularly limited, but may be, for example, 50 Å to 500 Å.

Other embodiments of the present invention may provide a display panel 110.

The display panel 110 includes a sub-pixel 111 including the above-described organic electric element 220.

In the display panel 110 according to the present embodiment, since the organic electrical element 220 is the same as the organic electrical element 220 according to the above-described embodiments, a description thereof will be omitted.

In addition, since the display panel 110 and the sub-pixel 111 according to the embodiments have been described above, a description thereof will be omitted.

Other embodiments of the present invention may provide a display device 100.

The display device 100 includes the above-described display panel 110 and a driving circuit for driving the above-described display panel 110.

In the display device 100 according to the present embodiments, the display panel 110 is the same as the display panel 110 according to the above-described embodiments, so a description thereof will be omitted.

In addition, since the driving circuit for driving the display panel according to embodiments has been described above, a description thereof will be omitted.

Hereinafter, examples of manufacturing an organic electric element according to the embodiments will be specifically described with reference to the embodiment, but the embodiments are not limited to the following examples.

Manufacturing Evaluation of Organic Electric Element

Comparative Example 1

After washing a glass substrate coated with ITO (indium tin oxide) to a thickness of 1,000 Å, the substrate is washed with a solvent such as isopropyl alcohol, acetone or methanol and dried. On this prepared ITO transparent electrode, NPD (N, N'-Di(1-naphthyl)-N,N'-diphenyl-(1,1'-biphenyl)-4,4'-diamine) is used as the fifth compound, F4-TCNQ (2,3,5,6-tetrafluoro-tetracyanoquinodimethane) was doped with 10% as the fourth compound and thermally vacuum-deposited to form a hole injection layer of 10 nm. A first hole transport layer (HTL1) was formed by thermal vacuum deposition of a hole transport material (NPD) of 100 nm.

After that, ADN (9,10-di(naphtha-2-yl)anthracene) and 1,6-Bis (diphenylamine)pyrene were used as host and dopant materials, respectively, doped with 3%, and thermally vacuum-deposited to a thickness of 20 nm to form a first light emitting layer.

Subsequently, a first electron transport layer was formed by thermal vacuum deposition of an electron transport material (TmPyPB, 1,3,5-Tri (m-pyridin-3-ylphenyl) benzene) to a thickness of 10 nm, and Bphen (Bathophenanthroline) as the third compound was used, and Li was doped with 2% to form a second layer (n-type charge generation layer) by thermal vacuum deposition to a thickness of 20 nm.

Subsequently, NPD (N,N'-Di(1-naphthyl)-N,N'-diphenyl-(1,1'-biphenyl)-4,4'-diamine) is used as the second compound and F4-TCNQ (2,3,5,6-tetrafluoro-tetracyanoquinodimethane) was doped with 10% as the first compound and thermally vacuum-deposited to form a first layer (p-type charge generation layer) of 10 nm.

Subsequently, NPD (N,N'-Di(1-naphthyl)-N,N'-diphenyl-(1,1'-biphenyl)-4,4'-diamine) as a hole transport material was vacuum-deposited to a thickness of 20 nm and then CBP (4,4'-Bis (N-carbazolyl)-1,1'-biphenyl) is used as a host and Ir(ppy)3 (tris(2-phenylpyridine) Iridium (III) was doped with 10% as a dopant. Thermal vacuum deposition was performed to form a second light emitting layer of 20 nm.

Subsequently, a second electron transport layer was formed by thermal vacuum deposition using Alq3 as an electron transport material, and then thermal vacuum deposition was performed using LiF as an electron injection material to form an electron injection layer. Subsequently, a cathode was formed by depositing Al to a thickness of 200 nm, thereby fabricating an organic electric element.

Embodiments 1 to 39 and Comparative Examples 1 to 9

The organic electric element was manufactured in the same manner as in the Comparative Example 1, except that the first compound, the second compound, the fourth compound, and the fifth compound were used in the types and ratios shown in Tables 1 and 2 below. Tables 3 and 4 show the performances of the manufactured organic electric elements.

TABLE 1

| | first chemical compound | second chemical compound | third chemical compound | fourth chemical compound | fifth chemical compound | $L_3$-$L_1$ (eV) | $L_3$-$H_2$ (eV) | $L_1$-$H_2$ (eV) |
|---|---|---|---|---|---|---|---|---|
| Comparative Example 1 | F4-TCNQ (10%) | NPD | Bphen | F4-TCNQ (10%) | NPD | 2.20 | 2.50 | 0.30 |
| Comparative Example 2 | F4-TCNQ (10%) | D01 | Bphen | F4-TCNQ (10%) | D01 | 2.20 | 2.16 | 0.04 |
| Comparative Example 3 | F4-TCNQ (10%) | D16 | Bphen | F4-TCNQ (10%) | D16 | 2.20 | 2.14 | −0.06 |
| Comparative Example 4 | F4-TCNQ (10%) | D19 | Bphen | F4-TCNQ (10%) | D19 | 2.20 | 2.10 | −0.10 |
| Comparative Example 5 | F4-TCNQ (10%) | D22 | Bphen | F4-TCNQ (10%) | D22 | 2.20 | 2.18 | −0.02 |
| Comparative Example 6 | F4-TCNQ (10%) | D28 | Bphen | F4-TCNQ (10%) | D28 | 2.20 | 2.17 | −0.03 |
| Comparative Example 7 | F4-TCNQ (10%) | D52 | Bphen | F4-TCNQ (10%) | D52 | 2.20 | 2.25 | 0.05 |
| Embodiment1 | A04 (10%) | NPD | Bphen | A04 (10%) | NPD | 1.75 | 2.50 | 0.75 |
| Embodiment2 | A04 (10%) | D01 | Bphen | A04 (10%) | D01 | 1.75 | 2.16 | 0.41 |
| Embodiment3 | A04 (10%) | D16 | Bphen | A04 (10%) | D16 | 1.75 | 2.14 | 0.39 |
| Embodiment4 | A04 (10%) | D19 | Bphen | A04 (10%) | D19 | 1.75 | 2.10 | 0.35 |
| Embodiment5 | A04 (10%) | D22 | Bphen | A04 (10%) | D22 | 1.75 | 2.18 | 0.43 |
| Embodiment6 | A04 (10%) | D28 | Bphen | A04 (10%) | D28 | 1.75 | 2.17 | 0.44 |
| Embodiment7 | A04 (10%) | D52 | Bphen | A04 (10%) | D52 | 1.75 | 2.25 | 0.50 |
| Embodiment8 | A15 (10%) | NPD | Bphen | A15 (10%) | NPD | 1.74 | 2.50 | 0.76 |
| Embodiment9 | A15 (10%) | D01 | Bphen | A15 (10%) | D01 | 1.74 | 2.16 | 0.42 |
| Embodiment10 | A15 (10%) | D16 | Bphen | A15 (10%) | D16 | 1.74 | 2.14 | 0.40 |
| Embodiment11 | A15 (10%) | D19 | Bphen | A15 (10%) | D19 | 1.74 | 2.10 | 0.36 |
| Embodiment12 | A15 (10%) | D22 | Bphen | A15 (10%) | D22 | 1.74 | 2.18 | 0.44 |
| Embodiment13 | A15 (10%) | D28 | Bphen | A15 (10%) | D28 | 1.74 | 2.17 | 0.45 |
| Embodiment14 | A15 (10%) | D52 | Bphen | A15 (10%) | D52 | 1.74 | 2.25 | 0.51 |
| Embodiment15 | A38 (10%) | NPD | Bphen | A38 (10%) | NPD | 1.80 | 2.50 | 0.70 |
| Embodiment16 | A38 (10%) | D01 | Bphen | A38 (10%) | D01 | 1.80 | 2.16 | 0.36 |
| Embodiment17 | A38 (10%) | D16 | Bphen | A38 (10%) | D16 | 1.80 | 2.14 | 0.34 |
| Embodiment18 | A38 (10%) | D19 | Bphen | A38 (10%) | D19 | 1.80 | 2.10 | 0.30 |
| Embodiment19 | A38 (10%) | D22 | Bphen | A38 (10%) | D22 | 1.80 | 2.18 | 0.38 |
| Embodiment20 | A38 (10%) | D28 | Bphen | A38 (10%) | D28 | 1.80 | 2.17 | 0.39 |
| Embodiment21 | A38 (10%) | D52 | Bphen | A38 (10%) | D52 | 1.80 | 2.25 | 0.45 |

TABLE 2

| | first chemical compound | second chemical compound | third chemical compound | fourth chemical compound | fifth chemical compound | $L_3$-$L_1$ (eV) | $L_3$-$H_2$ (eV) | $L_1$-$H_2$ (eV) |
|---|---|---|---|---|---|---|---|---|
| Comparative Example 1 | F4-TCNQ (10%) | NPD | Bphen | F4-TCNQ (10%) | NPD | 2.20 | 2.50 | 0.30 |
| Comparative Example 8 | F4-TCNQ (20%) | NPD | Bphen | F4-TCNQ (20%) | NPD | 2.20 | 2.50 | 0.30 |
| Comparative Example 9 | F4-TCNQ (30%) | NPD | Bphen | F4-TCNQ (30%) | NPD | 2.20 | 2.50 | 0.30 |
| Embodiment 1 | A04 (10%) | NPD | Bphen | A04 (10%) | NPD | 1.75 | 2.50 | 0.75 |
| Embodiment 22 | A04 (20%) | NPD | Bphen | A04 (20%) | NPD | 1.75 | 2.50 | 0.75 |
| Embodiment 23 | A04 (30%) | NPD | Bphen | A04 (30%) | NPD | 1.75 | 2.50 | 0.75 |
| Embodiment 24 | A04 (10%) | NPD | E05 | A04 (10%) | NPD | 1.69 | 2.44 | 0.75 |
| Embodiment 3 | A04 (10%) | D16 | Bphen | A04 (10%) | D16 | 1.75 | 2.14 | 0.39 |
| Embodiment 25 | A04 (10%) | D16 | E05 | A04 (10%) | D16 | 1.69 | 2.08 | 0.39 |
| Embodiment 26 | A04 (20%) | D16 | E05 | A04 (20%) | D16 | 1.69 | 2.08 | 0.39 |
| Embodiment 26 | A04 (30%) | D16 | E05 | A04 (30%) | D16 | 1.69 | 2.08 | 0.39 |
| Embodiment 28 | A04 (10%) | D22 | E27 | A04 (10%) | D22 | 1.63 | 2.06 | 0.43 |
| Embodiment 29 | A04 (20%) | D22 | E27 | A04 (20%) | D22 | 1.63 | 2.06 | 0.43 |
| Embodiment 30 | A04 (30%) | D22 | E27 | A04 (30%) | D22 | 1.63 | 2.06 | 0.43 |
| Embodiment 8 | A15 (10%) | NPD | Bphen | A15 (10%) | NPD | 1.74 | 2.50 | 0.76 |
| Embodiment 31 | A15 (20%) | NPD | Bphen | A15 (20%) | NPD | 1.74 | 2.50 | 0.76 |
| Embodiment 32 | A15 (30%) | NPD | Bphen | A15 (30%) | NPD | 1.74 | 2.50 | 0.76 |
| Embodiment 33 | A15 (10%) | NPD | E05 | A15 (10%) | NPD | 1.68 | 2.44 | 0.76 |
| Embodiment 10 | A15 (10%) | D16 | Bphen | A15 (10%) | D16 | 1.74 | 2.14 | 0.40 |
| Embodiment 34 | A15 (10%) | D16 | E05 | A15 (10%) | D16 | 1.68 | 2.08 | 0.40 |
| Embodiment 35 | A15 (20%) | D16 | E05 | A15 (20%) | D16 | 1.68 | 2.08 | 0.40 |
| Embodiment 36 | A15 (30%) | D16 | E05 | A15 (30%) | D16 | 1.68 | 2.08 | 0.40 |
| Embodiment 37 | A15 (10%) | D22 | E27 | A15 (10%) | D22 | 1.62 | 2.06 | 0.44 |
| Embodiment 38 | A15 (20%) | D22 | E27 | A15 (20%) | D22 | 1.62 | 2.06 | 0.44 |
| Embodiment 39 | A15 (30%) | D22 | E27 | A15 (30%) | D22 | 1.62 | 2.06 | 0.44 |

In Tables 1 and 2, A04, A15 and A38 are A04, A15 and A38 chemical compounds described as being selectable as the first chemical compound, and D01, D16, D19, D22, D28 and D52 are the second D01, D16, D19, D22, D28 and D52 chemical compounds described as being selectable as chemical compounds, and E05 and E27 are E05 and E27 chemical compounds described as being selectable as the third chemical compounds. F4-TCNQ is as follows.

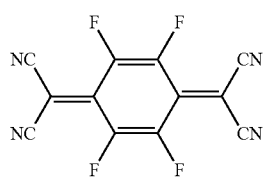

F4-TCNQ

TABLE 3

| | driving voltage (V) | efficiency (cd/A) | color coordinate (CIE x, y) | | lifespan (T95, hr) |
|---|---|---|---|---|---|
| Comparative Example 1 | 10.6 | 56.1 | 0.317 | 0.33 | 283 |
| Comparative Example 2 | 10.4 | 56.4 | 0.32 | 0.345 | 294 |
| Comparative Example 3 | 9.8 | 59.4 | 0.323 | 0.34 | 264 |
| Comparative Example 4 | 9.9 | 58.9 | 0.321 | 0.336 | 271 |
| Comparative Example 5 | 10.2 | 56.3 | 0.318 | 0.344 | 280 |
| Comparative Example 6 | 10.2 | 55.8 | 0.325 | 0.342 | 245 |
| Comparative Example 7 | 11.3 | 55.4 | 0.319 | 0.344 | 249 |
| Embodiment1 | 9.5 | 60.3 | 0.322 | 0.339 | 305 |
| Embodiment2 | 9.2 | 61.4 | 0.32 | 0.34 | 313 |
| Embodiment3 | 8.7 | 63.4 | 0.325 | 0.338 | 335 |
| Embodiment4 | 9 | 62.2 | 0.323 | 0.335 | 319 |
| Embodiment5 | 8.4 | 64 | 0.327 | 0.341 | 350 |
| Embodiment6 | 8.8 | 62.5 | 0.319 | 0.34 | 322 |
| Embodiment7 | 9.4 | 61.9 | 0.32 | 0.343 | 330 |
| Embodiment8 | 9.3 | 61.8 | 0.326 | 0.339 | 314 |
| Embodiment9 | 9.2 | 62.6 | 0.325 | 0.341 | 325 |
| Embodiment10 | 8.5 | 63.4 | 0.324 | 0.34 | 364 |
| Embodiment11 | 8.9 | 62.9 | 0.322 | 0.337 | 342 |
| Embodiment12 | 8.2 | 64.2 | 0.319 | 0.341 | 369 |
| Embodiment13 | 8.7 | 64 | 0.321 | 0.34 | 303 |
| Embodiment14 | 9.1 | 62.8 | 0.323 | 0.342 | 347 |
| Embodiment15 | 9.1 | 62.4 | 0.32 | 0.338 | 305 |
| Embodiment16 | 9.2 | 62 | 0.319 | 0.335 | 321 |
| Embodiment17 | 8 | 64.2 | 0.322 | 0.339 | 361 |
| Embodiment18 | 8.7 | 62.7 | 0.323 | 0.337 | 333 |
| Embodiment19 | 8.1 | 63.5 | 0.32 | 0.341 | 382 |
| Embodiment20 | 8.6 | 63.8 | 0.324 | 0.344 | 326 |
| Embodiment21 | 9 | 63 | 0.323 | 0.343 | 340 |

TABLE 4

| | driving voltage (V) | efficiency (cd/A) | color coordinate (CIE x, y) | | lifespan (T95, hr) |
|---|---|---|---|---|---|
| Comparative Example 1 | 10.6 | 56.1 | 0.317 | 0.33 | 283 |
| Comparative Example 8 | 10.2 | 57.6 | 0.321 | 0.332 | 296 |
| Comparative Example 9 | 9.9 | 58 | 0.32 | 0.331 | 271 |
| Embodiment 1 | 9.5 | 60.3 | 0.322 | 0.339 | 305 |
| Embodiment 22 | 9.5 | 59.8 | 0.324 | 0.334 | 297 |
| Embodiment 23 | 9.6 | 60.6 | 0.321 | 0.329 | 284 |
| Embodiment 24 | 9.1 | 62.7 | 0.326 | 0.331 | 310 |
| Embodiment 3 | 8.7 | 63.4 | 0.319 | 0.338 | 335 |
| Embodiment 25 | 8.7 | 63.4 | 0.319 | 0.338 | 335 |
| Embodiment 26 | 8.5 | 63.9 | 0.324 | 0.329 | 366 |
| Embodiment 26 | 8.1 | 64.2 | 0.322 | 0.334 | 371 |
| Embodiment 28 | 8.4 | 64 | 0.327 | 0.341 | 350 |
| Embodiment 29 | 8.2 | 64.3 | 0.324 | 0.335 | 374 |
| Embodiment 30 | 7.9 | 64.7 | 0.321 | 0.336 | 397 |
| Embodiment 8 | 9.3 | 61.8 | 0.326 | 0.339 | 314 |
| Embodiment 31 | 9.1 | 62.3 | 0.325 | 0.336 | 327 |
| Embodiment 32 | 9 | 62.6 | 0.322 | 0.334 | 330 |
| Embodiment 33 | 8.9 | 63 | 0.321 | 0.331 | 34 |
| Embodiment 10 | 8.5 | 63.4 | 0.317 | 0.34 | 364 |
| Embodiment 34 | 8.5 | 63.4 | 0.317 | 0.34 | 364 |
| Embodiment 35 | 8.1 | 63.9 | 0.319 | 0.336 | 399 |
| Embodiment 36 | 7.8 | 64 | 0.323 | 0.338 | 423 |
| Embodiment 37 | 8.2 | 64.2 | 0.319 | 0.341 | 369 |
| Embodiment 38 | 7.9 | 64.3 | 0.32 | 0.341 | 402 |
| Embodiment 39 | 7.7 | 64.1 | 0.325 | 0.339 | 418 |

As can be seen from the results of Tables 3 and 4, the organic electric element according to the embodiments includes the charge generating layer including the first layer including the first compound and the second compound according to the embodiments and the second layer including the third compound so that it may have excellent efficiency or lifespan compared to the organic electric element of the Comparative Example.

In the case of Embodiments 1, 8 and 15 including the first layer including the first compound represented by at least one of the chemical formula 1 and the chemical formula 2, its efficiency of lifespan is improved compared to the organic electric element of the Comparative Embodiment.

In addition, compared to the Embodiments 1, 8 and 15, it can be seen that the organic electric element of the Embodiments including the first layer further comprising the second compound represented by the chemical formula 3 has better efficiency and longer life than the organic electric elements of Embodiments 1, 8 and 15. In addition, it can be seen that the organic electric element of the Embodiments comprising the second layer containing the third compound represented by the chemical formula 4 has better efficiency and longer life than the organic electric elements of Embodiments 1, 8 and 15. In addition, it can be seen that the organic electric element of the embodiments comprising the first layer further comprising a second compound represented by the chemical formula 3 and a second layer comprising a third compound represented by the chemical formula 4 has better efficiency and longer life than the organic electric elements of Embodiments 1, 8 and 15.

Accordingly, it can be seen that a feature comprising the first compound represented by one or more of the chemical formulas 1 and 2 and the second compound represented by the chemical formula 3, and a feature comprising a third compound represented by the chemical formula 4 provide synergistic effects with each other to provide a more excellent organic electric element.

Further, in the Comparative Examples 1, 8, and 9, the driving voltage, efficiency, and lifespan did not increase even when the doping ratio of the p-type doping material was increased, but in the case of the Embodiment, when the doping ratio of the first chemical compound that is the p-type doping material was increased, it can be seen that the organic electric element is improved in terms of the driving voltage, efficiency, or lifespan.

It will be apparent to those skilled in the art that various modifications and variations can be made in the display device of the present disclosure without departing from the technical idea or scope of the disclosure. Thus, it is intended that the present disclosure cover the modifications and variations of this disclosure provided they come within the scope of the appended claims and their equivalents.

What is claimed is:

1. An organic electric element comprising:
a first electrode;
a second electrode; and
an organic layer positioned between the first electrode and the second electrode, the organic layer comprising:
a first stack comprising a first emitting layer,
a second stack comprising a second emitting layer, and
a charge generating layer positioned between the first stack and the second stack, the charge generating layer comprising:
a first layer comprising:
a first compound represented by one or more of chemical formula 1 and chemical formula 2, and
a second compound, and
a second layer comprising a third compound represented by chemical formula 4:

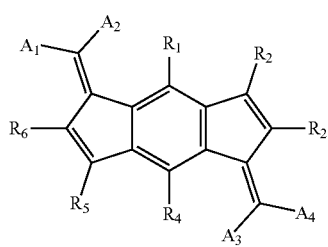

[chemical formula 1]

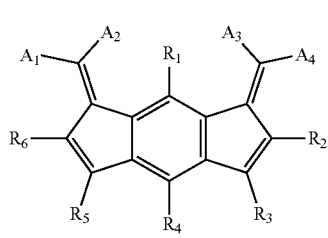

[chemical formula 2]

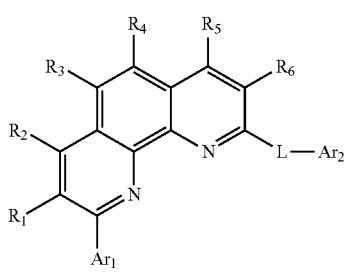

[chemical formula 4]

in chemical formula 1 and chemical formula 2, $R_1$ to $R_6$, which are same or different, are each independently one selected from the group consisting of a hydrogen; a deuterium; a tritium; a halogen; a cyano group; a nitro group; a $C_6$-$C_{60}$ aryl group; a fluorenyl group; a $C_2$-$C_{60}$ hetero ring group containing at least one hetero atom from O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; a $C_3$-$C_{60}$ alkylsilyl group; a $C_{18}$-$C_{60}$ arylsilyl group; and a $C_8$-$C_{60}$ alkylarylsilyl group, and one or more of $R_1$ to $R_6$ is the cyano group, $A_1$ to $A_4$, which are the same or different, are each independently one selected from the group consisting of a hydrogen; a deuterium; a tritium; a halogen; a cyano group; a nitro group; a $C_6$-$C_{60}$ aryl group; a fluorenyl group; a $C_2$-$C_{60}$ hetero ring group containing at least one hetero atom from O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; a $C_3$-$C_{60}$ alkylsilyl group; a $C_{18}$-$C_{60}$ arylsilyl group; and a $C_8$-$C_{60}$ alkylarylsilyl group, in $R_1$ to $R_6$ and $A_1$ to $A_4$ of chemical formula 1 and chemical formula 2, the aryl group, the fluorenyl group, the hetero ring group, the fused ring group, the alkyl group, the alkenyl group, the alkynyl group, the alkoxy group, the aryloxy group, the alkylsilyl group, the arylsilyl group and the alkylarylsilyl group are each optionally substituted with at least one substituent selected from the group consisting of a deuterium; a nitro group; a cyano group; a halogen; an amino group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with the deuterium; a fluorenyl group; a $C_2$-$C_{20}$ hetero ring group; a $C_3$-$C_{60}$ alkylsilyl group; a $C_{18}$-$C_{60}$ arylsilyl group; and a $C_8$-$C_{60}$ alkylarylsilyl group, in chemical formula 4, $R_1$ to $R_6$, which are same or different, are each independently one selected from the group consisting of a hydrogen; a deuterium; a tritium; a halogen; a cyano group; a nitro group; a $C_6$-$C_{60}$ aryl group; a fluorenyl group; a $C_2$-$C_{60}$ hetero ring group containing at least one hetero atom from O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; a $C_3$-$C_{60}$ alkylsilyl group; a $C_{18}$-$C_{60}$ arylsilyl group; and a $C_8$-$C_{60}$ alkylarylsilyl group, $Ar_1$ is one selected from the group consisting of a hydrogen; a deuterium; a tritium; a halogen; a cyano group; a nitro group; a $C_6$-$C_{60}$ aryl group; a fluorenyl group; a $C_2$-$C_{60}$ hetero ring group containing at least one hetero atom from O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; a $C_3$-$C_{60}$ alkylsilyl group; a $C_{18}$-$C_{60}$ arylsilyl group; and a $C_8$-$C_{60}$ alkylarylsilyl group, $Ar_2$ is one selected from the group consisting of a hydrogen deuterium; a tritium; a halogen; a cyano group; a nitro group; a $C_6$-$C_{60}$ aryl group; a fluorenyl group; a $C_2$-$C_{60}$ hetero ring group containing at least one hetero atom from O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; a $C_3$-$C_{60}$ alkylsilyl group; a $C_{18}$-$C_{60}$ arylsilyl group; and a $C_8$-$C_{60}$ alkylarylsilyl group, L is one selected from the group consisting of a $C_6$-$C_{60}$ arylene group; a fluorylene group; a $C_2$-$C_{60}$ divalent hetero ring group containing at least one heteroatom from O, N, S, Si and P; a divalent fused ring group of a $C_3$-$C_{60}$ aliphatic ring and a $C_6$-$C_{60}$ aromatic ring, and in $R_1$ to $R_6$, $Ar_1$, $Ar_2$ and L of chemical formula 4, the aryl group, the fluorenyl group, the hetero ring group, the fused ring group, the alkyl group, the alkenyl group, the alkynyl group, the alkoxy group, the aryloxy group, the alkylsilyl group, the arylsilyl group, the alkylarylsilyl group, the arylene group, the fluorylene group, the divalent hetero ring group, the divalent fused ring group are each optionally substituted with at least one substituent selected from the group consisting of a deuterium; a nitro group; a cyano group; a halogen; an amino group; a $C_1$-$C_{20}$ alkoxyl group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with the deuterium; a fluorenyl group; a $C_2$-$C_{20}$ hetero ring group; a $C_3$-$C_{60}$ alkylsilyl group; a $C_{18}$-$C_{60}$ arylsilyl group; and a $C_8$-$C_{60}$ alkylarylsilyl group, and the second compound is one or more of:

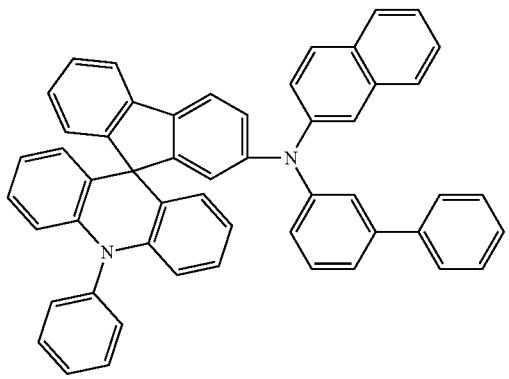

D53

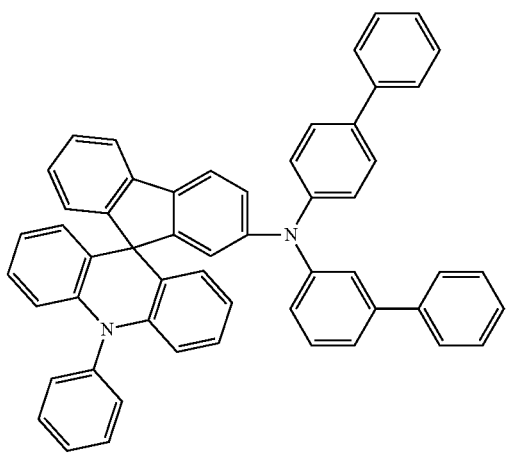

D54

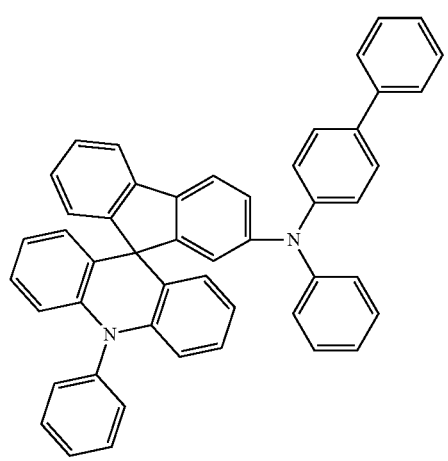

D51

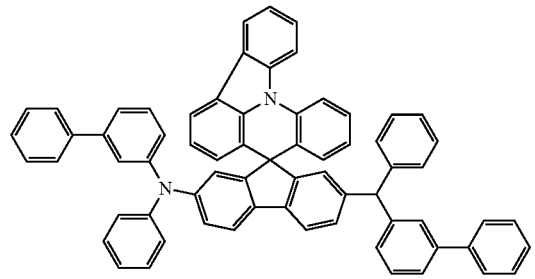

D55

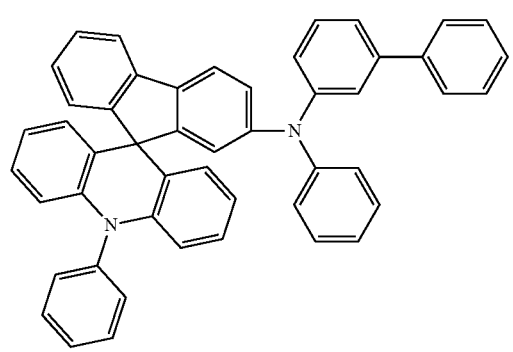

D52

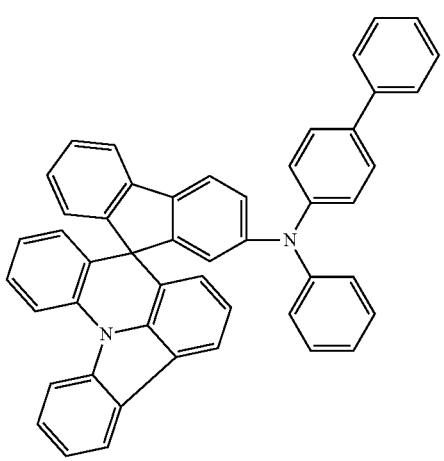

D56

-continued
D57
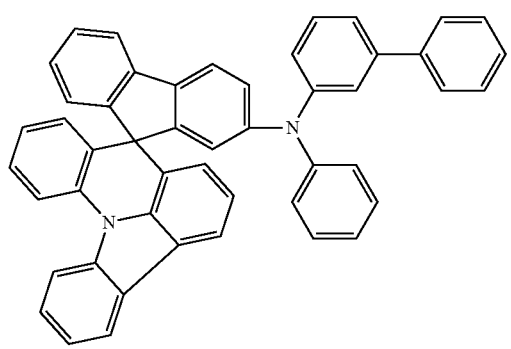
D58
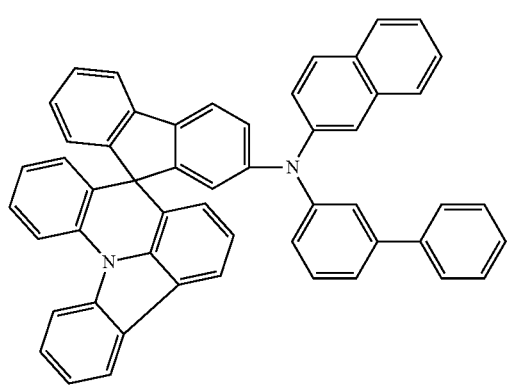
D59
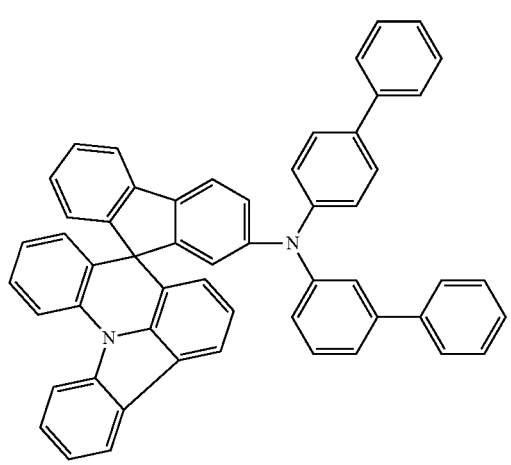
D60
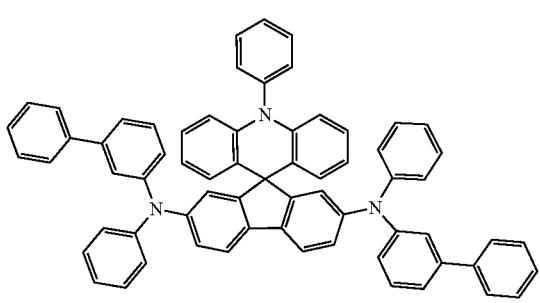
-continued
D61
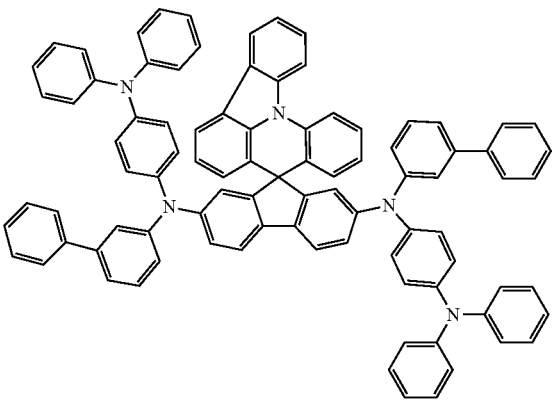
D62
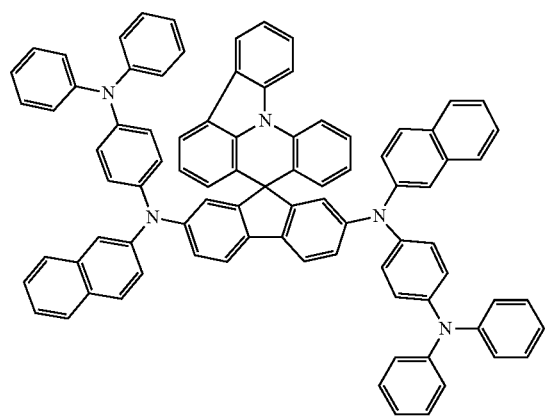
D63
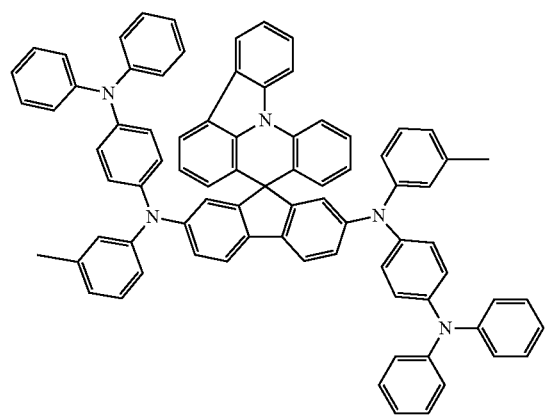
D64
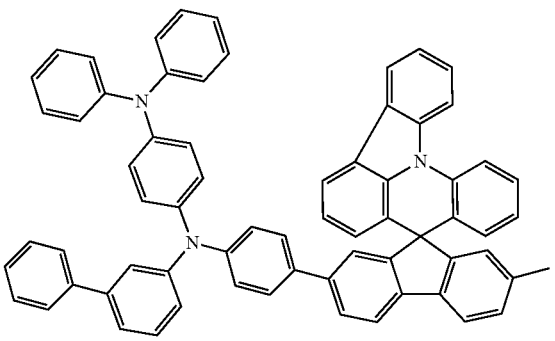

-continued

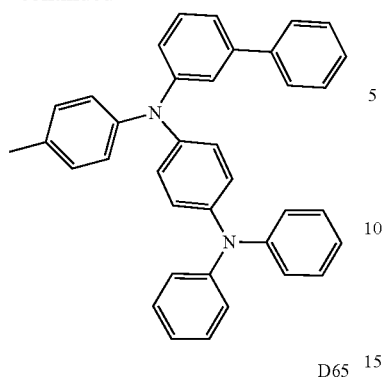

D65

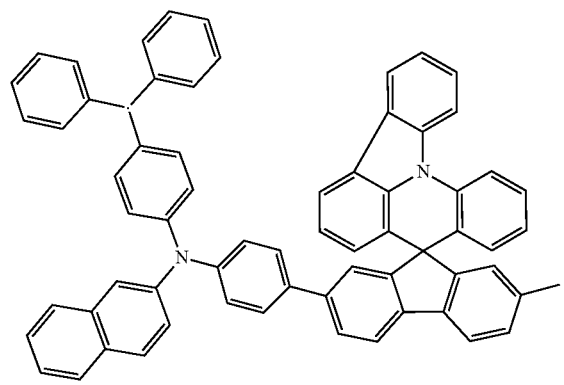

D66

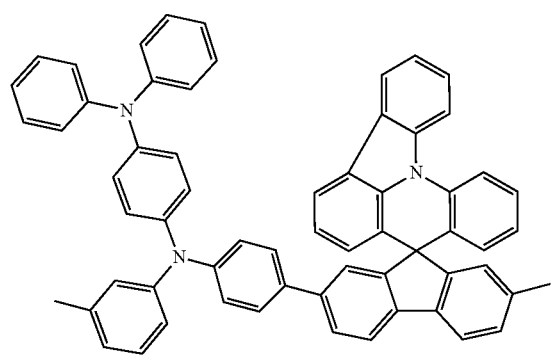

-continued

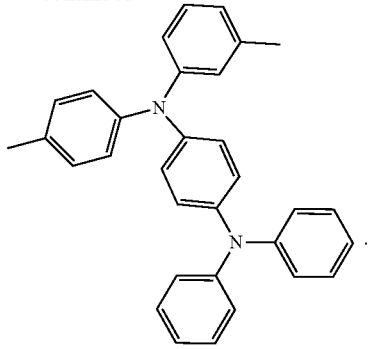

2. The organic electric element according to claim 1, wherein the first compound is represented by one or more of chemical formula 5 and chemical formula 6:

[chemical formula 5]

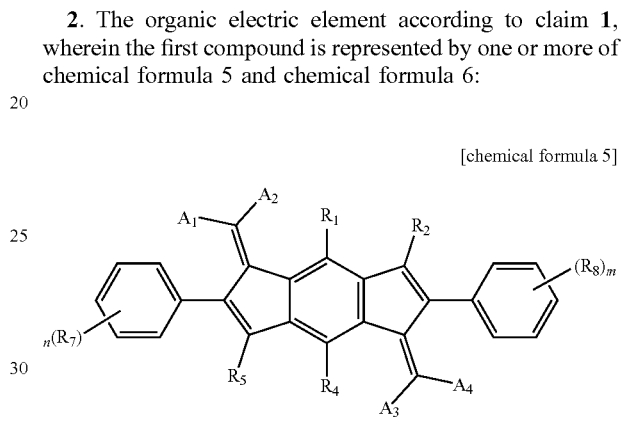

[chemical formula 6]

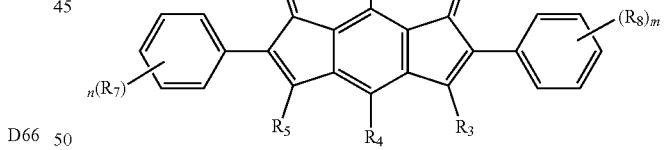

in chemical formula 5 and chemical formula 6, n and m are each independently an integer from 0 to 5, $R_7$ to $R_8$, which are the same or different, are each independently one selected from the group consisting of a deuterium; a tritium; a halogen; a cyano group; a $C_1$-$C_{50}$ alkyl group; and a $C_1$-$C_{30}$ alkoxy group, and in $R_7$ and $R_8$ of chemical formula 5 and chemical formula 6, the alkyl group and the alkoxy group are each optionally substituted with at least one substituent selected from the group consisting of a deuterium and a halogen.

3. The organic electric element according to claim 1, wherein the first compound is represented by one or more of chemical formula 7 and formula 8:

[chemical formula 7]
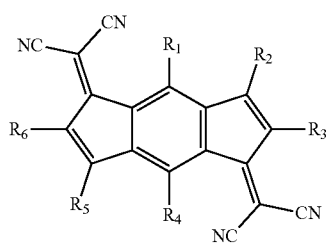
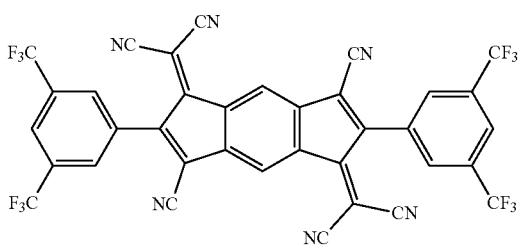
A04
[chemical formula 8]
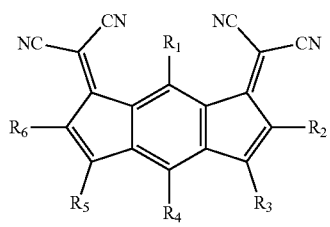
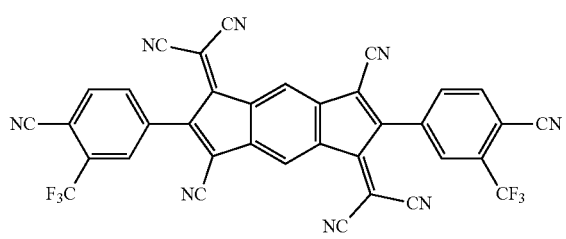
A05
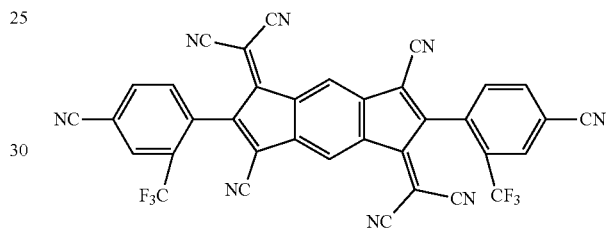
A06
in chemical formula 7 and chemical formula 8,
$R_1$ to $R_6$ are the same as $R_1$ to $R_6$ defined in chemical formulas 1 and 2.
4. The organic electric element according to claim 1, wherein the first compound is one or more of:
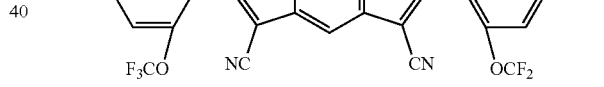
A07
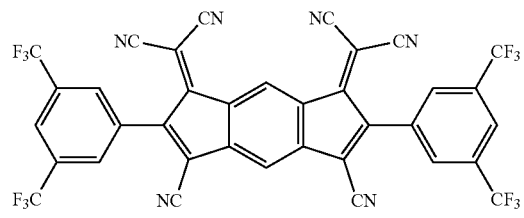
A01
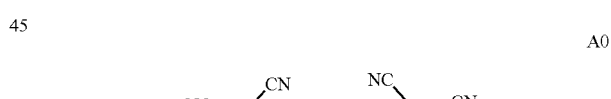
A08
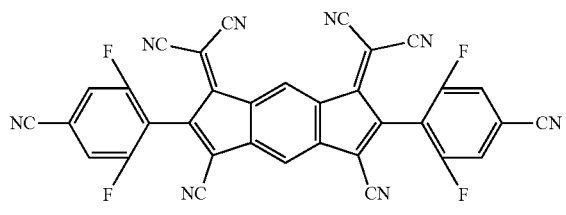
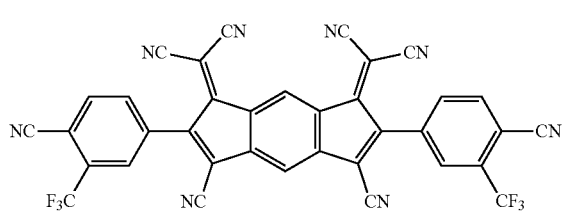
A02
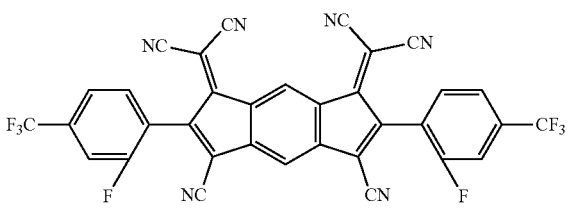
A09
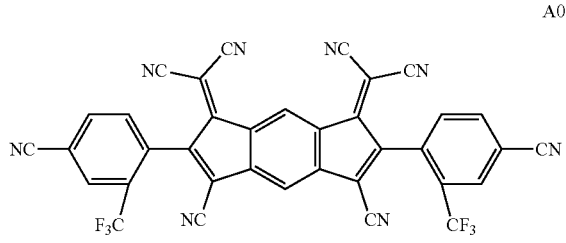
A03

-continued
A10
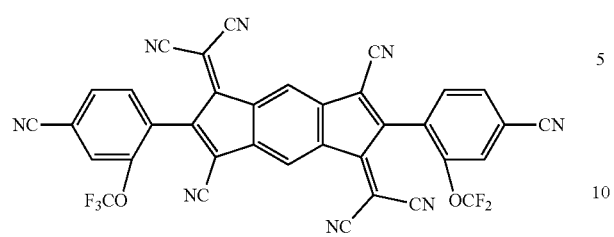
A11
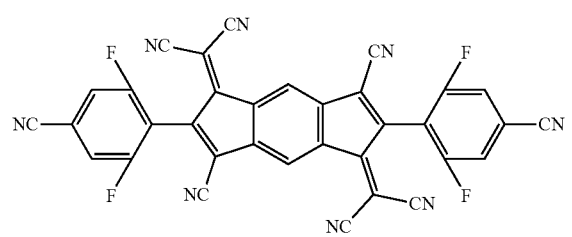
A12
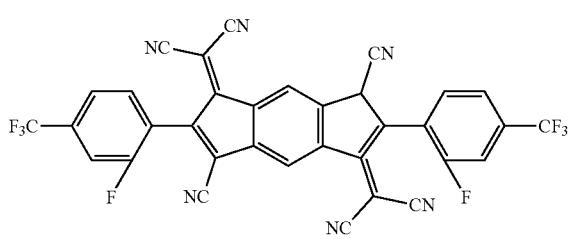
A13
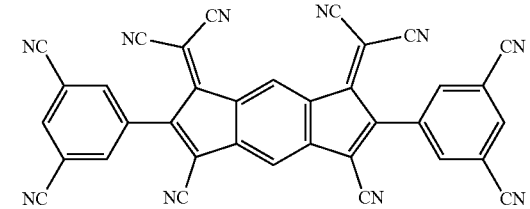
A14
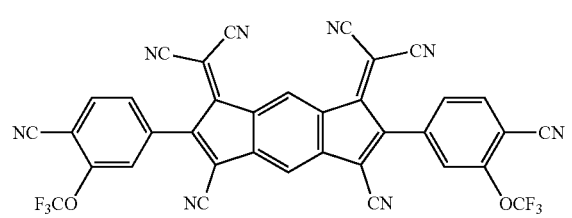
A15
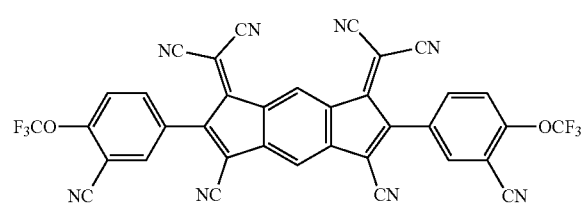
-continued
A16
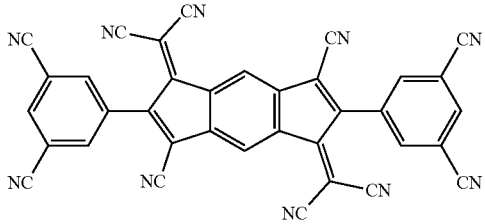
A17
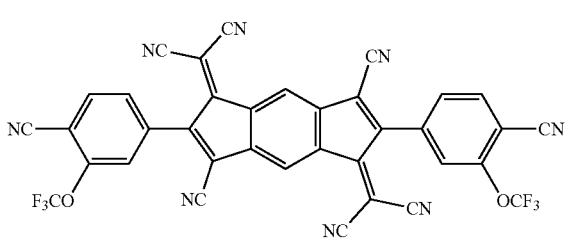
A18
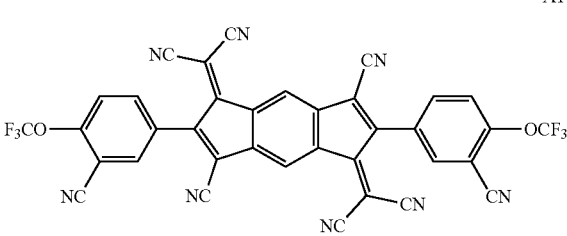
A19
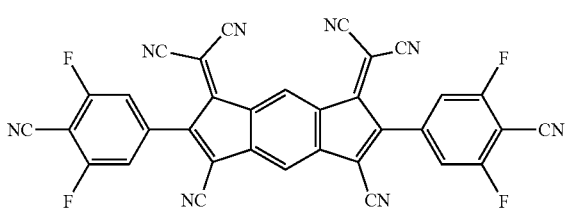
A20
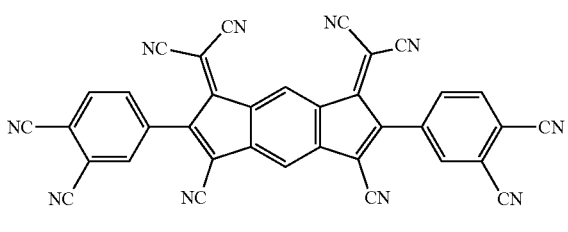
A21
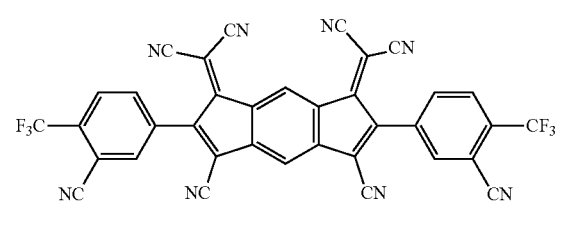

-continued
A22
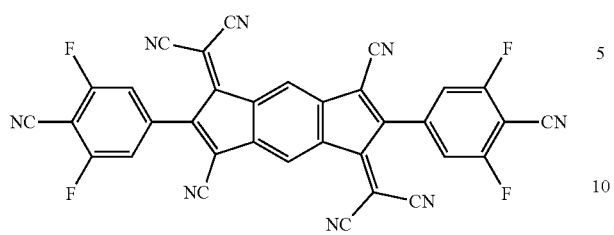
A23
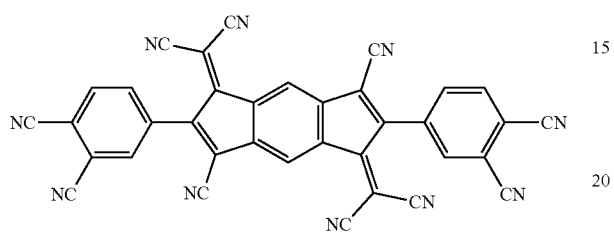
A24
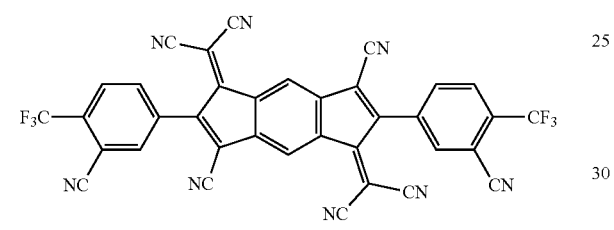
A25
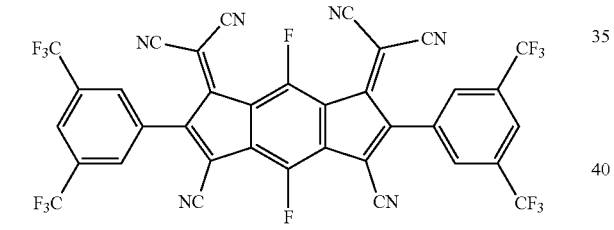
A26
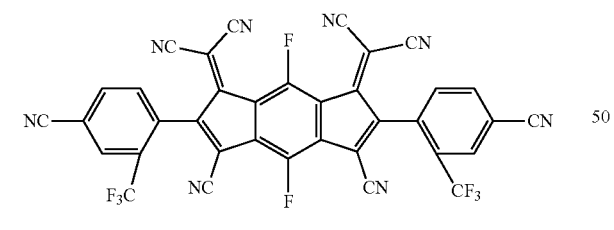
A27
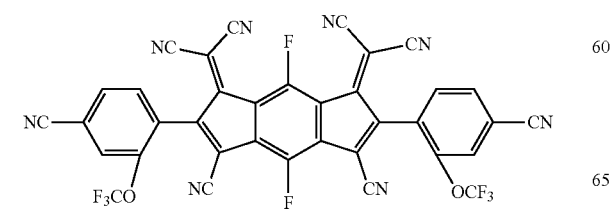
-continued
A28
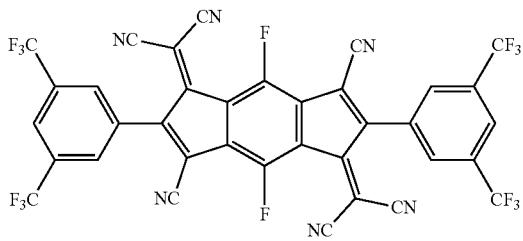
A29
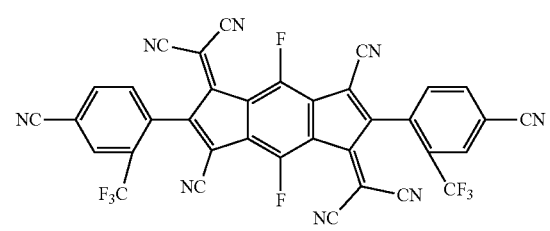
A30
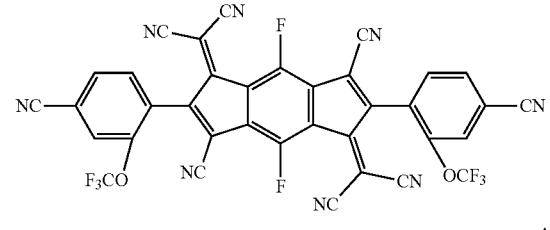
A31
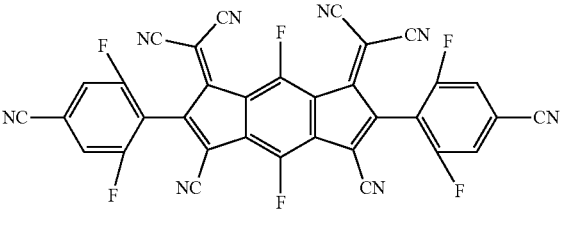
A32
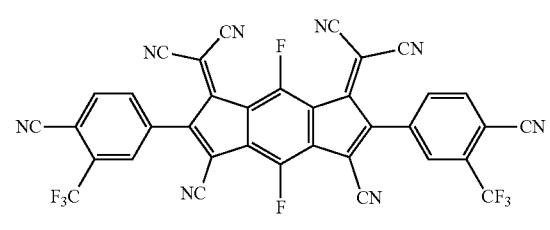
A33
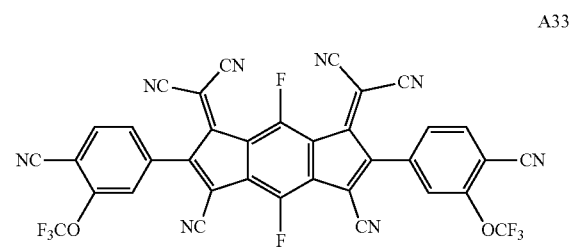

-continued
A34
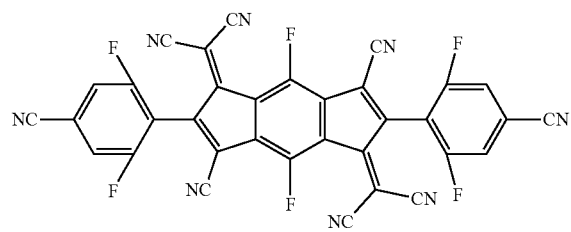
A35
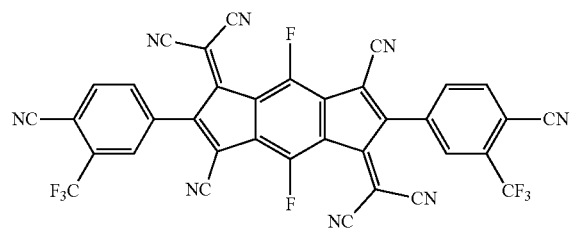
A36
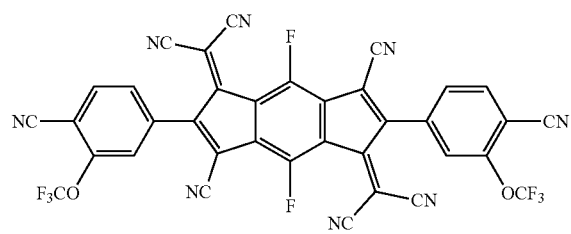
A37
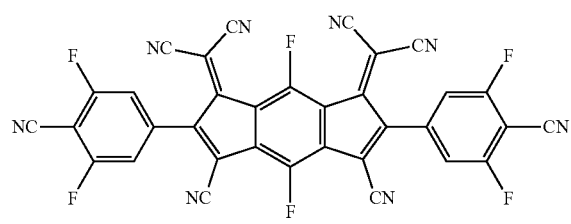
A38
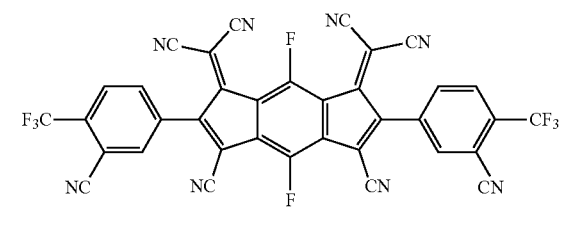
A39
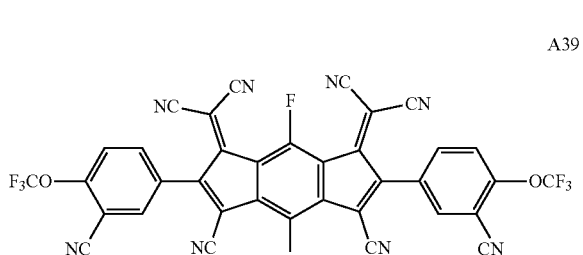
-continued
A40
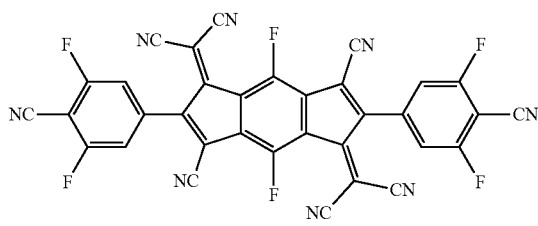
A41
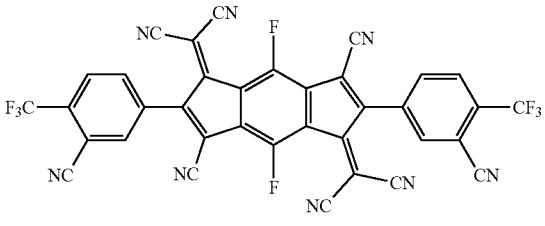
A42
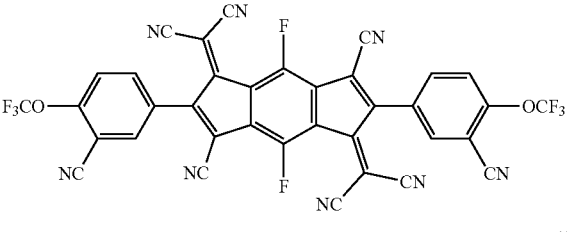
A43
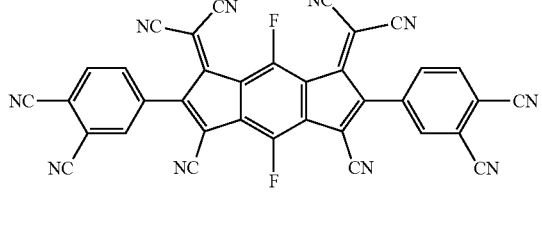
A44
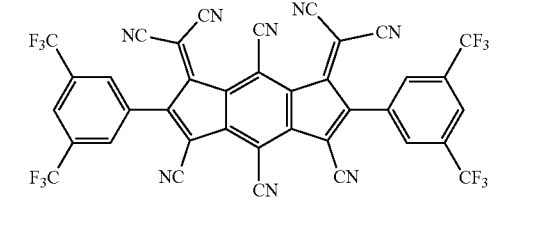
A45
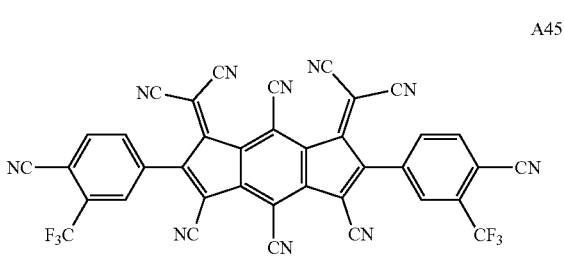

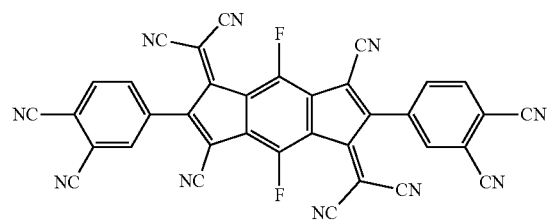
A46
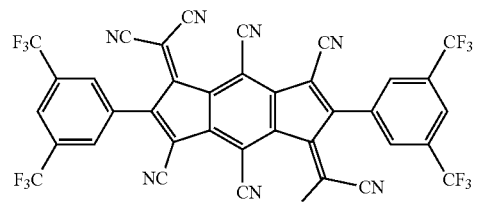
A47
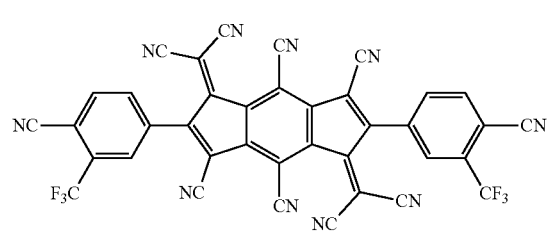
A48
5. The organic electric element according to claim 1, wherein the third compound is one or more of:
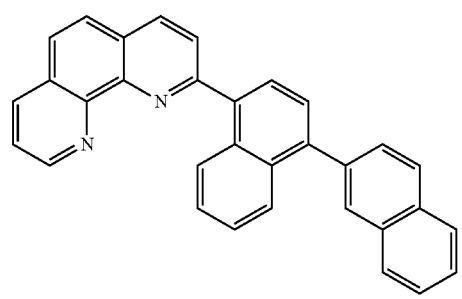
E01
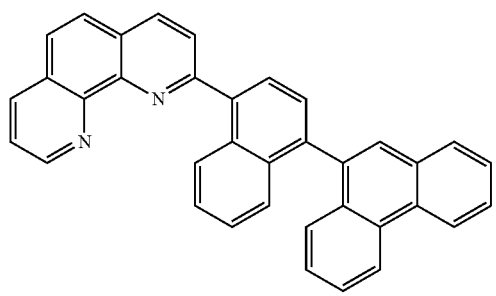
E02
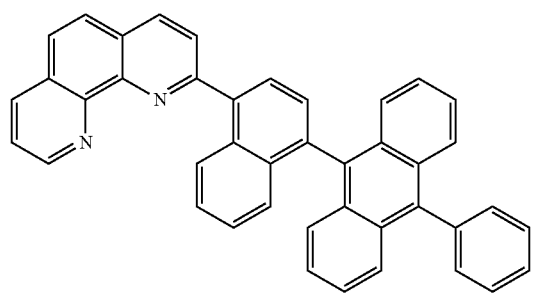
E03
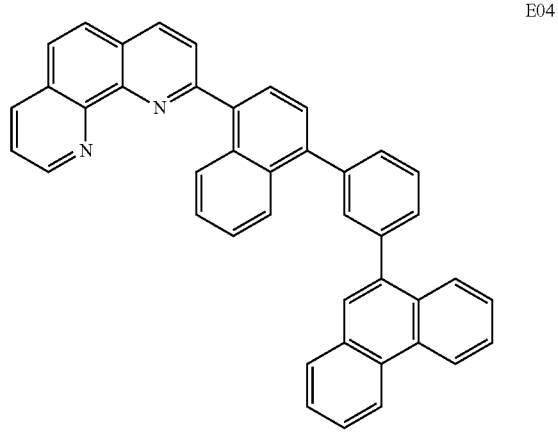
E04
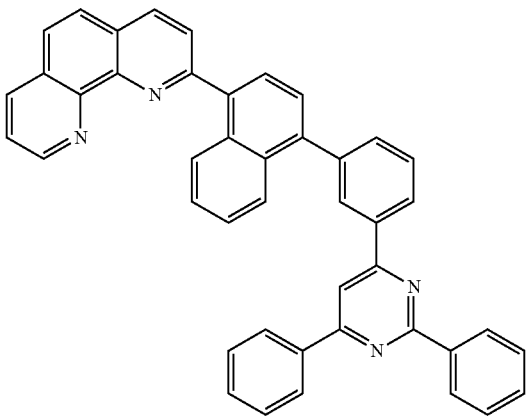
E05
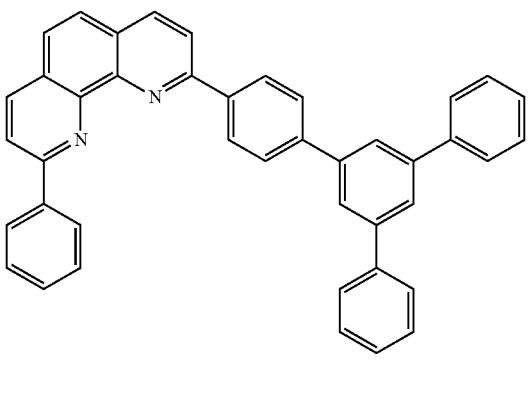
E06

-continued
E07
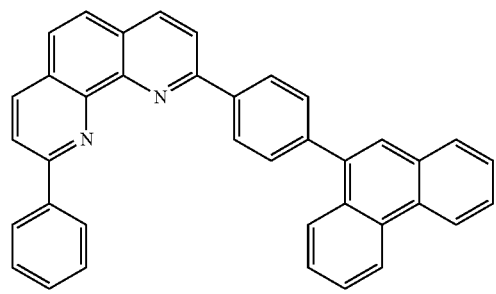
E08
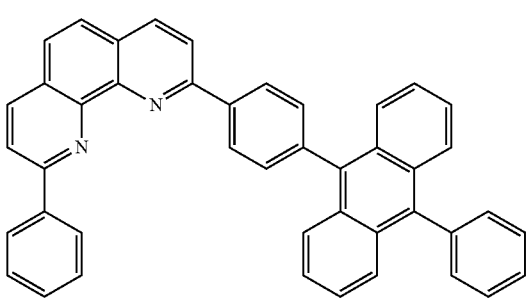
E09
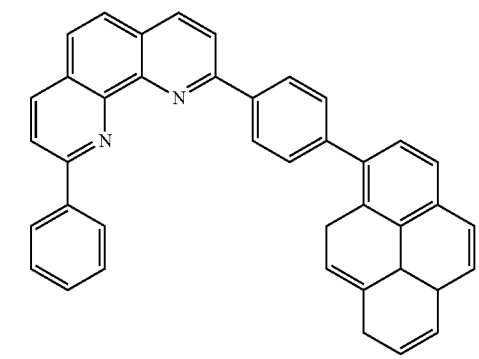
E10
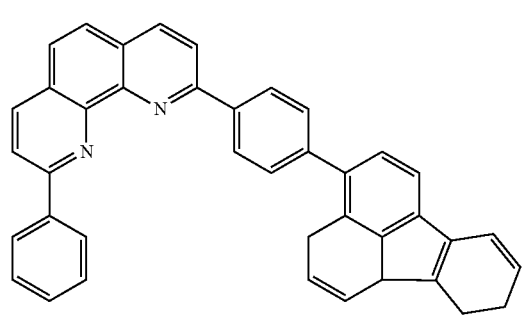
E11
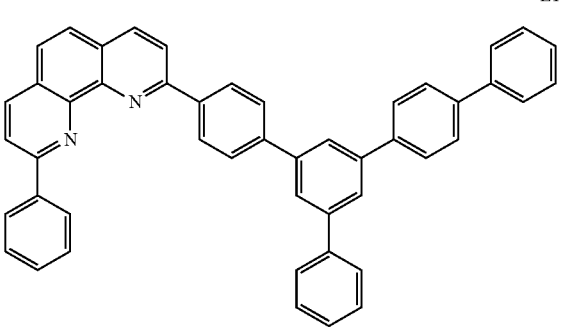
-continued
E12
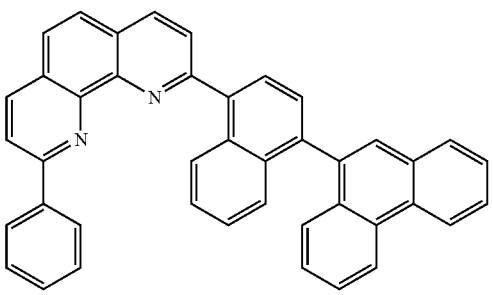
E13
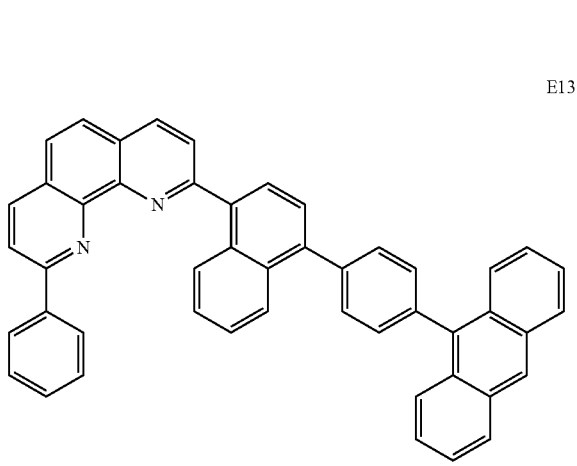
E14
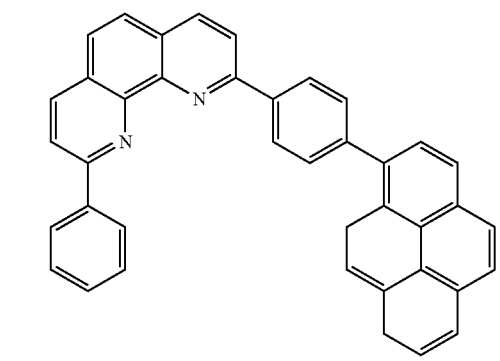
E15
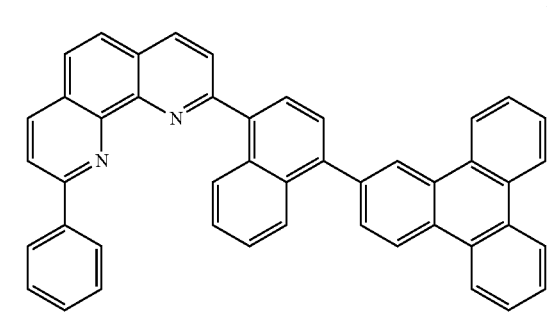

E16
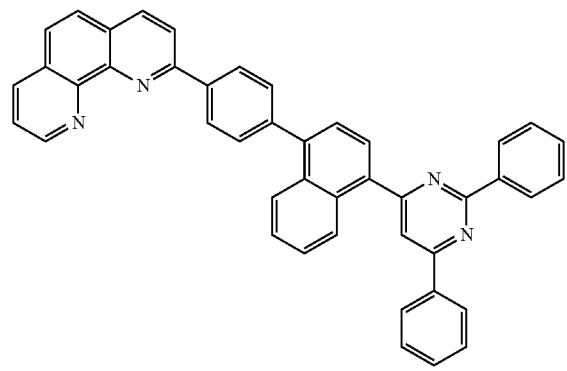
E17
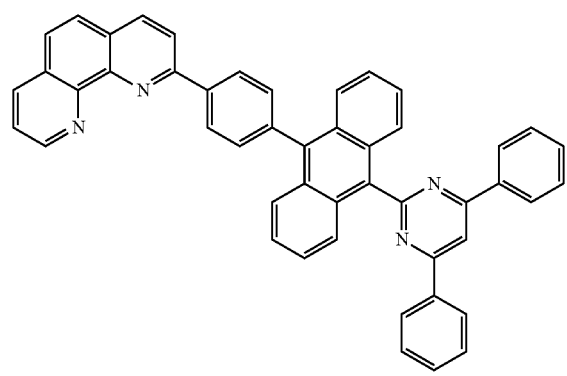
E18
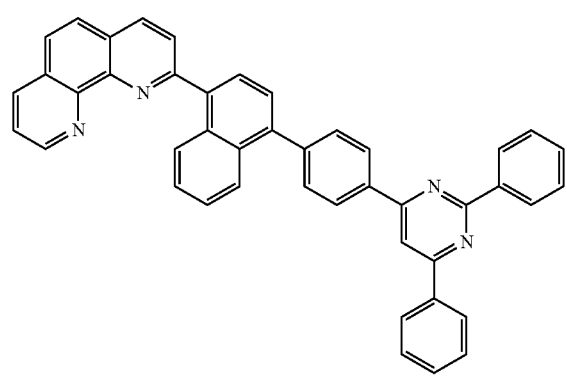
E19
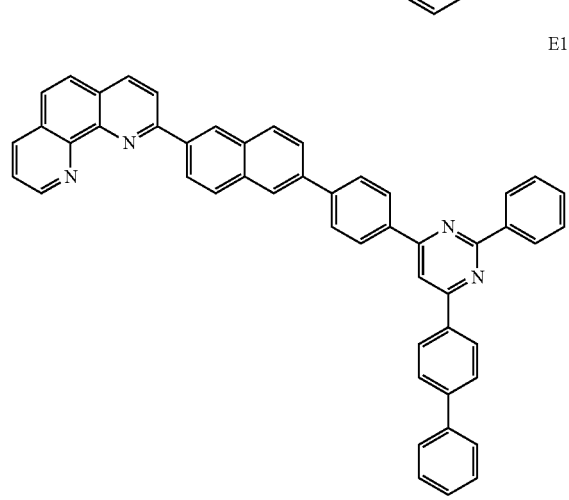
E20
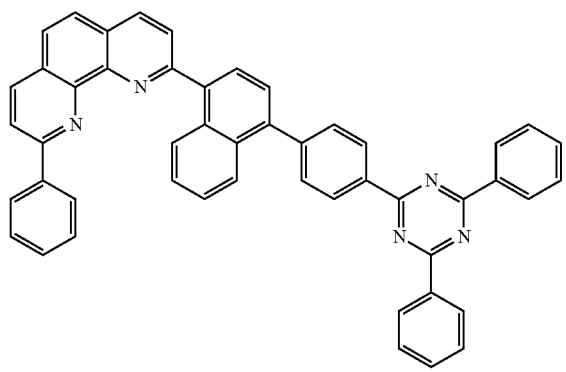
E21
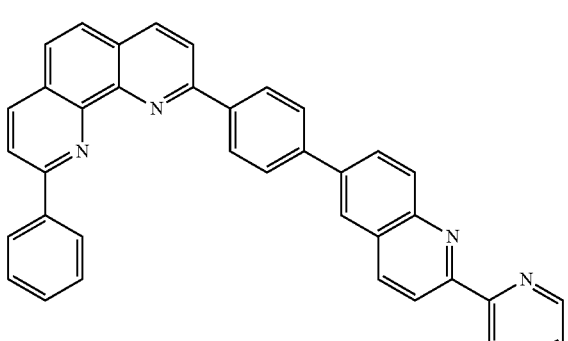
E22
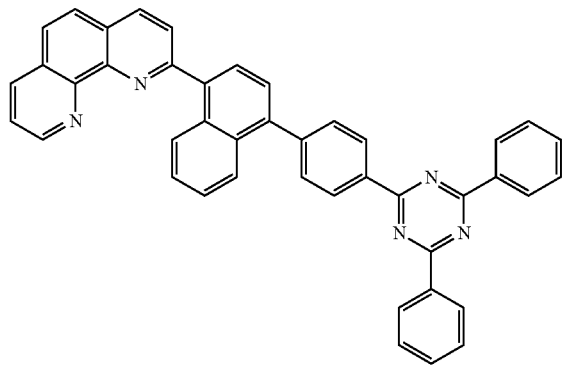

E23
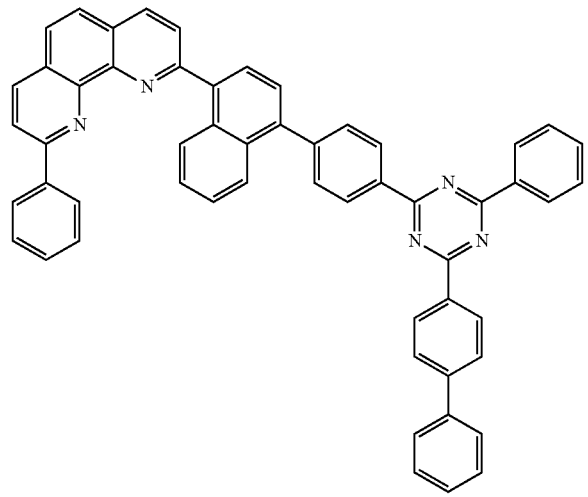
E24
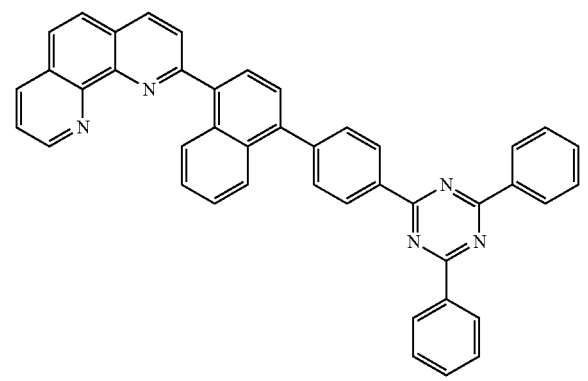
E25
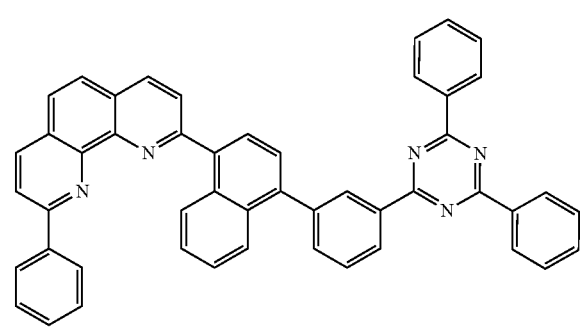
E26
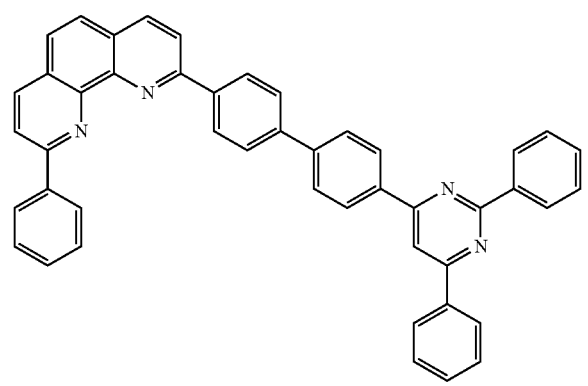
E27
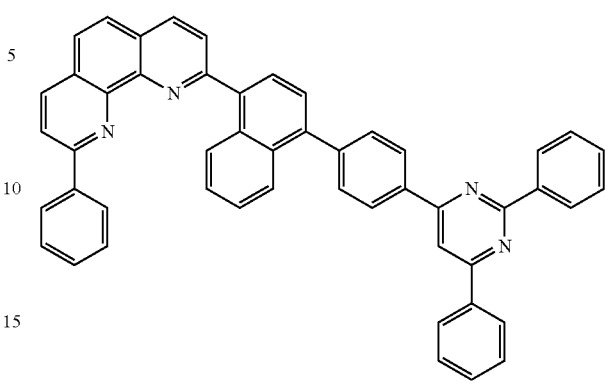
E28
E29
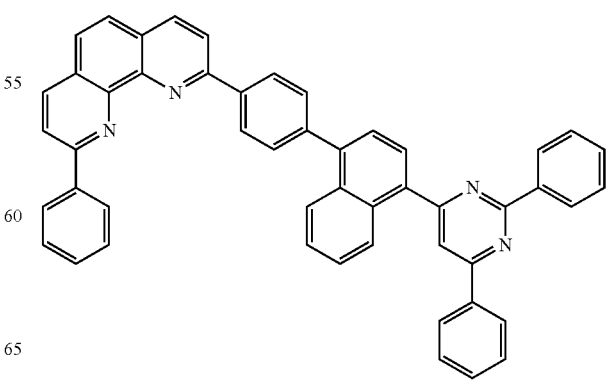

-continued
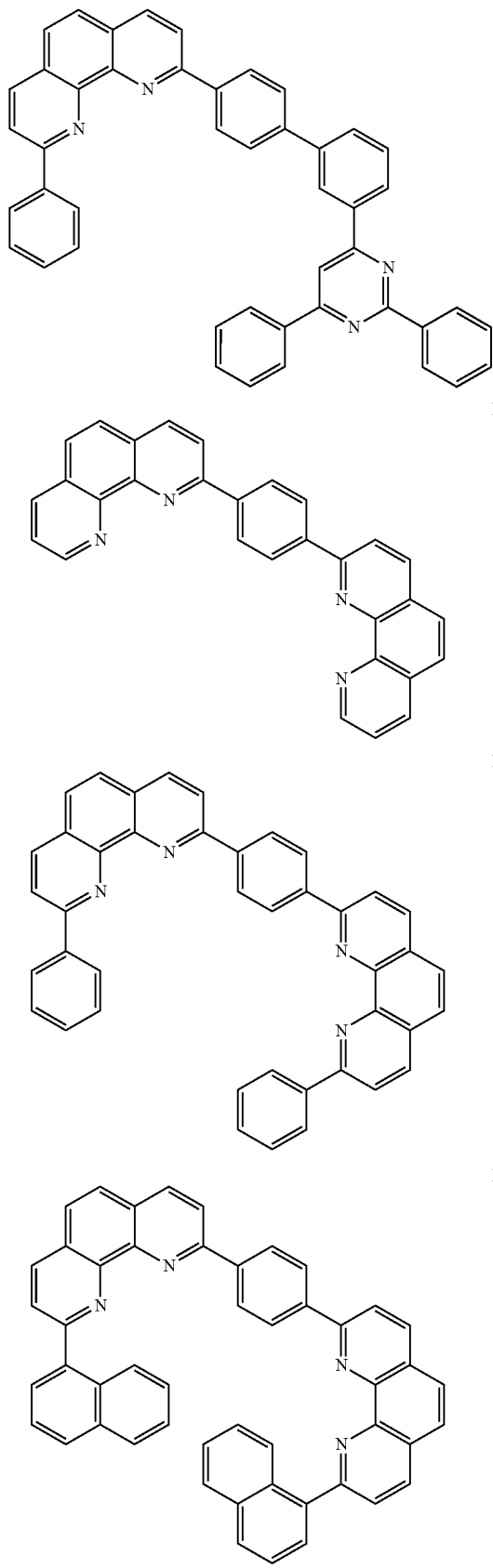
E30
E31
E32
E33
-continued
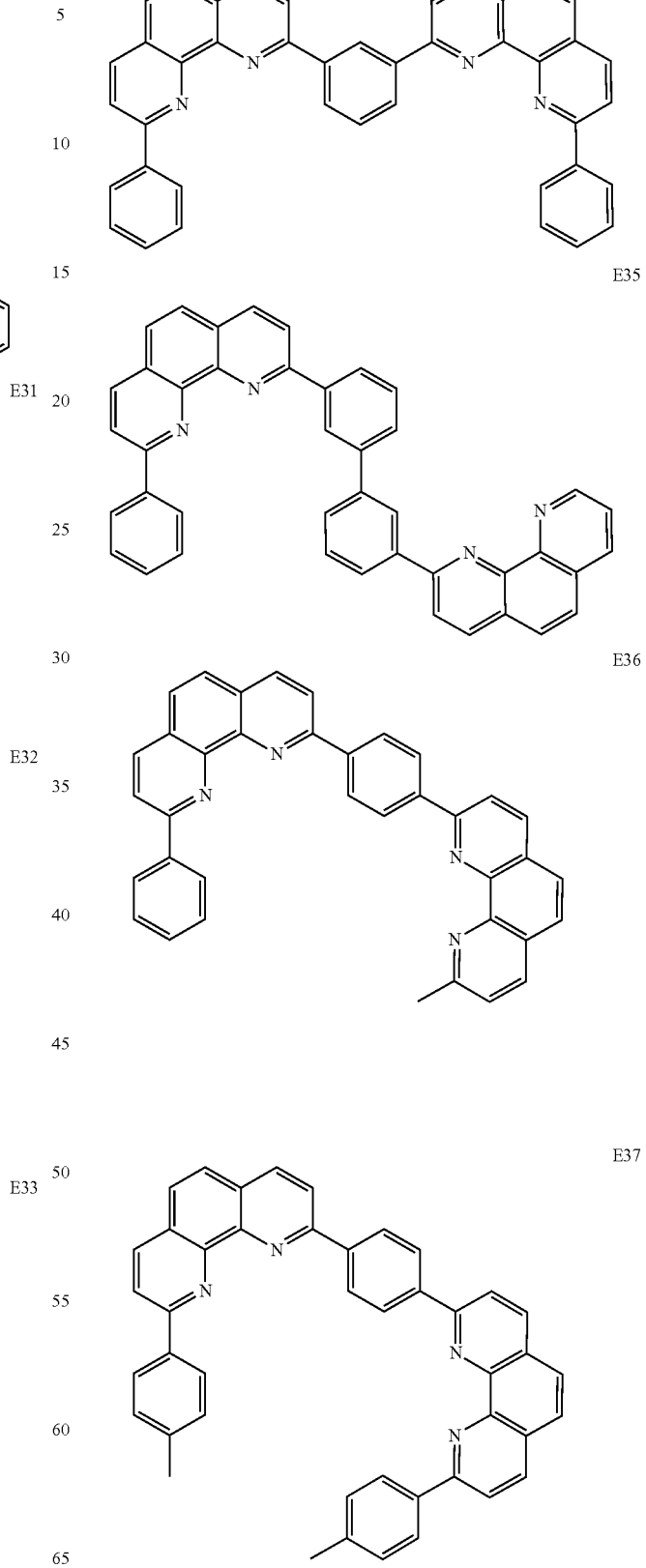
E34
E35
E36
E37

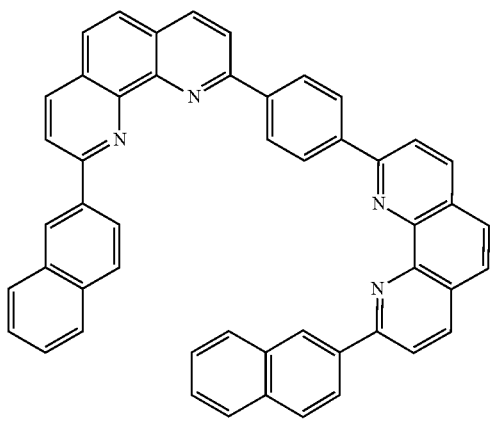

E38

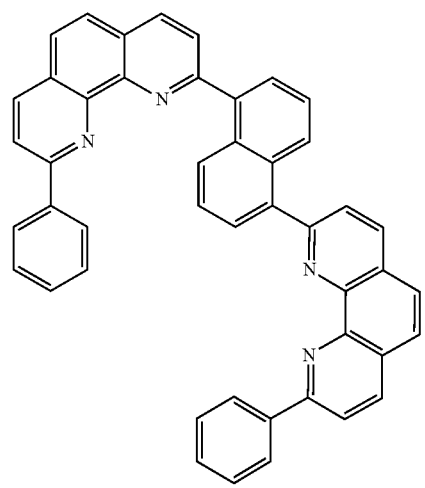

E39

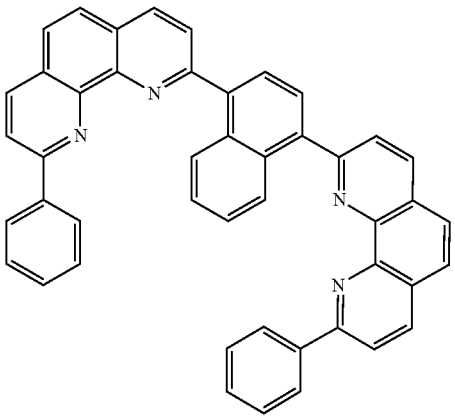

E40

6. The organic electric element according to claim 1, wherein the first electrode is an anode electrode, the second electrode is a cathode electrode, and the first layer is positioned between the second layer and the second electrode.

7. The organic electric element according to claim 1, further comprising a hole injection layer located between the first electrode and the first light emitting layer, and
the hole injection layer comprises:
a fourth compound represented by one or more of chemical formula 1 and chemical formula 2, and
a fifth compound that is one or more of:

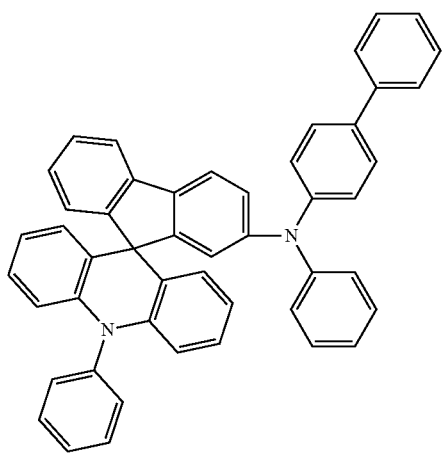

D51

-continued
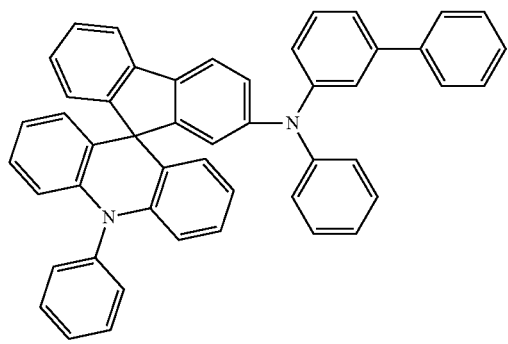
D52
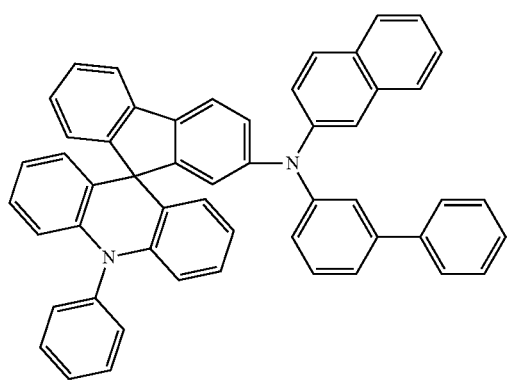
D53
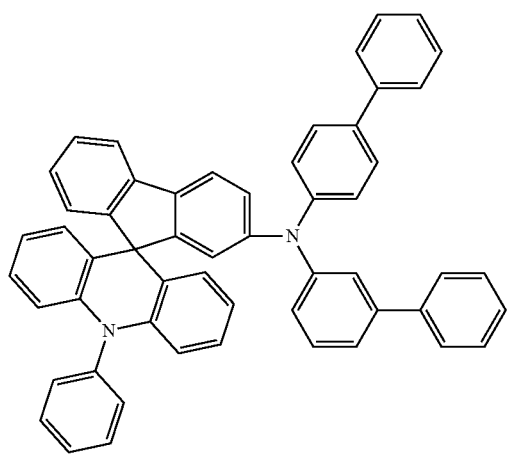
D54
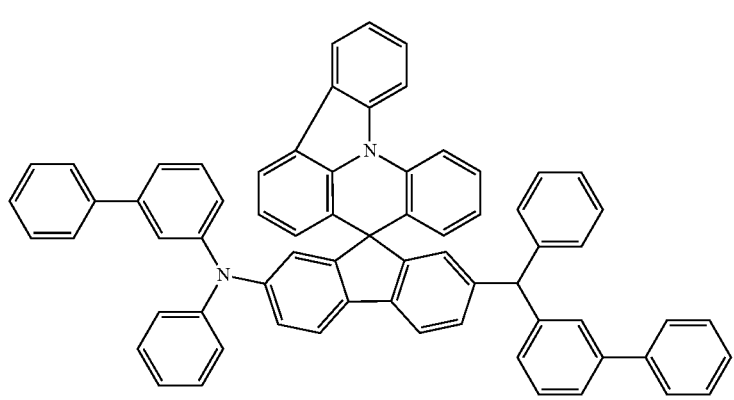
D55

-continued
D56
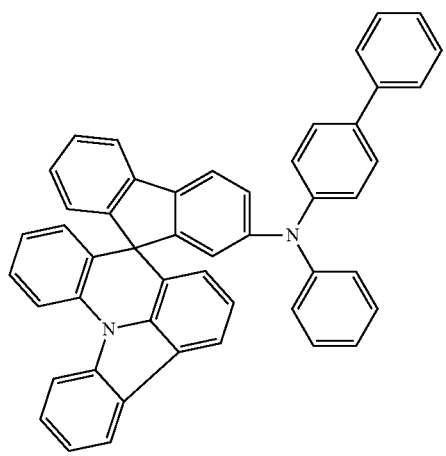
D57
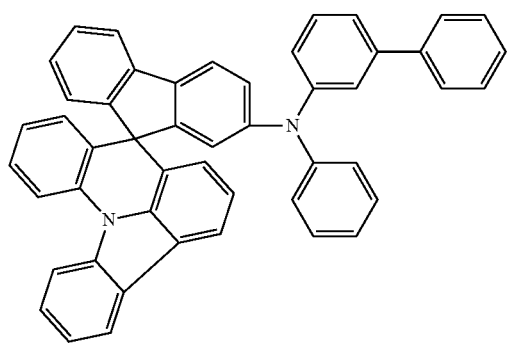
D58
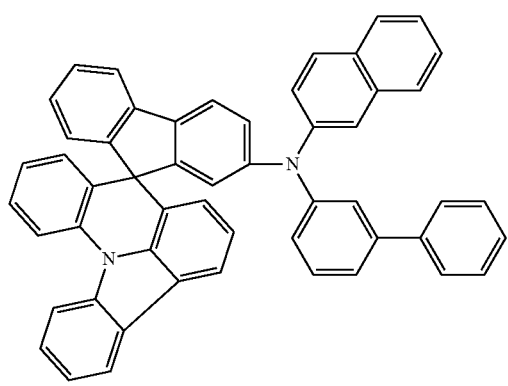
D59
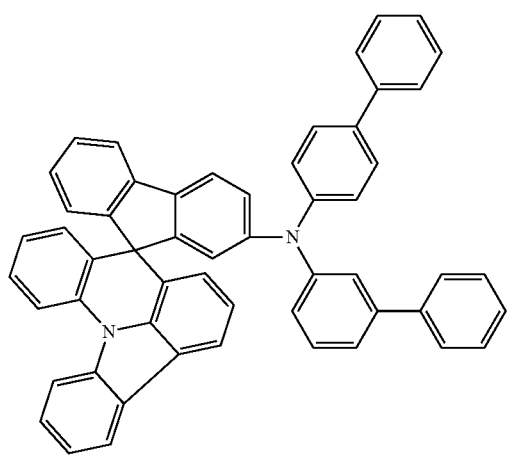

-continued
D60
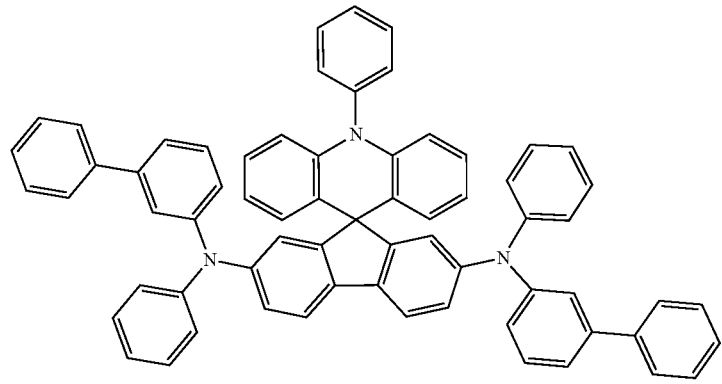
D61
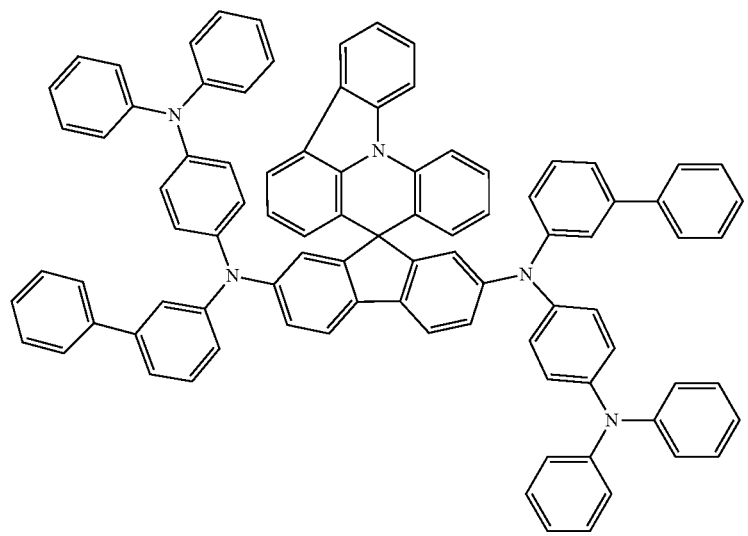
D62
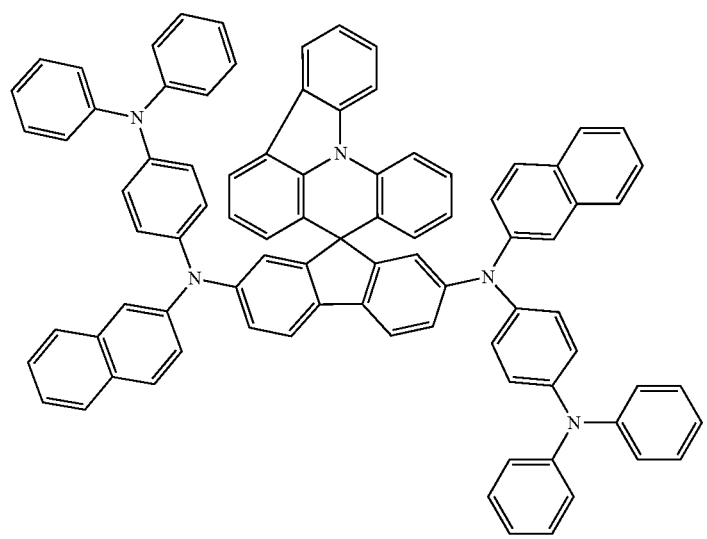

-continued
D63
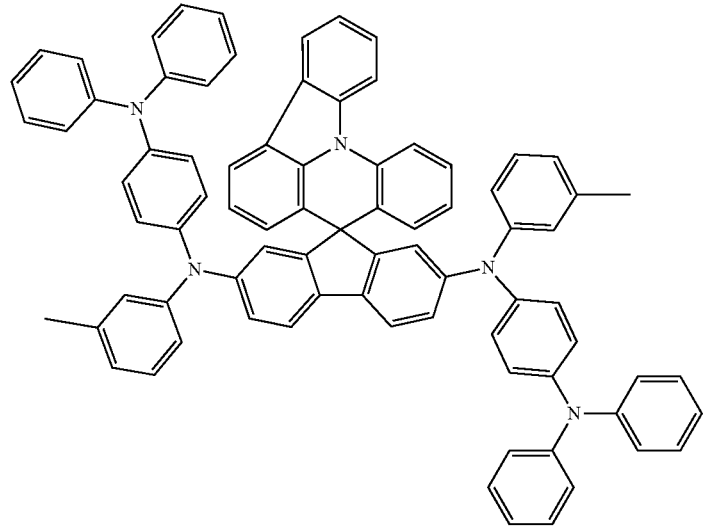
D64
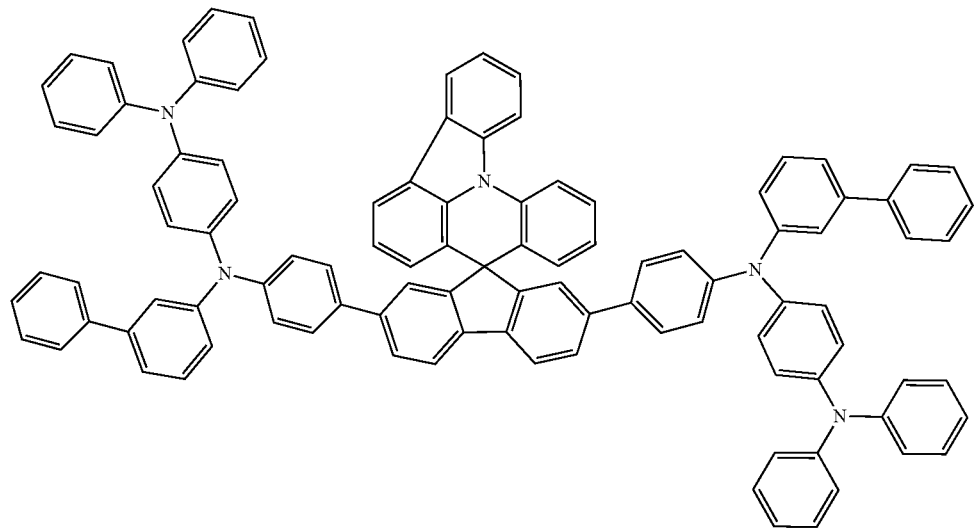
D65
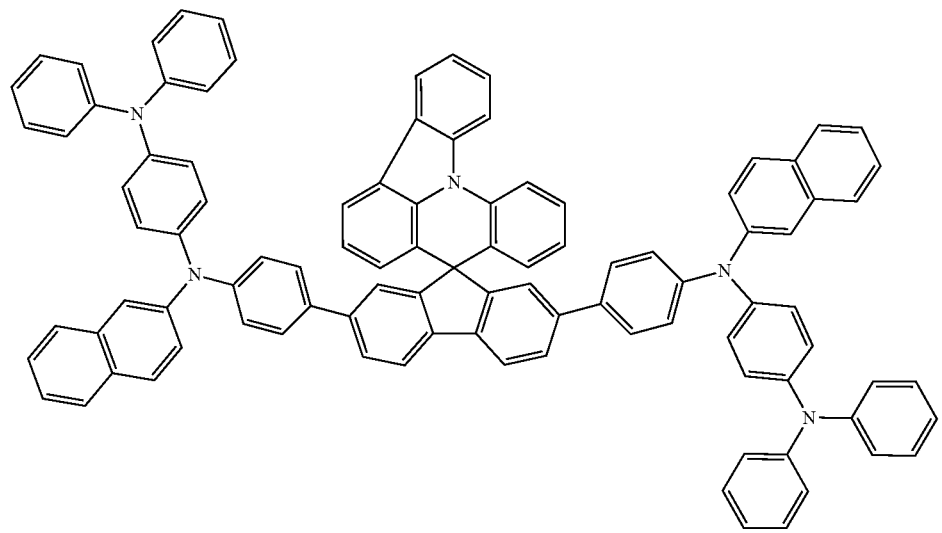

-continued

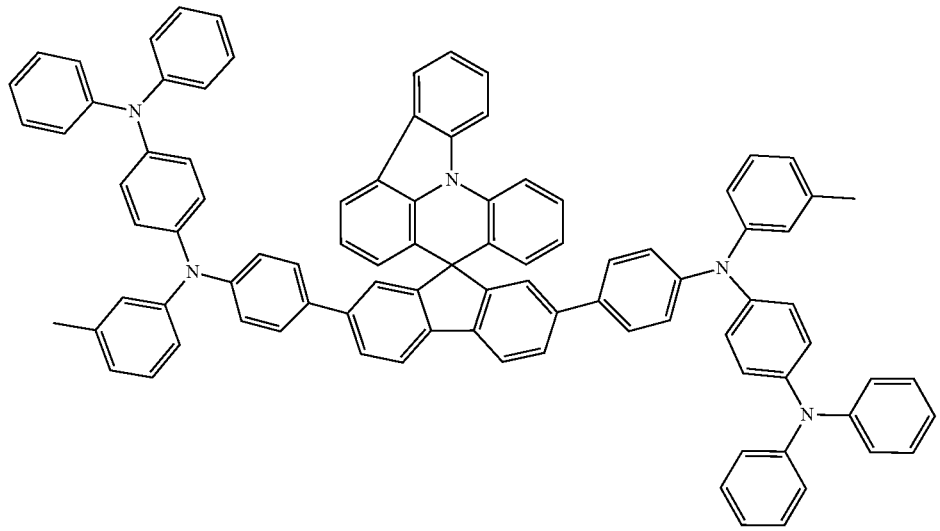

D66

8. The organic electric element according to claim 7, wherein the fourth compound is the same compound as the first compound, and the fifth compound is the same organic compound as the second compound.

9. The organic electric element according to claim 1, wherein general formula 1 is satisfied:

$$L_3-L_1 \leq 2.1 \text{ eV} \quad \text{[general formula 1]}$$

in the general formula 1,
$L_3$ is the LUMO (Lowest Unoccupied Molecular Orbital) energy level of the third compound, and
$L_1$ is the LUMO energy level of the first compound.

10. The organic electric element according to claim 1, wherein general formula 2 is satisfied:

$$L_3-H_2 \leq 2.8 \text{ eV} \quad \text{[general formula 2]}$$

in the general formula 2,
$L_3$ is the LUMO (Lowest Unoccupied Molecular Orbital) energy level of the third compound, and
$H_2$ is the HOMO (Highest Occupied Molecular Orbital) energy level of the second compound.

11. The organic electric element according to claim 1, wherein general formula 3 is satisfied:

$$0.32 \text{ eV} \leq L_1-H_2 \leq 0.8 \text{ eV} \quad \text{[general formula 3]}$$

in the general formula 3,
$L_1$ is the LUMO (Lowest Unoccupied Molecular Orbital) energy level of the first compound, and
$H_2$ is the HOMO (Highest Occupied Molecular Orbital) energy level of the second compound.

12. A display panel comprising a subpixel comprising the organic electric element of claim 1.

13. A display device comprising;
the display panel of claim 12; and
a driving circuit for driving the display panel.

* * * * *